US008617882B2

(12) United States Patent
Miller et al.

(10) Patent No.: US 8,617,882 B2
(45) Date of Patent: Dec. 31, 2013

(54) SKIN-DERIVED PRECURSOR CELLS AND USES THEREOF

(75) Inventors: Freda D. Miller, Toronto (CA); Jeff Biernaskie, Toronto (CA)

(73) Assignee: The Hospital for Sick Children, Toronto (CA)

(*) Notice: Subject to any disclaimer, the term of this patent is extended or adjusted under 35 U.S.C. 154(b) by 318 days.

(21) Appl. No.: 12/602,845

(22) PCT Filed: Jun. 6, 2008

(86) PCT No.: PCT/CA2008/001104
§ 371 (c)(1),
(2), (4) Date: May 7, 2010

(87) PCT Pub. No.: WO2008/148218
PCT Pub. Date: Dec. 11, 2008

(65) Prior Publication Data
US 2010/0239640 A1 Sep. 23, 2010

Related U.S. Application Data

(60) Provisional application No. 60/934,419, filed on Jun. 13, 2007, provisional application No. 60/933,302, filed on Jun. 6, 2007.

(51) Int. Cl.
C12N 5/07 (2010.01)

(52) U.S. Cl.
USPC .......................................................... 435/347

(58) Field of Classification Search
CPC combination set(s) only.
See application file for complete search history.

(56) References Cited

U.S. PATENT DOCUMENTS

| | | | |
|---|---|---|---|
| 5,318,907 A | 6/1994 | Ronnett et al. | |
| 5,338,839 A | 8/1994 | McKay et al. | |
| 5,589,376 A | 12/1996 | Anderson et al. | |
| 5,633,426 A | 5/1997 | Namikawa et al. | |
| 5,654,183 A | 8/1997 | Anderson et al. | |
| 5,672,499 A | 9/1997 | Anderson et al. | |
| 5,693,482 A | 12/1997 | Anderson et al. | |
| 5,733,727 A | 3/1998 | Field | |
| 5,753,506 A | 5/1998 | Johe | |
| 5,800,811 A * | 9/1998 | Hall et al. | 424/93.7 |
| 5,824,489 A | 10/1998 | Anderson et al. | |
| 5,849,553 A | 12/1998 | Anderson et al. | |
| 5,912,175 A | 6/1999 | Wille, Jr. | |
| 5,928,947 A | 7/1999 | Anderson et al. | |
| 5,942,225 A | 8/1999 | Bruder et al. | |
| 6,001,654 A | 12/1999 | Anderson et al. | |
| 6,050,990 A | 4/2000 | Tankovich et al. | |
| 6,093,531 A | 7/2000 | Bjornson et al. | |
| 6,153,388 A | 11/2000 | Reintgen | |
| 6,497,872 B1 | 12/2002 | Weiss et al. | |
| 6,497,875 B1 * | 12/2002 | Sorrell et al. | 424/93.7 |
| 6,528,245 B2 | 3/2003 | Sanchez-Ramos et al. | |
| 2002/0016002 A1 | 2/2002 | Toma et al. | |
| 2002/0123143 A1 | 9/2002 | Toma et al. | |
| 2003/0003572 A1 | 1/2003 | Anderson et al. | |
| 2003/0003574 A1 | 1/2003 | Toma et al. | |
| 2003/0077823 A1 | 4/2003 | Li et al. | |
| 2004/0033597 A1 | 2/2004 | Toma et al. | |
| 2004/0110288 A1 | 6/2004 | Morrison et al. | |
| 2004/0115808 A1 | 6/2004 | Pachnis | |
| 2005/0214344 A1 * | 9/2005 | Barrows et al. | 424/426 |
| 2006/0088505 A1 | 4/2006 | Hoffmann et al. | |
| 2006/0263876 A1 | 11/2006 | Miller et al. | |
| 2007/0248574 A1 | 10/2007 | Miller et al. | |
| 2008/0038770 A1 | 2/2008 | Hansford et al. | |
| 2009/0053802 A1 | 2/2009 | Toma et al. | |
| 2009/0142834 A1 | 6/2009 | Toma et al. | |

FOREIGN PATENT DOCUMENTS

| | | | | |
|---|---|---|---|---|
| EP | 1950284 | | 7/2008 | |
| WO | WO 01/53461 | | 7/2001 | |
| WO | WO 03/010243 | | 2/2003 | |
| WO | WO 03/024406 | | 3/2003 | |
| WO | WO 2005/071063 | * | 8/2005 | ............... C12N 5/00 |
| WO | WO 2008/148218 | | 12/2008 | |

OTHER PUBLICATIONS

Prouty et al., American Journal of Pathology, vol. 148, No. 6, 1996, pp. 1871-1885.*
Alonso et al., "Stem Cells of the Skin Epithelium," *Proc. Natl. Acad. Sci. USA* 100:11830-11835 (2003).
Anderson, "Molecular Control of Cell Fate in the Neural Crest: The Sympathoadrenal Lineage," *Annu. Rev. Neurosci.* 16:129-158 (1993).
Biernaskie et al., "Isolation of skin-derived precursors (SKPs) and differentiation and enrichment of Their Schwann Cell Progeny," *Nat. Protoc.* 1:2803-2812 (2006).
Cai et al., "Stem Cell and Precursor Cell Therapy," *Neuromol. Med.* 2:233-249 (2002).
Cao et al., "Stem Cell Repair of Central Nervous System Injury," *J. Neurosci. Res.* 68:501-510 (2002).
Chepko et al., "Ultrastructure of the Putative Stem Cell Niche in Rat Mammary Epithelium," *Tissue Cell.* 35:83-93 (2003).
Dupin et al., "The Neural Crest Stem Cells: Control of Neural Crest Cell Fate and Plasticity by Endothelin-3," *An. Acad. Bras. Cienc.* 73:533-545 (2001).
Fernandes K J L et al., "A Dermal Niche for Multipotent Adult Skin-Derived Precursor Cells," Nature Cell Biology. 6(11):1082-1093 (2004).
Freshney, *Culture of Animal Cells: A Manual of Basic Technique*, New York: A.R. Liss, Inc. 215-225 (1987).
Gambardella et al., "The Multifaceted Adult Epidermal Stem Cell," *Curr. Opin. Cell Biol.* 15:771-777 (2003).

(Continued)

*Primary Examiner* — Allison Ford
*Assistant Examiner* — Yvonne Pyla
(74) *Attorney, Agent, or Firm* — Clark & Elbing LLP

(57) ABSTRACT

The invention features methods of inducing hair follicle formation in a mammal by transplantation of skin-derived precursors (SKPs) and keratinocytes into the skin of the mammal. The invention also features compositions and kits including SKPs and keratinocytes. In other aspects, the invention features methods for producing dermal sheets from SKPs, methods for using such sheets and dermal sheets produced by SKPs.

12 Claims, 54 Drawing Sheets

(56) References Cited

OTHER PUBLICATIONS

Jahoda et al., "Induction of Hair Growth by Implantation of Cultured Dermal Papilla Cells," *Nature* 311:560-562 (1984).

Jahoda et al., "Hair Follicle Dermal Cells Differentiate into Adipogenic and Osteogenic Lineages," *Exp. Dermatol.* 12:849-859 (2003).

Kishimoto et al., "Selective Activation of the Versican Promoter by Epithelial-Mesenchymal Interactions during Hair Follicle Development", *Proc. Natl. Acad. Sci. USA* 96:7336-7341, (1999).

Kruger et al., "Neural Crest Stem Cells Persist in the Adult Gut but Undergo Changes in Self-renewal, Neuronal Subtype Potential, and Factor Responsiveness," *Neuron*. 35:657-669 (2002).

Kumamoto et al., "Hair Follicles Serve as Local Reservoirs of Skin Mast Cell Precursors," *Blood* 102:1654-1660 (2003).

Lako et al., "Hair Follicle Dermal Cells Repopulate the Mouse Haematopoietic System," *J. Cell Sci.* 115:3967-3974 (2002).

Lavker et al., "Hair Follicle Stem Cells," *J. Investig. Dermatol Symp. Proc.* 8:28-38 (2003).

Li et al.,"Nestin Expression in Hair Follicle Sheath Progenitor Cells," *Proc. Natl. Acad. Sci. USA* 100:9958-9961 (2003).

Lindvall et al., "Stem Cell Therapy for Human Neurodegenerative Disorders—How to Make it Work," *Nat. Med.* 10:S42-S50 (2004).

Lyle et al., "The C8/144B Monoclonal Antibody Recognizes Cytokeratin 15 and Defines the Location of Human Hair Follicle Stem Cells," *J. Cell Sci.* 111:3179-3188, (1998).

McElwee et al., "Cultured Peribulbar Dermal Sheath Cells Can Induce Hair Follicle Development and Contribute to the Dermal Sheath and Dermal Papilla," *J. Invest. Dermatol.* 121:1267-1275 (2003).

Osada et al., "Characterization of Vibrissa Germinative Cells: Transition of Cell Types," *Exp. Dermatol.* 10:430-437 (2001).

Oshima et al., "Morphogenesis and Renewal of Hair Follicles from Adult Multipotent Stem Cells," *Cell* 104:233-245 (2001).

Ouji et al., "Promotion of Hair Follicle Development and Trichogenesis by WNT-10b in Cultured Embryonic Skin and in Reconstituted Skin," *Biochem. Biophys. Res. Commun.* 345:581-587 (2006).

Oyelese et al., "Neural Trans-Differentiation of Plastic Adherent and Non-adherent Bone Marrow Stem Cells," *31st Annual Meeting of the Society for Neuroscience*, California (Abstract/Poster) (Nov. 10-15, 2001).

Pellegrini et al., "The Control of Epidermal Stem Cells (Holoclones) in the Treatment of Massive Full-Thickness Burns with Autologous Keratinocytes Cultured on Fibrin," *Transplantation* 68:868-879 (1999).

Peters et al., "Migration of Melanoblasts into the Developing Murine Hair Follicle Is Accompanied by Transient c-Kit Expression," *J. Histochem. Cytochem*. 50:751-766 (2002).

Peters et al., "Kit Is Expressed by Epithelial Cells in Vivo," *J. Invest. Dermatol*. 121:976-984 (2003).

Rao, "Multipotent and Restricted Precursors in the Central Nervous System," *Anat. Rec.* (*New Anat.*) 257:137-148 (1999).

Rendl et al., "BMP Signaling in Dermal Papilla Cells Is Required for Their Hair Follicle-Inductive Properties," *Genes Dev*. 22:543-57, (2008).

Schouten et al., "A Review and Rationale for the Use of Cellular Transplantation as a Therapeutic Strategy for Traumatic Brain Injury," *J. Neurotrauma*. 21(11):1501-1538 (2004).

Shamblott et al., "Derivation of Pluripotent Stem Cells from Cultured Human Primordial Germ Cells," *Proc. Natl. Acad. Sci. USA* 95: 13726-13731 (1998).

Shamblott et al., "Human Embryonic Germ Cell Derivatives Express a Broad Range of Developmentally Distinct Markers and Proliferate Extensively In Vitro," *Proc. Natl. Acad. Sci. USA* 98: 113-118 (2001).

Tiede et al., "Hair Follicle Stem Cells: Walking the Maze," *Eur. J. Cell Biol.* 86: 355-376 (2007).

Toma et al., "Isolation of Multipotent Adult Stem Cells from the Dermis of Mammalian Skin," *Nat. Cell Biol.* 3:778-784 (2001).

Trempus et al., "Enrichment for Living Murine Keratinocytes from the Hair Follicle Bulge with the Cell Surface Marker CD34," *J. Invest. Dermatol*. 120:501-511 (2003).

Wu et al., "Hair Follicle Reformation Induced by Dermal Papilla Cells from Human Scalp Skin," *Arch. Dermatol. Res.* 298:183-190 (2006).

Zheng et al., "Organogenesis from Dissociated Cells: Generation of Mature Cycling Hair Follicles from Skin-Derived Cells," *J.Invest. Dermatol*. 124:867-876 (2005).

Extended European Search Report for EP 08757235.0, dated Dec. 21, 2010.

International Search Report International Application No. PCT/CA2008/001104, dated Sep. 9, 2008.

International Preliminary Report on Patentability for International Application No. PCT/CA2008/001104, dated Dec. 7, 2009.

\* cited by examiner

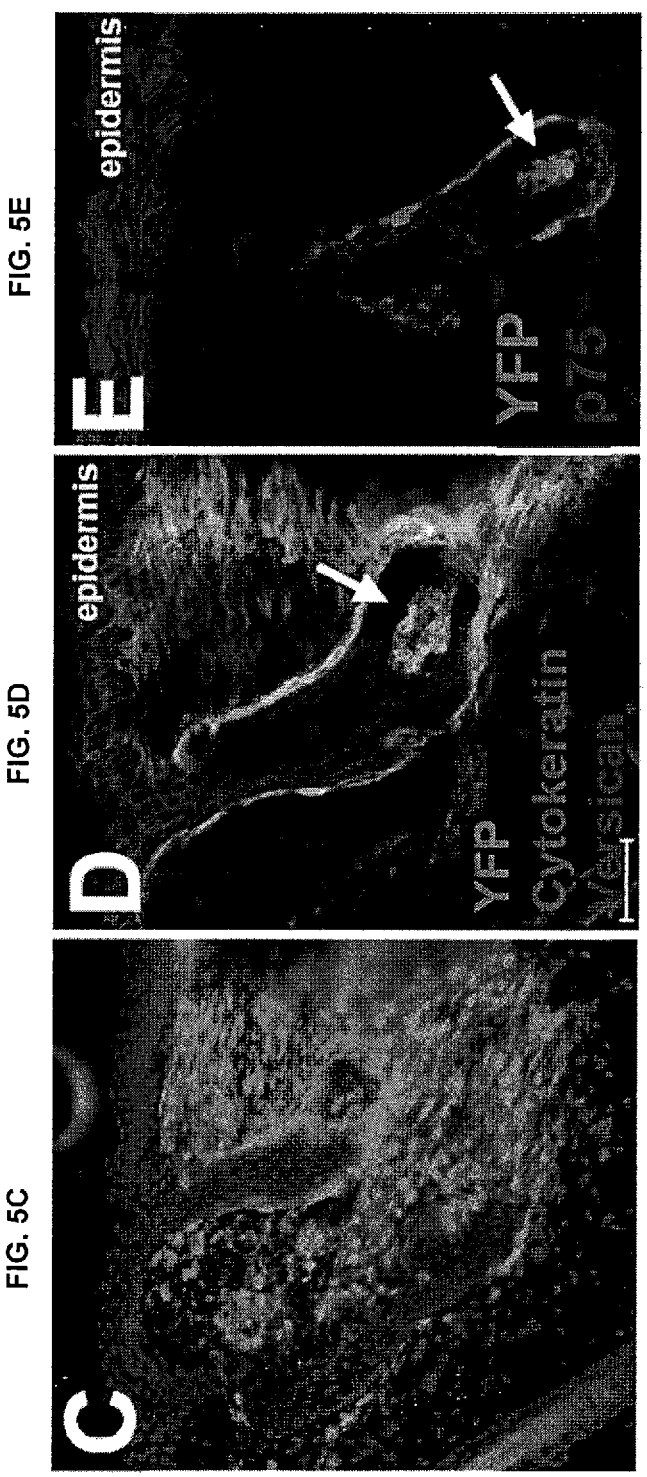

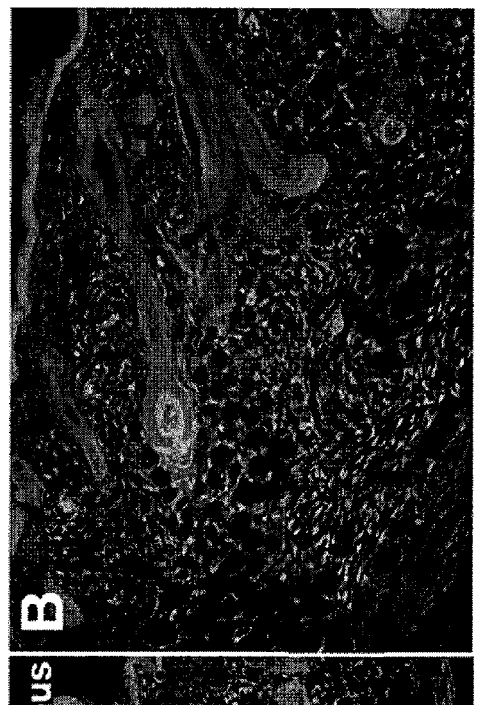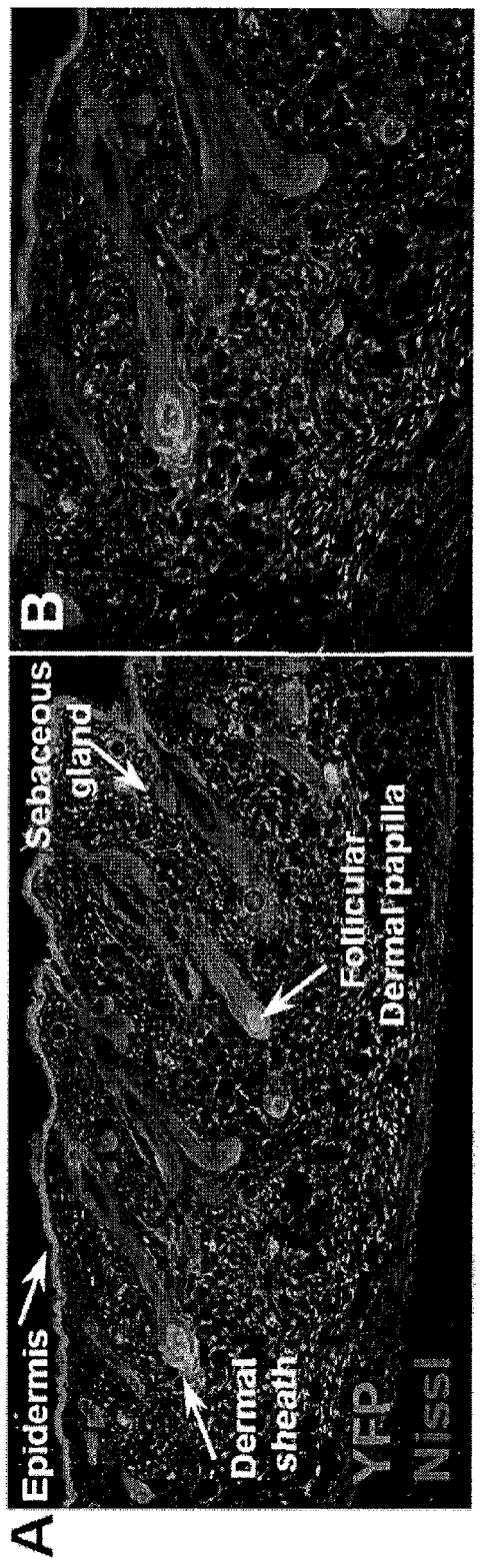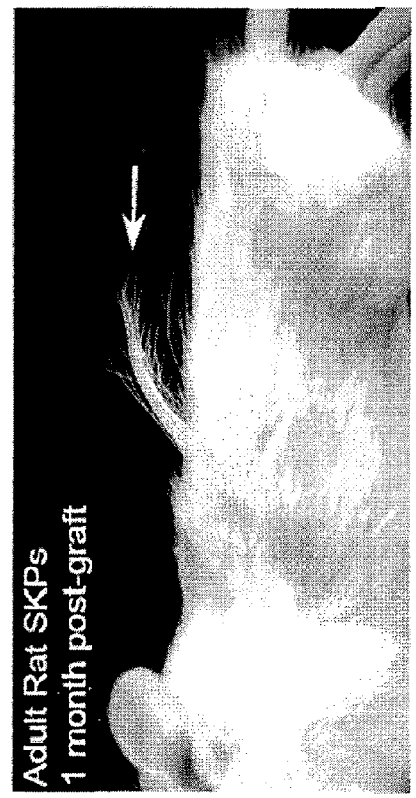
FIG. 6A
FIG. 6B
FIG. 6C Adult Rat SKPs 1 month post-graft
FIG. 6D

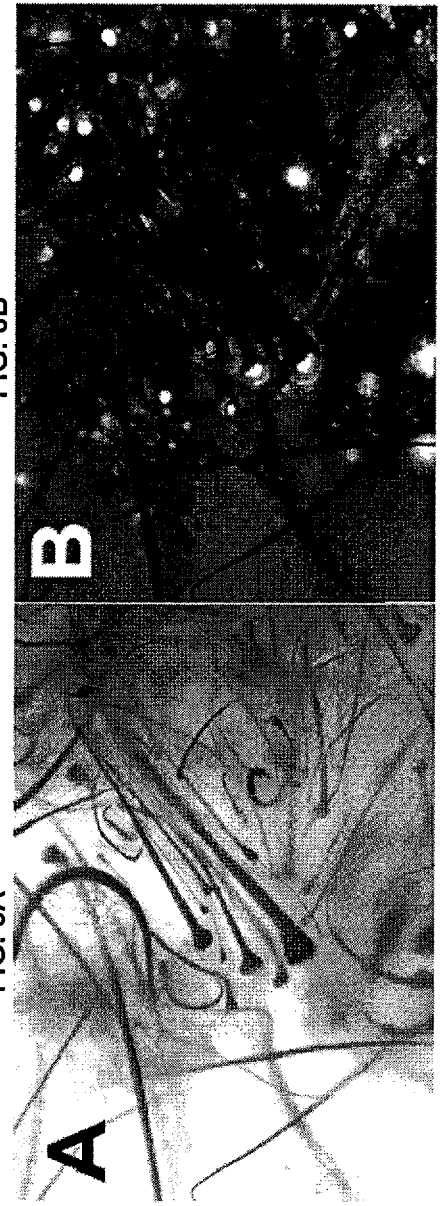
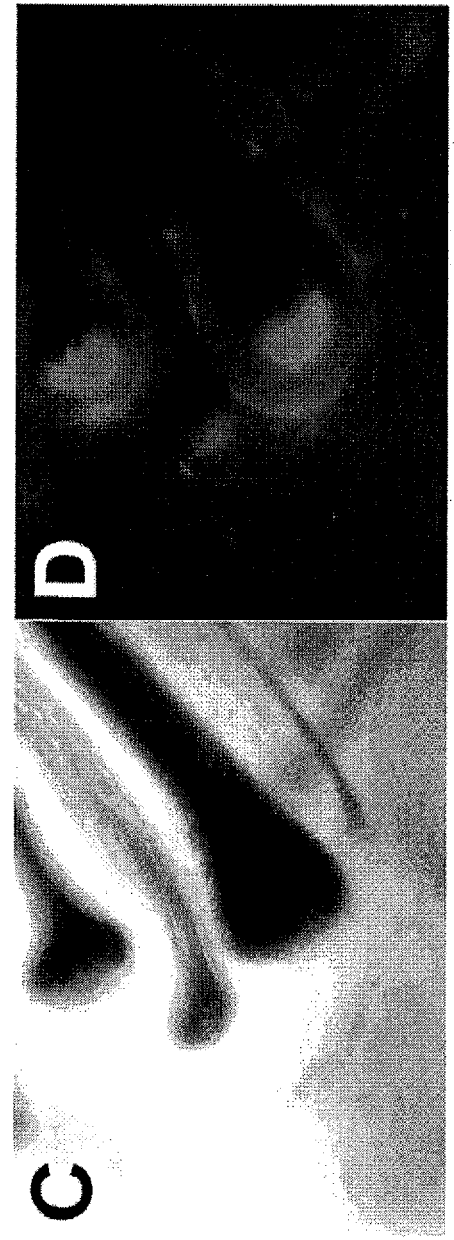

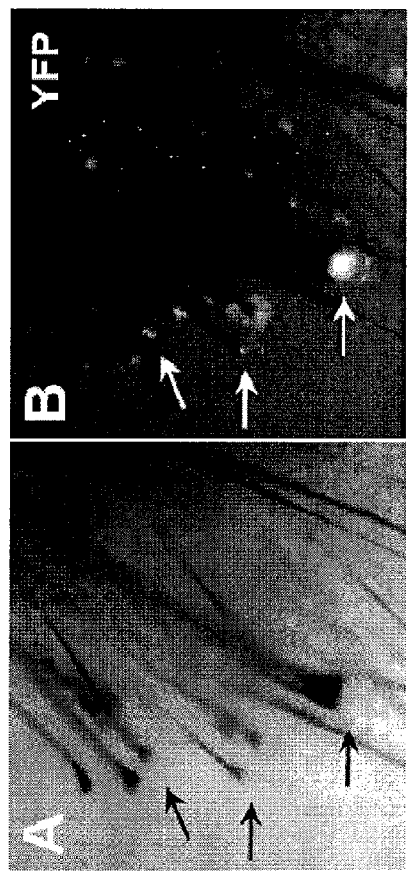
FIG. 9A
FIG. 9B
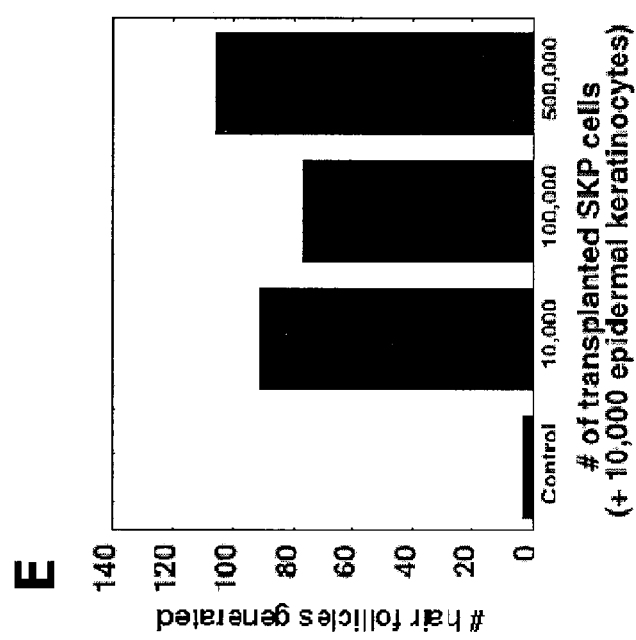
FIG. 8E

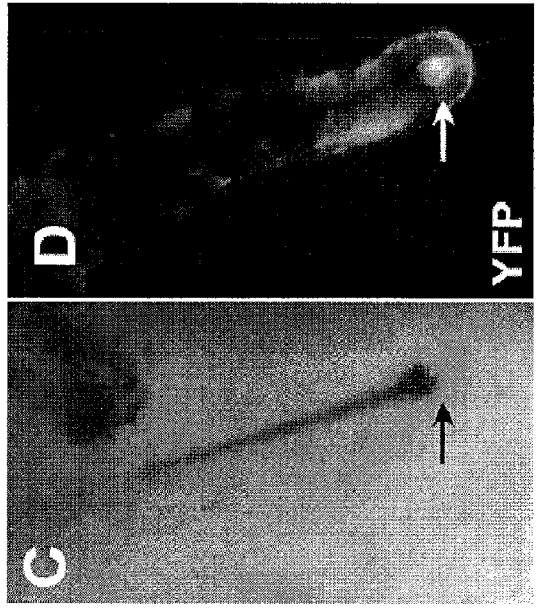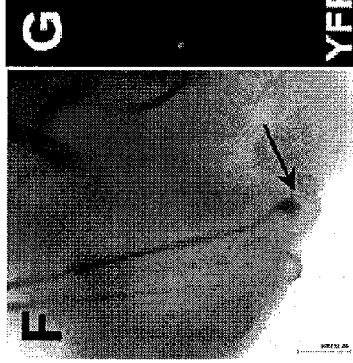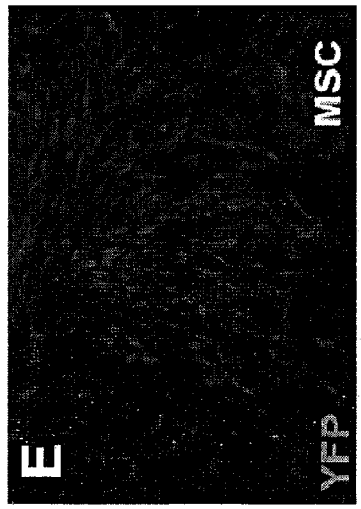

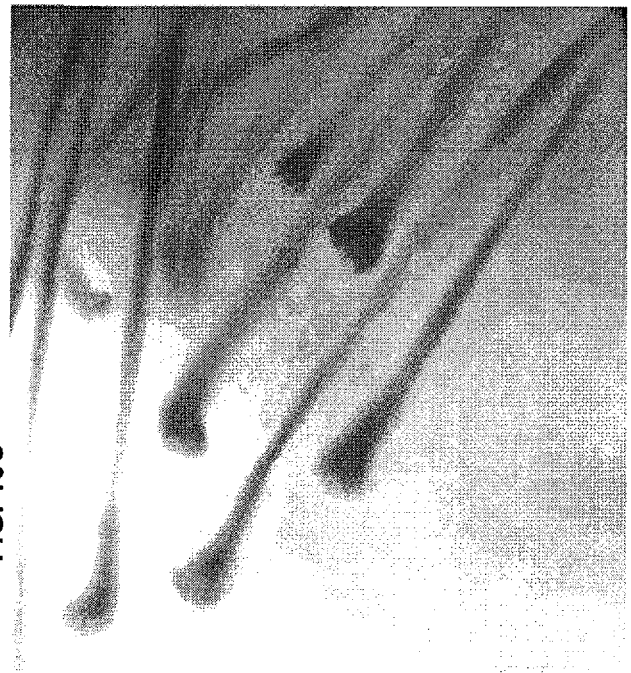
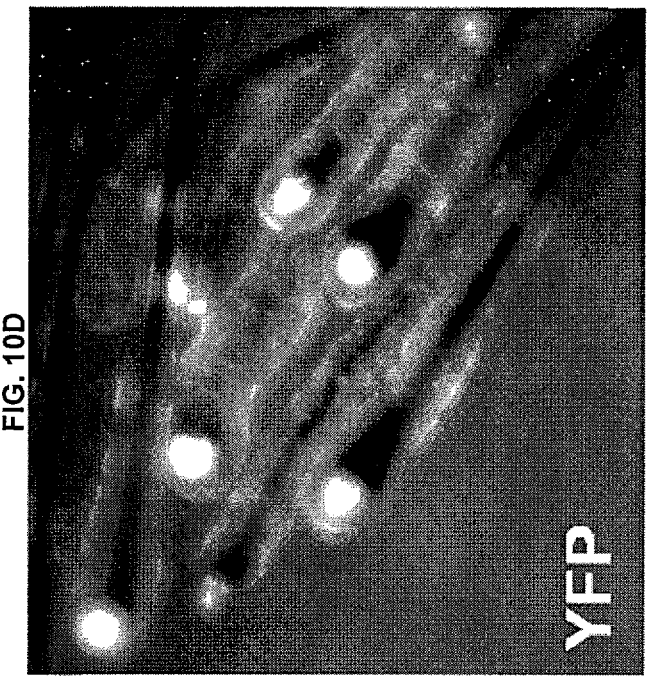

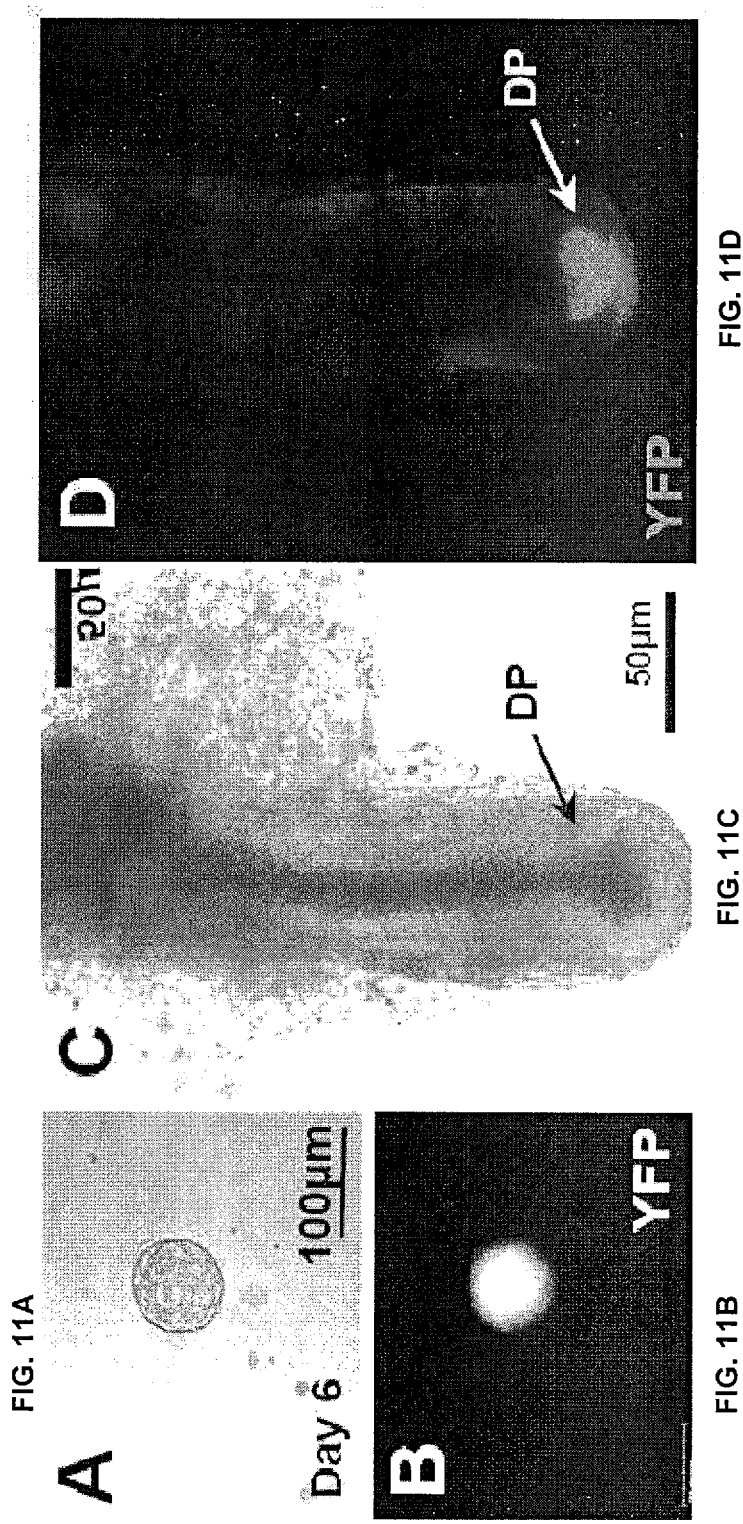

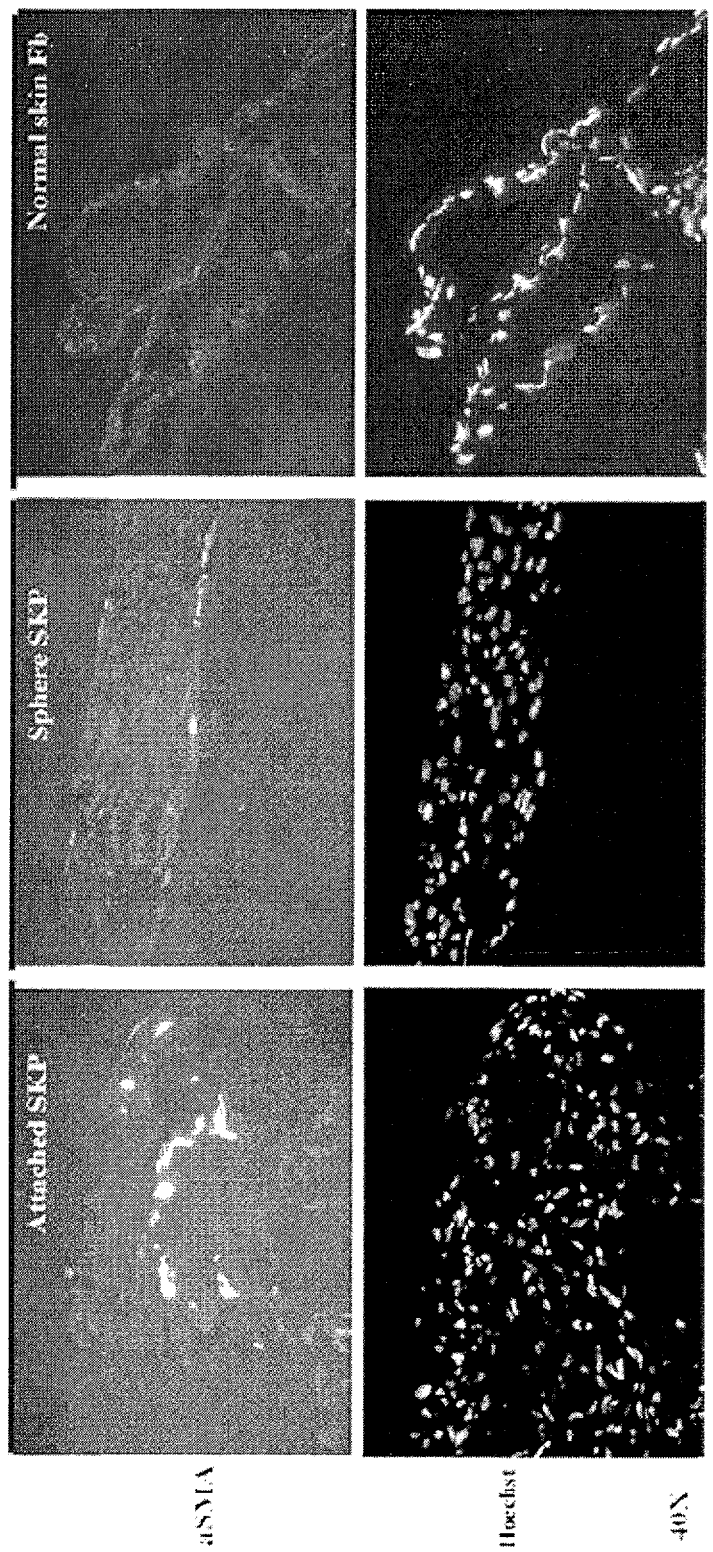
FIG. 15 con't.

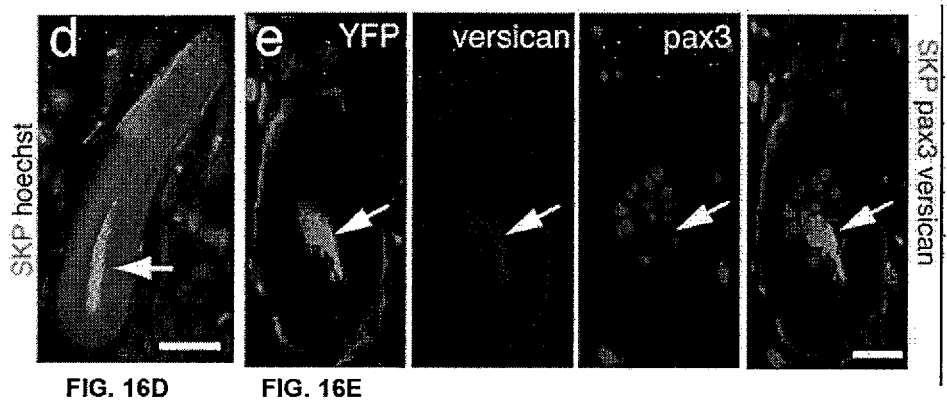
FIG. 16D  FIG. 16E
FIG. 16F
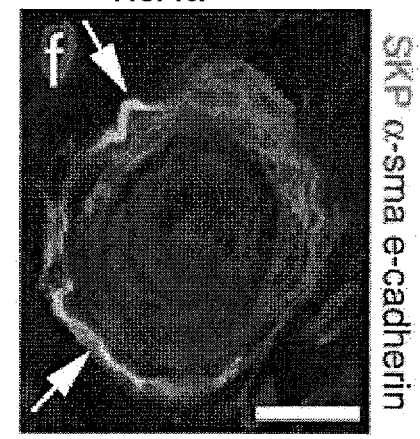
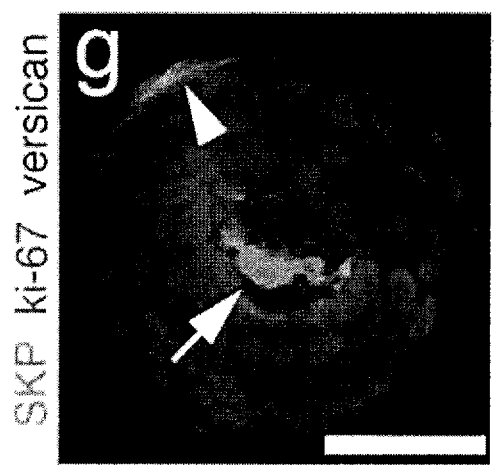
FIG. 16G

FIG. 16H
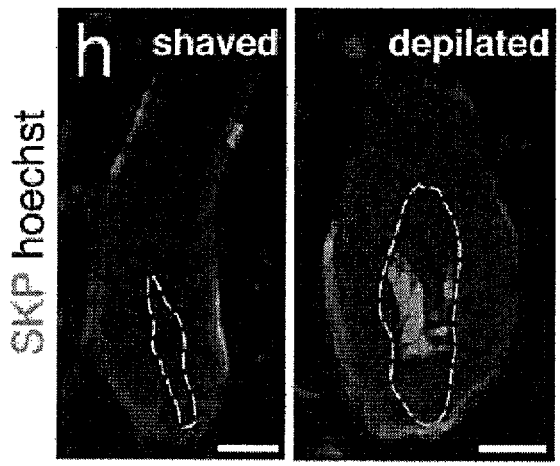
FIG. 16I     FIG. 16J
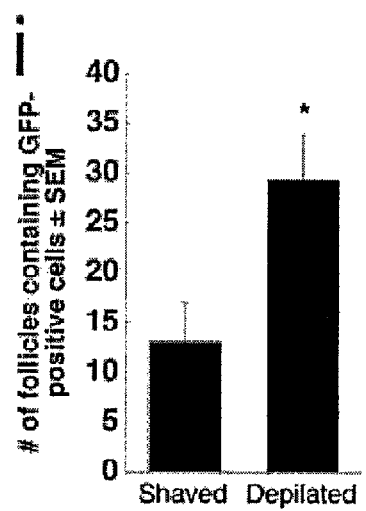 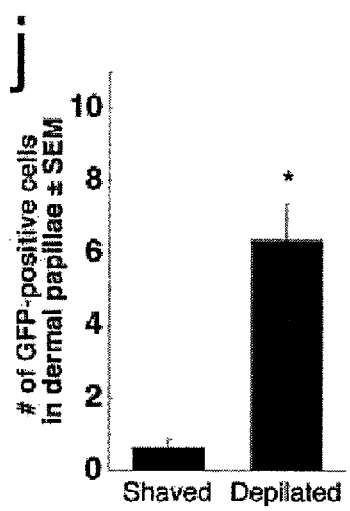
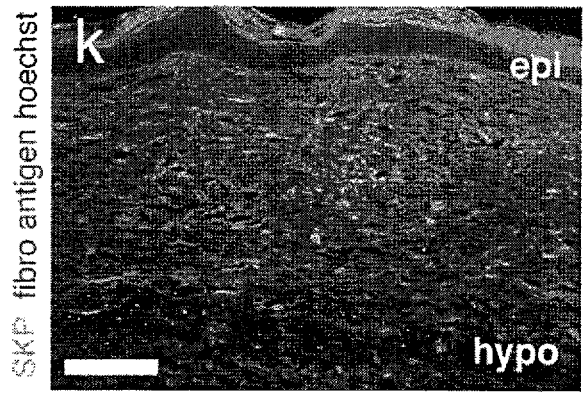
FIG. 16K

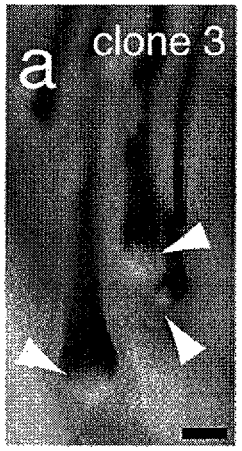 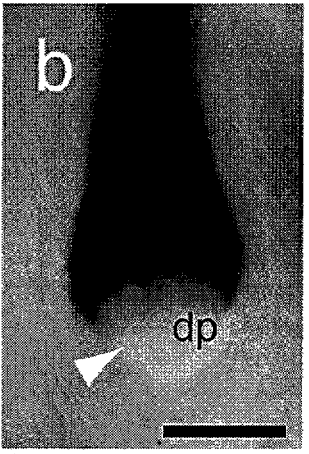 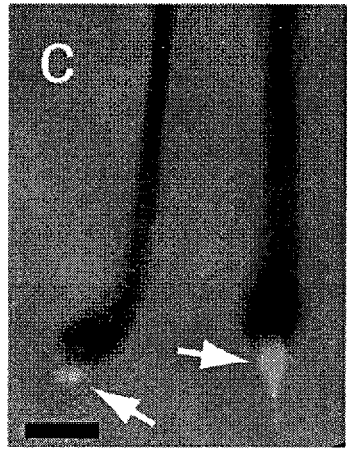
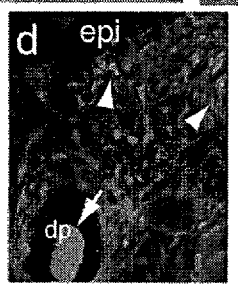
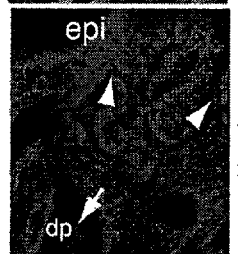
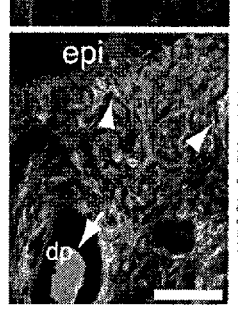
FIG. 18A  FIG. 18B  FIG. 18C
FIG. 18D FIG. 18I
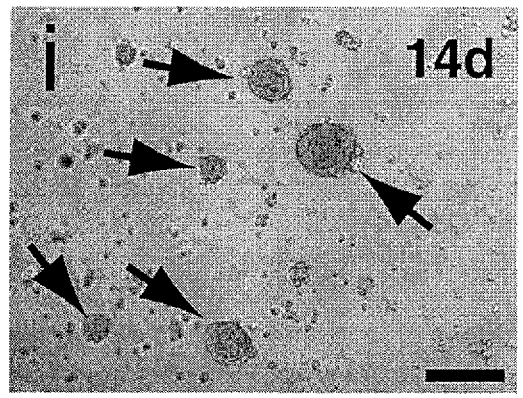
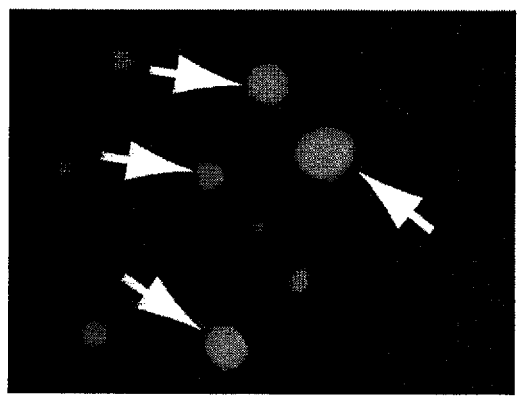
FIG. 18J
FIG. 18K
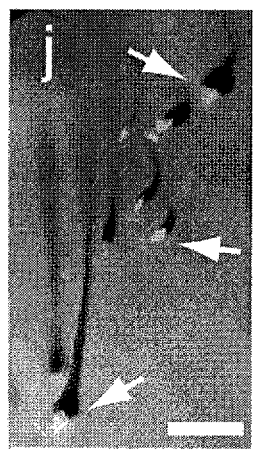
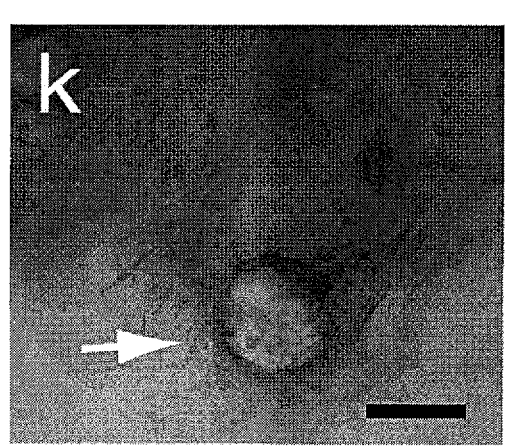

FIG. 19D oil red O
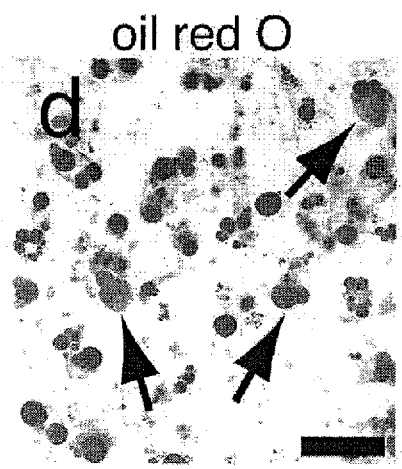
FIG. 19E α-sma hoechst
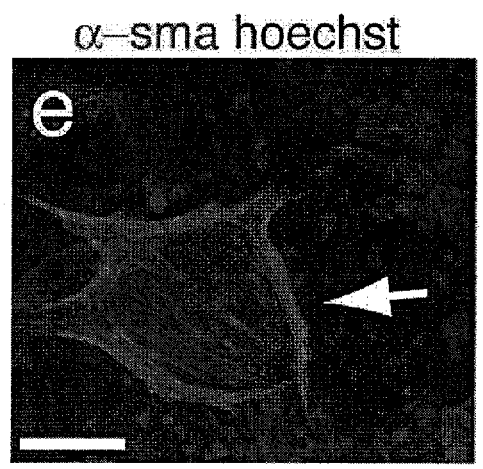
FIG. 19F nestin hoechst
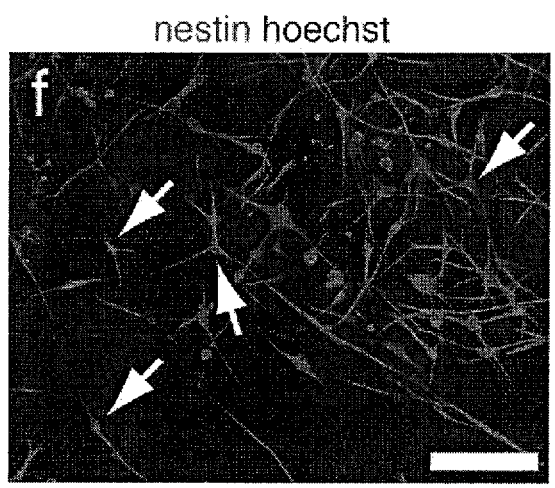
FIG. 19G β-tubulin hoechst
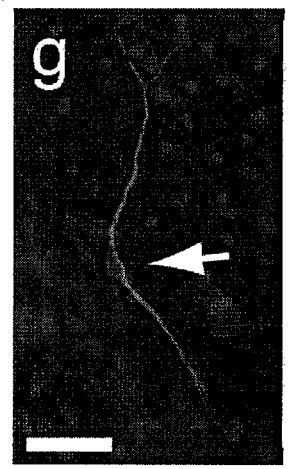

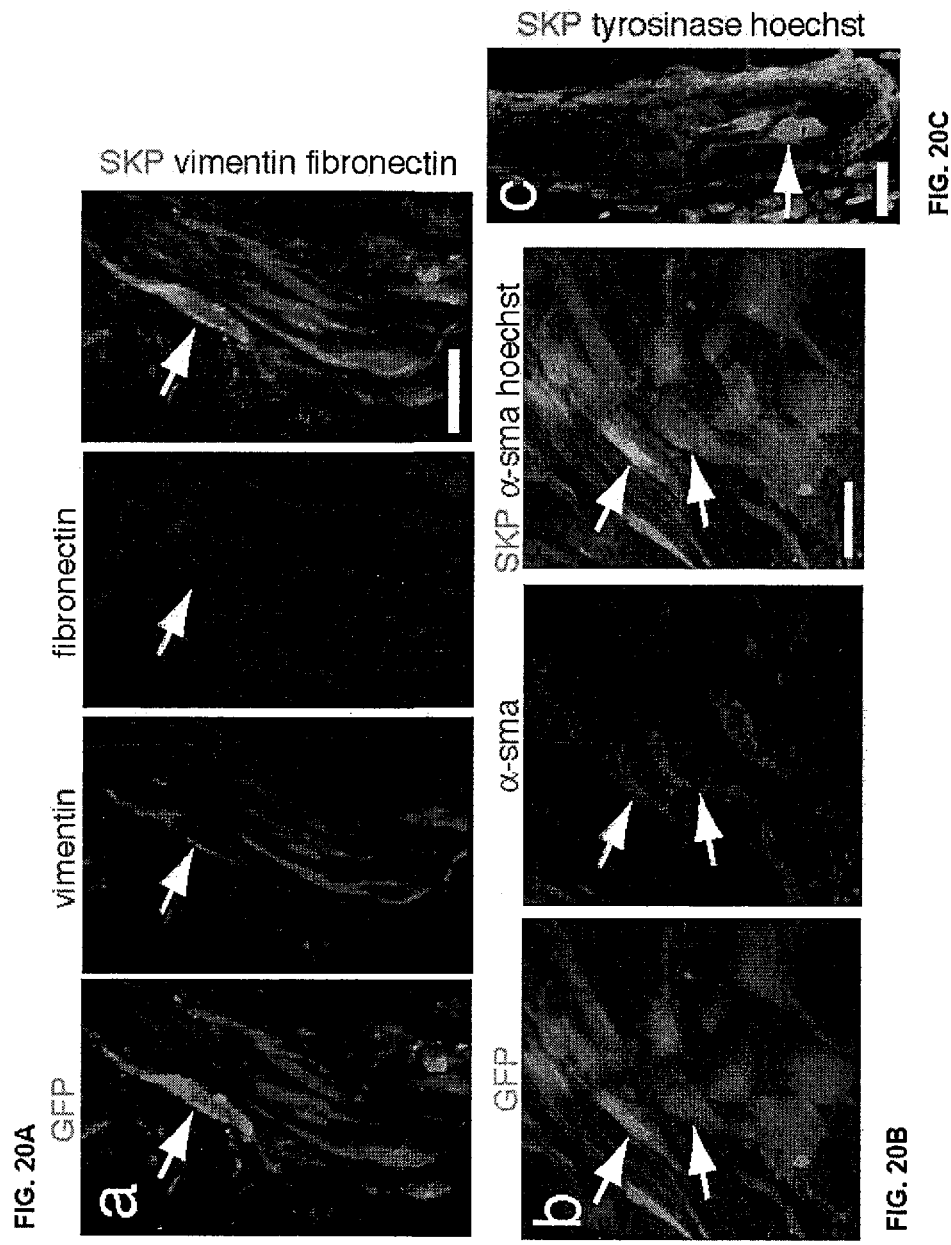

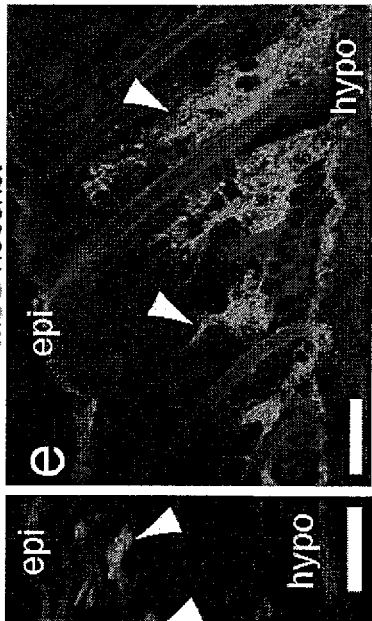
FIG. 20D
FIG. 20E
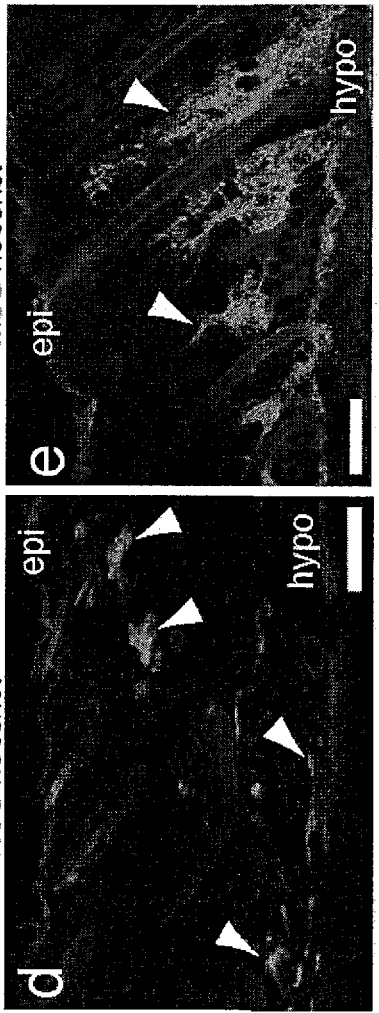
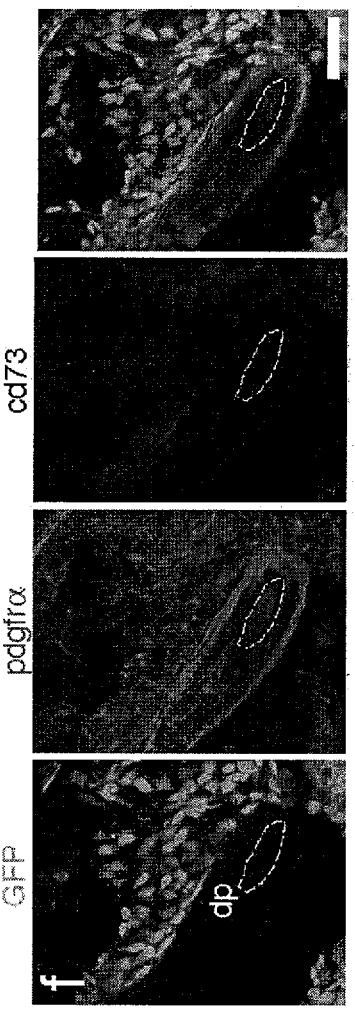
FIG. 20F

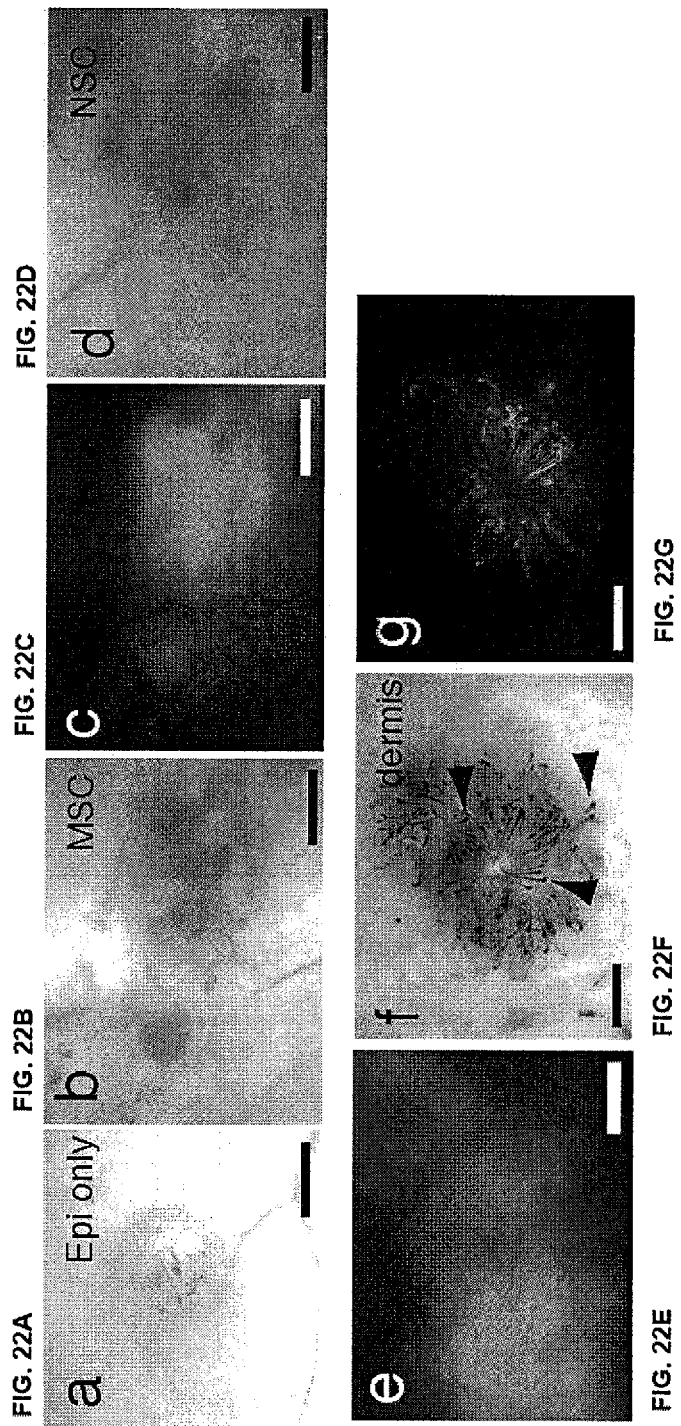

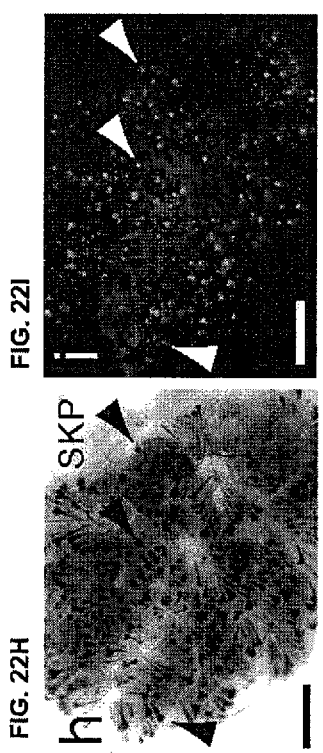
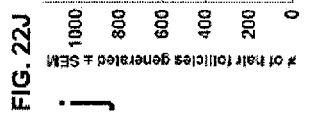
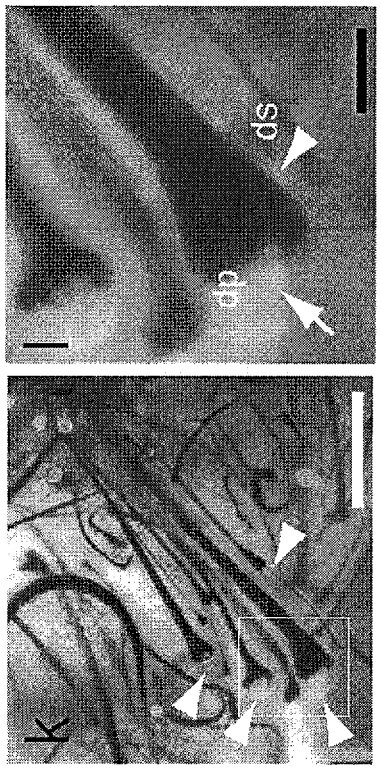
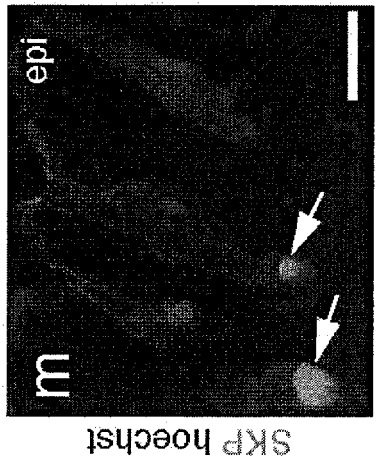
FIG. 22H FIG. 22I FIG. 22J FIG. 22K FIG. 22L FIG. 22M

US 8,617,882 B2

SKIN-DERIVED PRECURSOR CELLS AND USES THEREOF

CROSS-REFERENCE TO RELATED APPLICATIONS

This application is the national stage of International Application No. PCT/CA2008/001104, filed Jun. 6, 2008, which claims the benefit of U.S. Provisional Application No. 60/934,419, filed Jun. 13, 2007, and, 60/933,302, filed Jun. 6, 2007, each of which is hereby incorporated by reference.

BACKGROUND OF THE INVENTION

The invention relates to skin-derived precursor (SKP) cells, and method of using such cells.

While adult mammalian stem cells were previously thought only to differentiate into cells of their tissue of origin, a number of recent reports have identified cultured adult stem cells that show a surprisingly diverse differentiation repertoire. Although at least some reports of multipotency are due to unanticipated cellular fusion events that occurred in vivo, compelling evidence still exists for the multipotency of a number of cultured adult stem cell populations. Perhaps the most striking examples of this multipotency derive from blastocyst injection studies, where both multipotent adult progenitor cells were isolated following long-term culture of bone marrow cells and neural stem cells from the central nervous system contributed to many different developing tissues.

We have previously identified one such multipotent precursor cell population from adult mammalian dermis. These cells, termed SKPs for skin-derived precursors, can be isolated and expanded from rodent and human skin, and differentiate into both neural and mesodermal progeny, including into cell types that are never found in skin, such as neurons.

SUMMARY OF THE INVENTION

In a first aspect, the invention features a method for inducing hair follicle formation in a mammal. The method includes introducing a composition including skin derived precursors (SKPs) and keratinocytes into the skin of the mammal to induce hair follicle formation. In some embodiments, at least 5%, 10%, 20%, 30%, 40%, 50%, 60%, 70%, 80%, 90%, 95%, 99%, or even 100% of the cells in the composition are SKPs and keratinocytes. The ratio of SKPs to keratinocytes in the composition may be at least 1:1,000, 1:100, 1:50, 1:20, 1:10, 1:5, 1:4, 1:3, 1:2, 1:1, 2:1, 3:1, 4:1, 5:1, 10:1, 20:1, 50:1, 100:1, or 1,000:1. The method may further include isolating SKPs from the new hair follicles produced by introducing the composition; and re-introducing the newly isolated SKPs and keratinocytes into the skin of the mammal.

In a related aspect, the invention features another method for inducing hair follicle formation in a mammal. This method includes the steps of (a) providing a first cellular composition where at least 5% (e.g., at least 10%, 20%, 30%, 40%, 50%, 60%, 70%, 80%, 90%, 95%, 99%, or even 100%) of the cells are SKPs; (b) providing a second cellular composition where at least 5% (e.g., at least 10%, 20%, 30%, 40%, 50%, 60%, 70%, 80%, 90%, 95%, 99%, or even 100%) of the cells are keratinocytes; and (c) co-transplanting the first and second compositions into the skin of the mammal, thereby inducing hair follicle formation. The method may further include the steps of: (d) isolating SKPs from the hair follicles produced by step (c); and (e) co-transplanting the isolated SKPs of step (d) and keratinocytes into the skin of the mammal.

In either of the above two aspects, the mammal may be a human. The method may be performed in conjunction with treating a skin wound (e.g., a burn, an ulcer, an infection, or a physical injury). In some embodiments, the mammal may be suffering from alopecia (e.g., due to cancer therapy such as chemotherapy or radiation therapy), male pattern baldness, or female pattern baldness.

The invention also features a method for inducing hair follicle formation in a mammal (e.g., a human) including the steps of (a) isolating SKPs from the mammal; (b) providing keratinocytes; (c) optionally culturing the SKPs; and (c) co-transplanting the SKPs and the keratinocytes into the mammal, thereby inducing hair follicle formation. The method may be performed in conjunction with treating a skin wound (e.g., a burn, an ulcer, an infection, or a physical injury). The mammal may be suffering from alopecia (e.g., due to a cancer therapy such as chemotherapy or radiation therapy), male pattern baldness, or female pattern baldness.

The invention also features a composition that includes SKPs and keratinocytes. In some embodiments the SKPs and the keratinocytes include at least 5% (e.g., at least 10%, 20%, 30%, 40%, 50%, 60%, 70%, 80%, 90%, 95%, 99%, or even 100%) of the cells of the composition and the ratio of SKPs to keratinocytes is between 1:1,000, 1:100, 1:50, 1:20, 1:10, 1:5, 1:4, 1:3, 1:2, 1:1, 2:1, 3:1, 4:1, 5:1, 10:1, 20:1, 50:1, 100:1, or 1,000:1. The composition may further include additional cell types (e.g., stromal cells, adipocytes) or may include a pharmaceutically acceptable carrier (e.g., suitable for intradermal administration). The invention also features kits including a composition comprising SKPs and keratinocytes and instructions for use (e.g., for any of the indications disclosed herein).

The invention also features kits that include a first composition containing SKPs; a second composition containing keratinocytes, and instructions for use. Each composition may include 10, 100, 1,000, 10,000, 100,000, 1,000,000 SKPs or keratinocytes, respectively. The cells of each composition may be at least (e.g., at least 10%, 20%, 30%, 40%, 50%, 60%, 70%, 80%, 90%, 95%, 99%, or even 100%) SKPs or keratinocytes, respectively.

The invention also features a method of generating a dermal sheet by culturing SKPs (e.g., human SKPs) under conditions which permit formation of a dermal sheet. The culture may include a surface capable of adhering to the SKPs (e.g., a surface coated with poly-d-lysine and laminin). The method may further include overlaying a sheet of epidermal cells onto the dermal sheet.

The dermal sheets of the present invention may be administered (e.g., applied to the skin) to a mammal to regenerate skin. The mammal may have a burn or an ulcer, may have or previously had an infection resulting in skin loss, may have undergone a surgical procedure requiring skin regeneration, or may have an injury resulting in skin loss. The mammal, alternatively or in addition to these conditions, may be receiving the dermal sheet for cosmetic purposes.

The invention also features a dermal sheet produced by a method described herein. The dermal sheet may include human cells and may be capable of being grafted onto a mammal. The dermal sheet may further include a scaffold or a matrix (e.g., any material described herein). The scaffold or matrix may be bioabsorable, biodegradable, or non-bioabsorbable.

By "skin derived precursors" or "SKPs" is meant a multi-potent stem cell with at least some of the following characteristics. SKPs can generate floating spherical colonies when grown in the presence of FGF2 (fibroblast growth factor) and EGF (epidermal growth factor). The SKP spheres express specific markers including Sox2, fibronectin, nestin, vimentin, and versican and may also express the p75 receptor and platelet derived growth factor receptor alpha. SKPs can be derived from the dermal components of the skin and hair follicles (e.g., the dermal papilla of hair follicles) from neonatal, infant, and adult mammals. SKPs also include cultured stem cells whose ancestors were derived from multipotent stem cells naturally found in the skin or hair follicles. These cells are described in detail, for example, in U.S. Patent Application Publication Nos. 2002/0016002, 2002/0123143, and 2003/0003574, hereby incorporated by reference. SKPs are typically capable of differentiating into both neural and mesodermal cell types, including neurons, catecholaminergic neurons, Schwann cells, glia, smooth muscle cells, and adipocytes.

By a "population of cells" is meant a collection of at least ten cells. In some embodiments, the population consists of at least twenty cells, at least one hundred cells, at least one thousand, or even one million cells. Because the SKPs of the present invention exhibit a capacity for self-renewal, they can be expanded in culture to produce populations of even billions of cells.

A "mammal" may be either a human or a non-human (e.g., rat, mouse, pig, and dog) mammal.

By "scaffold" or "matrix" is meant a structural element. A scaffold or matrix may include structural proteins (e.g., collagen and gelatin), carbohydrates or polysaccharides (e.g., cellulose, dextran, alginate, and chitosan), polymers (e.g., polyamide, polyester, polystyrene, polypropylene, polyacrylate, polyvinyl, polycarbonate, polytetrafluorethylene, and dextran), fibers (e.g., cotton), foams, or nitrocellulose compounds. Other exemplary scaffold and matrix materials useful in the invention are described herein.

By "bioabsorbable" is meant a material that is capable of being degraded by the body.

Other features and advantages of the invention will be apparent from the following Detailed Description, the drawings, and the claims.

BRIEF DESCRIPTION OF THE DRAWINGS

FIG. 2A shows SKPs survive and migrate throughout the interfollicular dermis, as well as into dermis-derived components of the hair follicle (i.e., dermal papillae and dermal sheath). Transplanted SKPs never generate or migrate into the epidermis or the epidermal derivatives of hair follicle. FIG. 2B is a higher magnification image of SKPs within the dermal papillae of a hair follicle (arrow). Within the dermis, SKPs appear to have differentiated into dermal fibroblasts and adipocytes (arrowhead) within the lower dermis/hypodermis.

FIG. 3A shows that three weeks following transplant, SKPs have migrated and seemingly completely repopulated the dermal papillae of a hair follicle, possibly inducing formation of a new follicle. FIG. 3B shows SKPs within the papillae express versican, a marker specific to the follicular dermal papillae cells. FIG. 3C shows that transplanted SKPs can also be observed within the dermal sheath, a specialized layer of cells surrounding the hair bulb that are thought to be in continuous cellular exchange with the dermal papillae. FIG. 3D shows that cells within the sheath also undergo cell division (ki67-positive) suggesting they are able to respond to endogenous cues within the niche.

FIGS. 5A-5E are images showing that SKPs contribute to formation of new hair follicles surrounding a wound. FIG. 5A is a diagram illustrating phenotypic stages of hair follicle formation. FIG. 5B is a low magnification image showing wound a putative immature follicle at the perimeter of the wound three weeks post-lesion and transplant. FIG. 5C is a high magnification image of boxed region in FIG. 5B, illustrating the immature follicular phenotype and the integration of transplanted SKPs surrounding the follicle, as well as within the dermal papillae. FIG. 5D depicts another example of a confocal optical section depicting colocalization of transplanted SKPs with versican-positive dermal papillae cells of the immature follicle. Pan-cytokeratin staining (red) of epidermal keratinocyte is not expressed by transplanted SKPs, further demonstrating their restriction to dermis-derived structures within the follicle. FIG. 5E depicts another example of an immature follicle containing transplanted SKPs expressing p75NTR, which is enriched within anagen phase follicular dermal papillae. The occurrence of these 'immature follicles' was typically only observed within the regions containing transplanted SKPs.

FIGS. 6A-6D are images showing that SKPs integrating into the dermal papillae of existing hair follicles are functional. FIGS. 6A and 6B show that rat SKPs have integrated into dermal papillae of existing hair follicles or induced formation of new hair follicles within normal mouse backskin. FIGS. 6C and 6D show that, after six weeks, follicles containing SKP-derived dermal papillae generate longer and thicker hair (arrow), suggesting that SKPs retain inductive capacity, and retain regulatory properties specific to the donor (rat).

FIGS. 8A-8D are images showing that SKPs induce de novo hair follicle formation. FIG. 8A shows a brightfield image of hair new hair follicles within the backskin of a hairless mouse. FIG. 8B shows that three weeks after combination with dissociated newborn skin cells, E17 SKPs can be seen comprising the entire dermal papillae and as well as in the dermal sheath of new hair follicles. FIGS. 8C and 8D are high magnification images of SKP-derived hair follicles.

FIG. 8E is a graph showing the number of new hair follicles generated upon transplantation of SKPs and keratinocytes.

FIGS. 9A-9G are images showing that adult SKPs participate in new hair formation. FIG. 9A shows that, following the same assay as described above, adult (8 weeks old) SKPs combined with newborn skin cells were found comprising entire dermal papillae and dermal sheath of the majority of new hair follicles that had been generated within the graft. FIG. 9B shows that GFP fluorescence indicating location of GFP-labeled SKPs within the follicle. FIGS. 9C and 9D show another example of a newly generated hair follicle showing SKPs within the dermal papillae. Mesenchymal stem cells in vitro (FIG. 9E) expressing GFP, do not participate in hair follicle formation when grafted in the same hair formation assay (FIGS. 9F and 9G) suggesting that the inductive properties are unique to SKPs.

FIGS. 10A-10D show that clonally-derived adult SKP are capable of generating new hair follicles. Secondary clonal SKPs spheres were generated at a density of 1000 cells/ml. A single clonal sphere was isolated, dissociated and expanded to generate large numbers of tertiary clones. Each skin graft containing a single clonal population of adult SKPs (combined with newborn epidermal cells) gave rise to clusters of new hair follicles (FIG. 10A) which contained GFP-expressing SKPs clones within the dermal papillae and dermal sheath. FIG. 10B shows YFP labeling. FIGS. 10C and 10D are higher magnification images of new clonal SKP-derived hair follicles.

FIGS. 11A-11F are images showing transplanted SKPs within the follicular dermal papillae niche, retain self renewal and multipotency. Dissociation of new hair follicles containing GFP-labeled SKP-derived dermal papillae, retain their ability to self renew, generating clonal spherical colonies (FIG. 11A) after 7-14 days following exposure to fibroblast growth factor and epidermal growth factor. FIG. 11B shows that same sphere showing expression of GFP to confirm that the sphere originated from a cell which had been transplanted into the skin and generated a new hair follicle 4 weeks prior. FIGS. 11C and 11D show that these re-cultured spheres also retain multipotency such that they still retain the ability to stimulate formation of hair follicles in vivo, as well as to generate neurons in vitro which express nestin (red, arrows; FIG. 11E) and beta III tubulin (red; arrows; FIG. 11F) a marker specific to neurons.

FIG. 13C shows that, within the wound, SKPs differentiate into putative dermal fibroblasts immunostaining for fibronectin (arrows) and myofibroblasts staining with alpha-smooth muscle actin (arrowheads).

FIGS. 16A-16M is a set of images showing that SKPs regenerate the dermis and home back to a hair follicle niche upon transplantation. FIG. 16A shows back skin transplanted with dissociated YFP-tagged neonatal mouse SKPs two weeks earlier. Transplanted cells (lighter color) are in the interfollicular dermis (arrows) and the dermal papilla (DP) and dermal sheath DS (arrowhead) of hair follicles. FIGS. 16B and 16C show dermis transplanted with SKPs as in FIG. 16A, and immunostained for GFP (left panel) and two dermal fibroblast markers, PDGFRα (FIG. 16B, center panel) and collagen type 1 (FIG. 16C, center panel). Right panels of FIGS. 16B and 16C are merges, with the arrows indicate double-labeled cells. FIGS. 16D-16G show hair follicles containing YFP-positive SKPs 2-4 weeks post-transplantation, as in FIG. 16A. FIG. 16D shows a hair follicle with the DP (arrow) comprised entirely of YFP-labeled cells. FIG. 16E shows a follicle triple-labeled for YFP (left panel), versican (a marker of DP; center-left panel) and pax3 (a melanocyte/melanoblast marker; center-right panel). The right panel is a merge, and arrow indicates the DP. FIG. 16F shows a follicle cross section which shows transplanted cells in the DS (arrows) expressing α-sma but not e-cadherin (an epidermal marker). FIG. 16G shows transplanted cells within the DS (arrowhead) but not DP (arrow) expressed the proliferation marker Ki67. FIGS. 16H-16J show quantification of the number of YFP-positive cells associated with follicles (FIG. 16I) or present within the DP of individual follicles (FIG. 16J; hatched lines in FIG. 16H) following transplantation into depilated versus shaved skin. ($p<0.05$ for FIGS. 16I and 16J). FIGS. 16K-16M show skin four weeks following transplantation of neonatal mouse SKPs adjacent to a punch wound. Transplanted cells repopulated the wound, and express fibroblast-specific antigen (FIGS. 16K and 16L, arrows), fibronectin (FIG. 16M), and α-SMA (FIG. 16M, arrowhead). Scale bars=200 μm (16A), 16 μm (16B, 16C), 50 μm (16D, 16H, 16L), 25 μm (16E, 16F, 16G, 16M), 100 μm (16K). epi=epidermis, hypo=hypodermis. Some sections were counterstained with Hoechst 33258 or fluorescent Nissl to show tissue morphology, as indicated.

FIGS. 17A and 17B show skin four weeks after transplantation of neonatal mouse YFP-tagged SKPs adjacent to a punch wound. Transplanted cells (green) are present in "peg-like" hair follicles (FIG. 17A, arrowheads), in DP and DS (FIG. 17B, arrow and arrowheads). Those in the DP express versican (FIG. 17B, top right panel). The bottom panel in 17B is a merge. FIGS. 17C-17E show patches formed by mixing GFP-tagged dissociated adult rat SKPs with newborn C57/Bl6 epidermal aggregates, showing that the DP and DS (FIGS. 17C and 17D; arrow and arrowheads) were comprised of SKPs. Quantification of follicles with GFP-positive DP (FIG. 17E) revealed that rat SKPs were enriched in follicle inductive ability relative to newborn dermal cells ($10^5$ cells n=3; $10^6$ cells n=2, *p=0.001). FIGS. 17F and 17G show adult mouse skin transplanted 8 weeks earlier with GFP-tagged adult rat SKPs. Transplanted cells contributed extensively to the dermis, and the DP of hair follicles (FIG. 17F, arrows), many of which were in anagen (FIG. 17G, arrows). FIGS. 17H and 17I show that chimeric rat/mouse hairs were thicker (FIG. 17H) and longer (FIG. 17I) than endogenous pelage hairs. FIG. 17J shows patch assays with murine dermal cells versus rat SKPs. FIG. 17K is graph showing that hairs induced by rat SKPs had larger bulbs (n=2 experiments, *p=0.0074). Tissue was counterstained with Hoechst 33258 (17A), fluorescent Niss1 stain (17F), or propidium iodide (17G) to show tissue morphology. Scale bars=100 µm (17A, 17F, 17J), 50 µm (17B, 17D, 17G) and 500 µm (17C). epi=epidermis, hypo=hypodermis.

FIGS. 18A-18F are images showing that clonally-derived SKPs reconstitute the dermis and induce hair follicle formation. FIGS. 18A and 18B show one adult rat GFP-positive SKPs clone (clone 3) that was expanded for 12 weeks and was used in follicle patch assays. FIG. 18D-18F show clone 3 transplanted into the adult mouse dermis. FIG. 18A-18C show that clonal SKPs comprised the DP (arrowheads) of newly-formed hair follicles after 2-4 months (18A and 18B) or 11 (18C) months in culture. FIGS. 18D-18F show that transplanted cells (green) homed to hair follicle DP (18D, arrow) and integrated into interfollicular dermis (18D, arrowheads), where they expressed fibronectin (18D, center panel), vimentin (18E), and α-sma (18F) 3 weeks post-transplant.

FIGS. 18G-18K show that SKPs isolated from their hair follicle niche self-renew and serially reconstitute hair follicles. FIG. 18G is a schematic showing the serial reconstitution assay of hair growth. FIG. 18H shows a single hair follicle containing adult rat GFP-labeled cells within the DP and DS dissected from a patch assay graft. FIG. 18I shows that cells, isolated from follicles as in FIG. 18H, generated GFP-positive SKP spheres after 12 days of culture (arrows) as seen by phase (top panel) and fluorescence (bottom panel) illumination. FIG. 18J shows that cells from these spheres generated secondary hair follicles in the patch assay (arrows). FIG. 18K shows that, in tertiary follicle reconstitutions, GFP-labeled SKPs were surrounded by black melanocytes (arrow), but did not induce hair follicle formation. Scale bars=100 µm (18A-18D, 18J), 25 µm (18E, 18F), 50 µm (18H), 200 µm (18J), 250 µm (18K).

FIGS. 19A-19L are a set of images and a graph showing that SKPs isolated from the hair follicle niche remain multipotent. FIGS. 19A-19C show that skin transplanted with GFP-positive follicle-derived SKPs for 4 weeks. In FIG. 19A, transplanted cells (green) are seen to home back to the DS and DP of hair follicles (arrows) and reconstituted the dermis (arrowheads). FIGS. 19B and 19C show that they expressed the dermal fibroblast markers PDGFRα and collagen type 1. Right panels are the merges, and arrows indicate double-labelled cells. FIGS. 19D and 19E show that, when differentiated in culture under mesodermal conditions, follicle-derived SKPs generated adipocytes, as indicated by the lipophilic dye oil red O (19D, arrows), and α-sma-positive cells, potentially myofibroblasts (19E, arrow). FIGS. 19F and 19G show that, when differentiated under neurogenic conditions, they generated nestin-positive cells after 5 days (19F, arrows), and morphologically-complex, βIII-tubulin positive cells after 14 days (19G, arrow). FIGS. 19H and 19I show sciatic nerve sections 6 weeks following crush and transplantation, showing that follicle-derived SKPs generated cells positive for the Schwann cell markers p75NTR (19H) and P0 (19I), as did the endogenous Schwann cells. FIGS. 19J-19L show transplantation of follicle-derived SKPs into the chick neural crest migratory stream (stage 18). After 8 days in ovo, some of the transplanted cells that had migrated to the dermis (FIGS. 19J and 19K, green) were versican-positive (FIG. 19K, arrows). Quantification after 3 days in ovo (FIG. 19L) demonstrated follicle-derived (6 transplants) and clonal (8 transplants) SKPs behaved like total SKPs (9 transplants), migrating to the nerve or DRG and to the skin, with some remaining close to the neural tube. Samples were counterstained with Hoechst 33258, as indicated. epi=epidermis. Scale bars=200 µm (19A), 25 µm (19B, 19C, 19H, 19I), 50 µm (19D, 19E, 19G, 19J, 19M), 100 µm (19F).

FIGS. 20A-20F are photomicrographs showing that transplanted SKPs, but not NSCs or MSCs, home to a dermal papilla niche and generate dermal fibroblasts. FIG. 20A shows GFP-expressing adult rat SKPs transplanted into depilated adult NOD/SCID mouse dermis 21 days earlier, and immunostained for GFP (left), vimentin (center-left) and fibronectin (center right). The right panel is the merged image. The arrow denotes a transplanted cell expressing both vimentin and fibronectin. FIG. 20B shows analysis of transplants performed as in FIG. 20A, and immunostained for GFP (left) and α-sma (center). The right panel is the merged image. Arrows denote cells positive for both markers. FIG. 20C shows adult GFP-expressing rat SKPs transplanted into dermis as in FIG. 20A, immunostained for GFP to mark transplanted cells, and for the melanoblast/melanocyte marker tyrosinase. Arrow indicates transplanted cells that have homed to the DP, but that they do not express melanocyte markers. FIGS. 20D and 20E show backskin of NOD/SCID mice 21 days post-grafting, indicating that transplanted YFP-tagged neonatal mouse NSCs (FIG. 20D, arrowheads) display poor survival and are never observed associating with hair follicles, while GFP-tagged adult rat MSCs (FIG. 20E, arrowheads) were found within the interfollicular dermis but were never recruited into the DP of hair follicles. FIG. 20F is a photomicrograph of a hair follicle in a section similar to FIG. 20E, immunostained for GFP to identify the transplanted MSCs (left), PDGFRα (center left), and the MSC marker cd73 (center right), showing that MSCs are never found in the DP (denoted by dashed lines). Nuclei are stained with Hoechst 33258 in FIGS. 20B-20E. epi=epidermis, hypo=hypodermis. Scale bars are 16 µm (20A, 20B), 25 µm (20C), 200 µm (20D, 20E), 40 µm (20F).

FIG. 21A shows that, three weeks after transplantation of neonatal YFP-tagged murine SKPs into the cavity and within the intact tissue surrounding a backskin punch wound (arrows denote the location of the transplant), transplanted cells are found within the regenerated tissue filling the wound cavity and scar (denoted by dashed lines). FIG. 21B-21D are photomicrographs of skin sections transplanted with YFP neonatal mouse SKPs into the intact tissue surrounding a wound immunostained for GFP, the DP marker versican (FIG. 21B), and the dermal fibroblast markers vimentin (FIG. 21C), or collagen type 1 (FIG. 21D). Transplanted interfollicular cells express dermal fibroblast markers (FIGS. 21C-21D, arrows), but do not express versican (FIG. 21B, arrowheads), although transplanted cells within the DP do express this marker (for example, see FIG. 16E). Nuclei are stained with Hoechst 33258 (blue) in FIGS. 21B-21D. epi=epidermis. Scale bars are 200 µm (21A), 50 µm (21B-21D).

FIGS. 22A-22M are a set of photomicrographs and a graph showing that SKPs, but not NSCs or MSCs, instruct epidermal cells to generate hair follicles. FIGS. 22A-22I are photomicrographs of patch assays at 12 days. Newborn murine epidermal aggregates alone do not generate hair follicles (FIG. 22A), and neither GFP-tagged rat MSCs (FIGS. 22B and 22C) nor YFP-tagged neonatal mouse NSCs (FIGS. 22D and 22E) induced follicle formation when mixed with epidermal cells, as shown in phase (FIGS. 22B and 22D) and fluorescence (FIGS. 22C and 22E) images of the patches. In contrast, $10^6$ dissociated GFP-expressing neonatal rat dermal cells induced hair follicle formation when combined with epithelial aggregates as seen by phase (FIG. 22F) and fluorescence (FIG. 22G) illumination, as did $10^6$ adult GFP-tagged SKPs (FIGS. 22H and 22I) (arrowheads in FIGS. 22F and 22H show hair follicles, while those in FIG. 22I show GFP-positive DPs). Note that in FIG. 22G several GFP follicles are entirely green due to contaminating GFP-expressing epidermal cells in the dermal preparation. FIGS. 22J and 22K show quantification of total hair follicle numbers in patches similar to those shown in FIGS. 22A-22I, demonstrating that adult rat SKPs were enriched for follicle inductive ability relative to total neonatal dermal cells and to other stem cell populations such as MSCs and NSCs. In FIG. 22J, $10^6$ dissociated cells were mixed with 10,000 epidermal aggregates and all follicles were counted. * $p<0.001$ relative to epi only, ** $p<0.001$ relative to epi only and dermis. FIGS. 22K and 22L are photomicrographs of hair follicles in patch assays where $10^6$ adult GFP-tagged rat SKPs were mixed with $10^6$ dissociated total skin cells from newborn C57/B16 skin (epidermis and dermis), as shown with combined phase with coincident fluorescence illumination. In FIG. 22K, arrowheads indicate follicles with DP generated from GFP-positive SKPs. FIG. 22L shows higher magnification of the boxed area, and the DP and DS are denoted by an arrow and an arrowhead, respectively. In these experiments, more than 80% of hair follicles contained GFP-positive DP (arrowheads) suggesting that the rat SKPs had a competitive advantage over the endogenous murine inductive cells. FIG. 22M shows GFP-tagged adult rat SKPs were transplanted into adult NOD/SCID mouse skin, and analyzed 8 weeks later. Transplanted GFP-positive cells (green) comprised the DP of many hair follicles, including some in telogen (arrows). Scale bars are 1 mm (22A, 22F-22I), 500 µm (22B-22E), 250 µm (22K), 100 µm (22L, 22M).

FIG. 23A shows hair follicles in a patch assay where SKP clone 2 (generated from adult, GFP-tagged rat skin) was expanded 8 weeks in culture and then mixed with epidermal cells. The DP and DS of these hair follicles are comprised of SKP-derived cells. FIG. 23B shows high magnification photomicrograph of a skin section transplanted with GFP-tagged rat SKP clone 3 and immunostained for GFP (green) and fibronectin (blue). Scale bars are 200 µm (23A), 25 µm (23B).

FIGS. 29A and 29B show Sox2 expressing cells from P2 Sox2 GFP mice in backskin. Keratin 5 and hoecsht staining are also shown. FIG. 29B shows expression of Sox2 (top left), keratin 5 (top right), and versican (bottom left) in P2 backskin from Sox2GFP mice. A merge is also shown (bottom right). FIG. 29C shows expression of Sox2 (left) and keratin 5 (center) in whisker pad skin. A merge including Sox2, keratin5, and hoecsht is also shown (right). FIG. 29D shows that dissociated neonatal skin cells from the backskin (top left) and facial skin (bottom left) of Sox2GFP mice generate spherical colonies when grown in proliferation medium. Many of these colonies are Sox2GFP$^+$, as shown in the right-most images. FIG. 29E is a histogram showing that fractionated Sox2GFP$^+$ facial skin cells show a 5-fold enrichment, and backskin cells a two-fold enrichment, for sphere formation relative to total cells. FIG. 29F shows that Sox2GFP$^+$ cells are enriched in hair follicle formation, as compared to epidermal cells. FIG. 29G is a histogram showing that SoxGFP2$^+$ cells exhibit a 10-fold greater capacity for follicle formation relative to ungated cells or Sox2GFP$^-$ fraction. FIG. 29H shows that fractionated Sox2GFP$^+$ cells are multipotent, generating nestin-positive neural precursors (left and left center panels), which are not observed in the Sox2GFP$^-$ fraction (right center panel). Unfractionated cells also exhibit nestin-positive cell formation (right panel).

DETAILED DESCRIPTION

The present invention provides methods for generating de novo hair follicles in a mammal, compositions of SKPs and keratinocytes, dermal sheets grown in vitro, and methods of making and using such sheets to regenerate skin (e.g., in a mammal having a burn or an ulcer, having or previously having had an infection resulting in skin loss, having undergone a surgical procedure requiring skin regeneration, or having an injury resulting in skin loss). The methods of generating hair follicles can be used to treat conditions such as alopecia, male pattern baldness, or female pattern baldness. All methods can be used for cosmetic purposes, either in conjunction with or in addition to the conditions noted above.

SKP Cells and Culture Conditions

Figure 1:
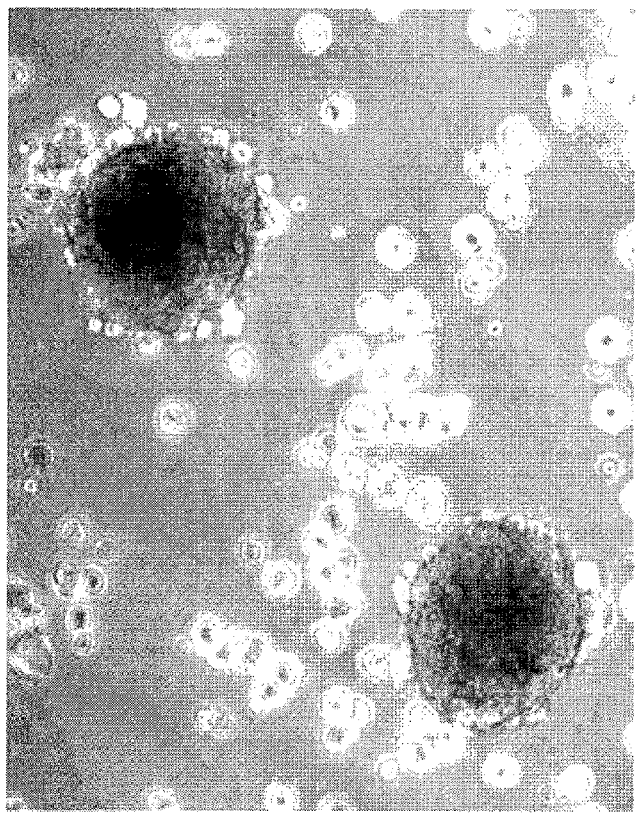
FIG. 1 is a set of photographs showing skin-derived precursors (SKPs) generated from rodent and human. Representative images of neonatal rodent and human SKPs following 3 weeks expansion in vitro are shown.
Figure 1:
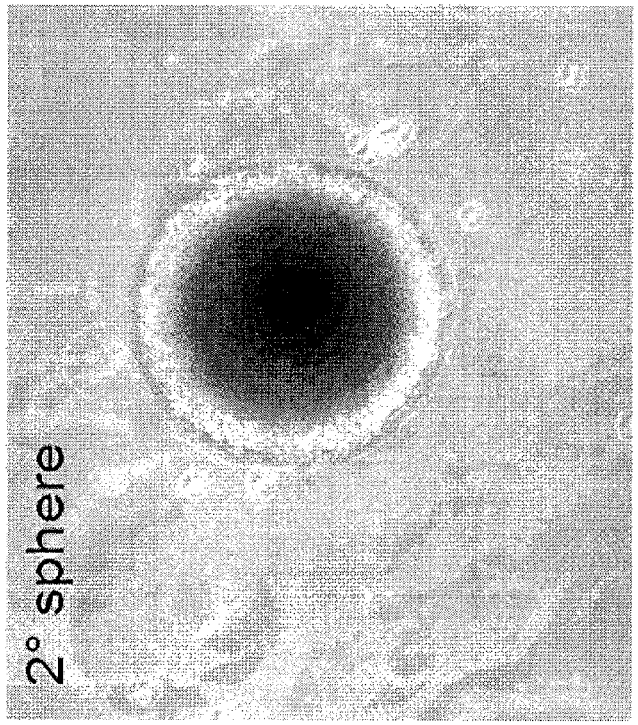

SKP cells have been described previously in PCT Publication Nos. WO 01/53461 and WO 03/010243, and WO 2005/071063, each of which is incorporated by reference. Rodent SKPs can be obtained, for example, from skin of mouse embryos (E15-E19), mouse, or rat neonates (postnatal day 2 (P2) to P6). In one method, the skin is cut into 2-3 mm$^2$ pieces. Tissue is digested with 0.1% trypsin or 1 mg/ml collagenase for 10-45 min at 37° C., mechanically dissociated, and filtered through a 40 µm cell strainer (Falcon, Franklin Lakes, N.J.). Cells are plated at a density of 1-2.5×10$^4$ cells/ml in DMEM/F-12 at 3:1 (Invitrogen, Carlsbad, Calif.), with 20 ng/ml epidermal growth factor (EGF) and 40 ng/ml FGF2 (both from Collaborative Research, Bedford, Mass.), hereafter referred to as proliferation medium. SKPs are then passaged by mechanically dissociating spheres and splitting one to three with 75% new medium and 25% conditioned medium. Clonal spheres are prepared as described previously (Fernandes et al. (2004) Nat. Cell Biol. 6:1082-93) and were differentiated similarly with the addition of 1% serum for the first three days (FIG. 1).

In the experiments described herein, human SKPs were isolated and cultured as follows. Pieces of human foreskin of 1-2 cm² deriving from voluntary circumcisions of children aged 4 weeks to 12 years of age were washed with Hanks' balanced salt solution (Invitrogen Corporation), cut into 4- to 6-mm pieces, washed again, and incubated in Liberase Blendzyme 1 (0.62 Wunsch U/ml; Roche Molecular Biochemicals, Laval, Quebec, Canada) overnight at 4° C. The epidermis was manually removed from each tissue piece, and the dermis was cut into 1-mm³ pieces and incubated in Liberase Blendzyme 1 for 30-40 minutes at 37° C. DNase I was added for 1 minute, and 10% fetal bovine serum (FBS) (Cambrex, Walkersville, Md.) was added to inhibit the enzymes. The supernatant was removed, and tissue pieces were resuspended in medium (Dulbecco's modified Eagle's medium (DMEM)/F12, 3:1 (Invitrogen) containing 1% penicillin/streptomycin unless otherwise indicated) and manually dissociated by pipetting into a 2-ml pipette, a process that was repeated until the tissue could be broken down no further. The cell suspension was then centrifuged at 1,000 rpm for 5 minutes and the supernatant removed, leaving the pellet and 3 ml of medium behind. The pellet was resuspended in the remaining medium using a fire-polished Pasteur pipette, and the suspension passed through a 70-μm cell strainer (BD Biosciences, Mississauga, Ontario, Canada). The strained cell suspension was then centrifuged, the medium removed, the pellet resuspended in 10 ml proliferation medium (DMEM-F12, 3:1 and 40 ng/ml FGF2, 20 ng/ml EGF (both from BD Biosciences), B27 (Invitrogen), and 1 μg/ml fungizone (Invitrogen)) and then transferred to a 25-cm² tissue culture flask (BD Biosciences).

For subculturing, medium containing SKPs growing in suspension was centrifuged at 1,000 rpm for 5 minutes and the supernatant was removed, leaving 6 ml of medium and the pellet behind. The pellet was resuspended in the remaining medium with a fire-polished Pasteur pipette, proliferation medium was added to a total of 20 ml, and the cell suspension was then split into two 25-cm² flasks. The cells were grown at 37° C. for an additional 2-3 weeks and then split again as above.

For immunocytochemical analysis of SKP spheres, 100 μl of medium containing suspended spheres was removed from a flask and spun down onto coated slides using a ThermoShandon Cytospin 4 apparatus (Thermo Shandon Inc., Pittsburgh, Pa.). The slides were then air-dried for 5 minutes and analyzed. For quantitation of the size of SKP spheres grown in different growth factors, the diameter of spheres was measured along both the x and y axes, because spheres were not uniformly spherical. The average of these two measurements was then used as the diameter of the sphere. Within a given experiment, multiple spheres were measured in each well, the mean diameter and SD of all measured spheres in each individual well were determined, and then four wells per experimental manipulation were considered to obtain a statistical comparison between growth factor treatments.

Human Epidermal Cells

Human epidermal cells (keratinocytes) can be obtained using any means known in the art. Specimens of split-thickness skin can be collected from donors (e.g., either live or cadavers). Alternatively, human keratinocyte cells are commercially available from vendors including ScienCell (Carlsbad, Calif.) and PromoCell (Heidelberg, Germany). Autologous keratinocytes can also be used.

Should it be necessary to culture keratinocytes, any culture technique known in the art may be used. One exemplary technique, the method described by Staiano-Coico et al. (1986) J. Clin. Invest. 77:396-404, is as follows. Cells are stored at 4° C., washed three times in MEM with antibiotics, then incubated in a solution of 0.5% trypsin (Difco laboratories, Detroit, Mich., 1:250) in $Ca^{2+}$ and $Mg^{2+}$ free phosphate-buffered saline (PBS; Gibco) for 90 mm at 37° C. Single-cell suspensions of epidermal cells are prepared by vigorous stirring in a solution of 0.25% DNase I; Sigma Chemical Co., St. Louis, Mo.) and 1% fetal bovine serum in PBS and filtered through sterile gauze; FBS was added to the cell suspensions to neutralize trypsin activity. After centrifugation and resuspension in complete culture medium (MEM, 20% fetal bovine serum, 2 mM L-glutamine, hydrocortisone (0.5 pg/ml), penicillin (100 U/ml), streptomycin (0.1 mg/ml, and fungizone (0.25 pg/ml)), the viability of epidermal cells prepared in this manner was determined to be 90-95% by trypan blue dye exclusion. Plastic tissue culture flasks containing $2\times10^5$ epidermal cells/cm² were incubated at 37° C. in a humid 95% air/5% $CO_2$ environment; the medium was changed every third day.

De Novo Generation of Hair Follicles

We have discovered that de novo hair follicle formation is induced when a combination of SKPs and epidermal keratinocytes are introduced into the skin of a mammal. Based on this discovery, the present invention provides methods of growing hair in by administration of a combination of SKPs and keratinocytes and pharmaceutical compositions comprising SKPs and keratinocytes (e.g., in a pharmaceutically acceptable carrier).

Figures 2A, 2B:
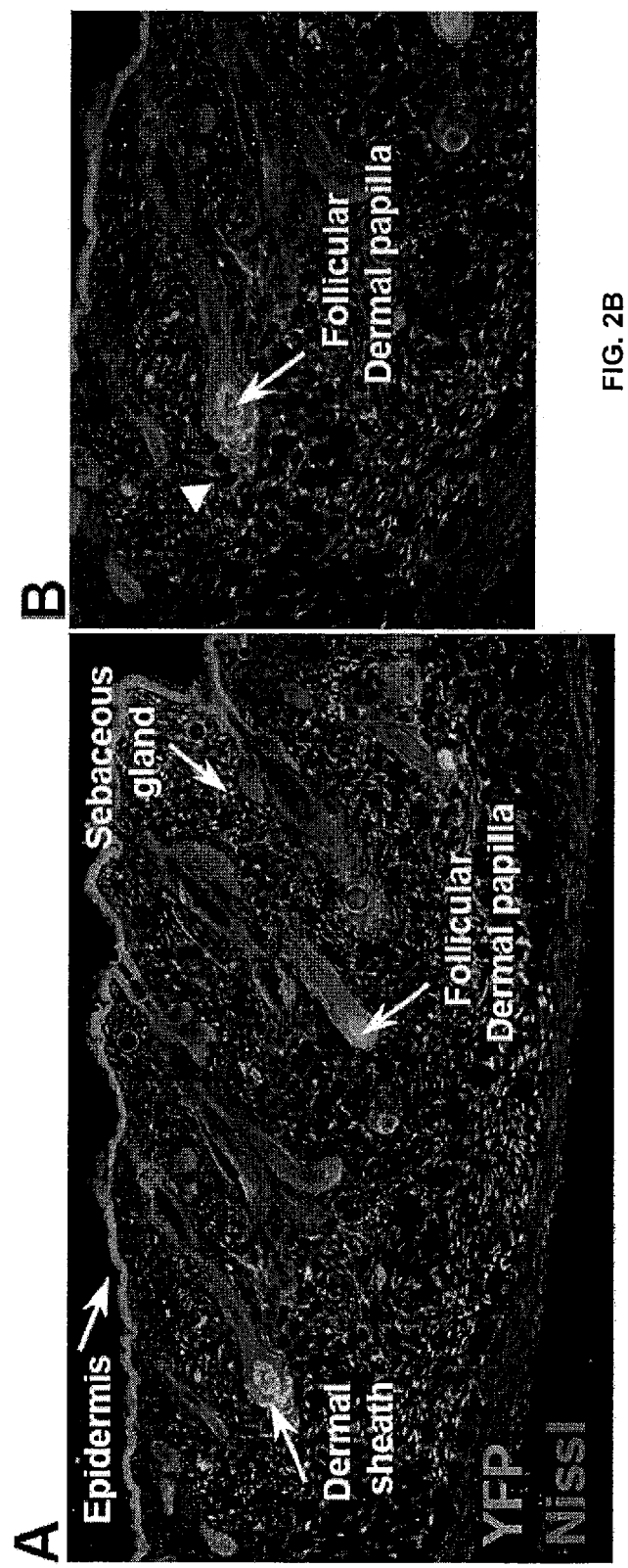
FIGS. 2A and 2B are images showing cultured (GFP-labeled) rat SKPs 14 days after transplantation into adult mouse backskin.
Figures 3A, 3B:
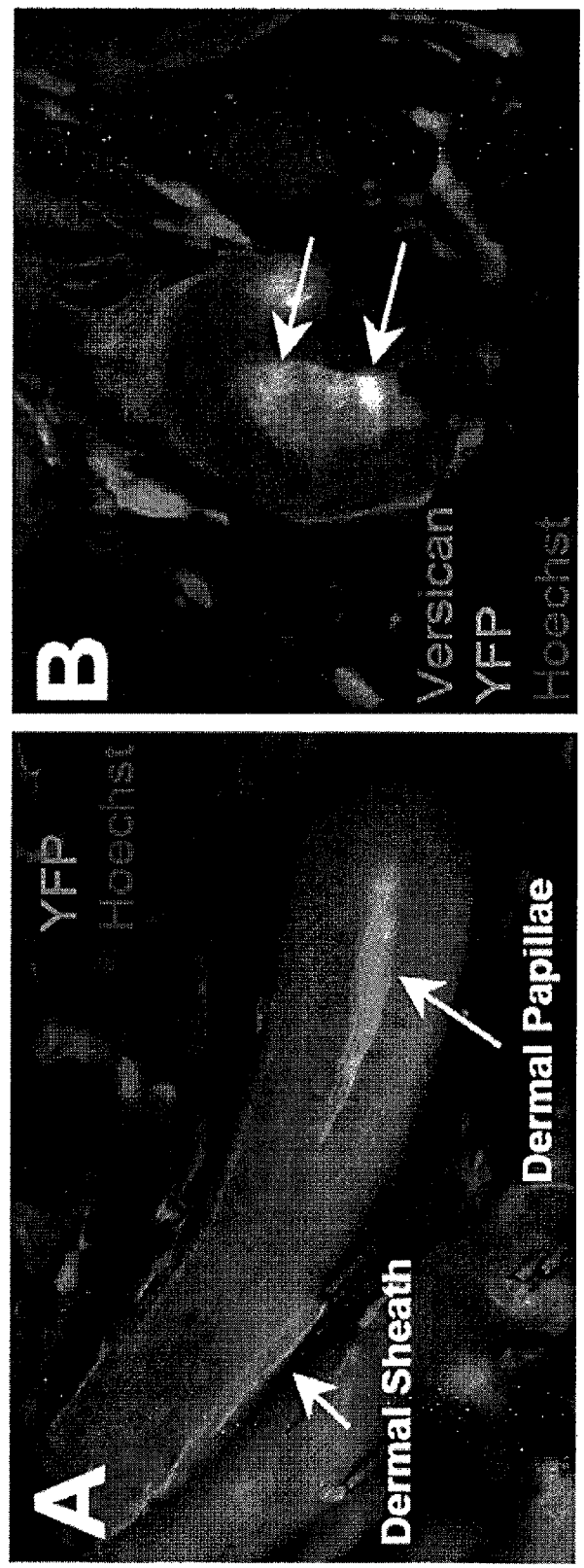
FIGS. 3A-3D are images showing that when injected into normal skin or following either wounding or depilation, transplanted SKPs will migrate into the hair follicle.
Figures 3C, 3D:
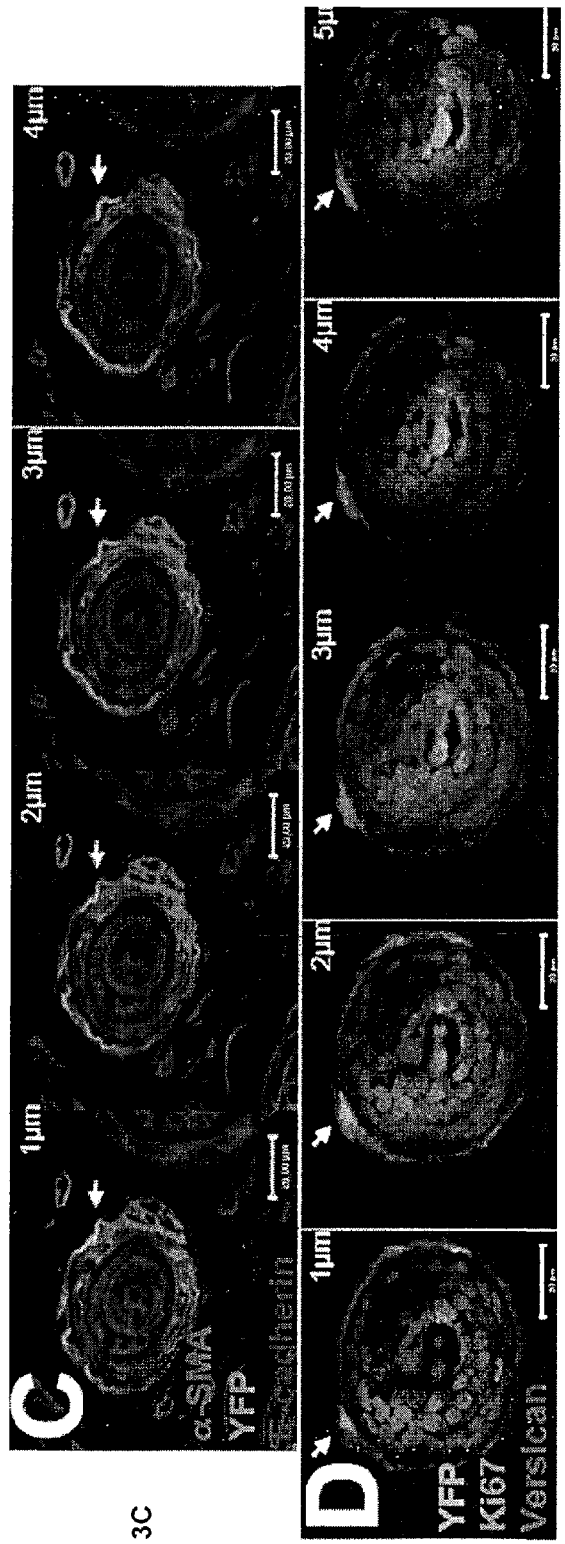
Figure 4:
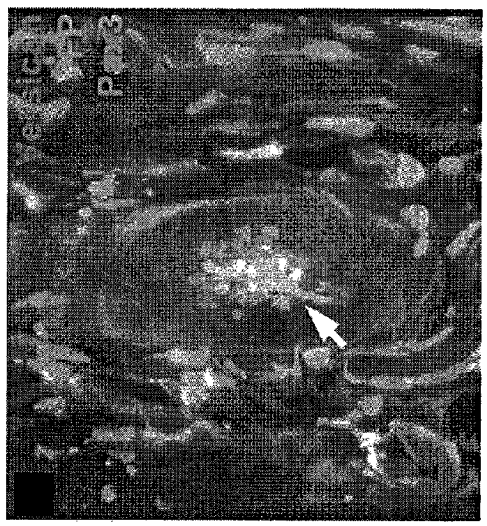
FIG. 4 is an image showing that SKPs integrate into dermal papillae, but not into matrix cells or melanocytes within the hair follicle. SKPs do not co-localize with Pax3, a marker of melanocytic cell lineage within the hair follicle.
Figure 5A:
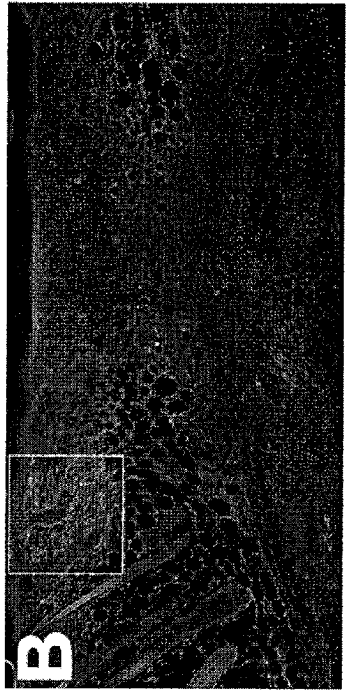
Figure 5B:
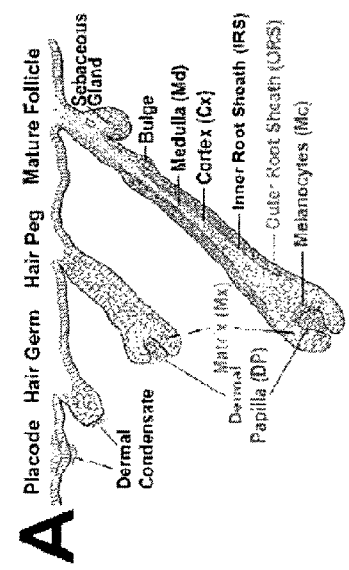

SKPs are capable of surviving after transplantation (FIGS. 2A and 2B) and migrate to the appropriate regions of existing hair follicle (see FIGS. 3A-3D, 4, and 25). SKPs also contribute to hair follicle formation in region adjacent to a skin wound (see FIGS. 5A-5E). In addition, transplanted SKPs retain the inductive capacity and regulatory properties specific to the donor cells; rat SKPs transplanted into mice form "rat" hair (FIGS. 6A-6D).

Figure 7A:
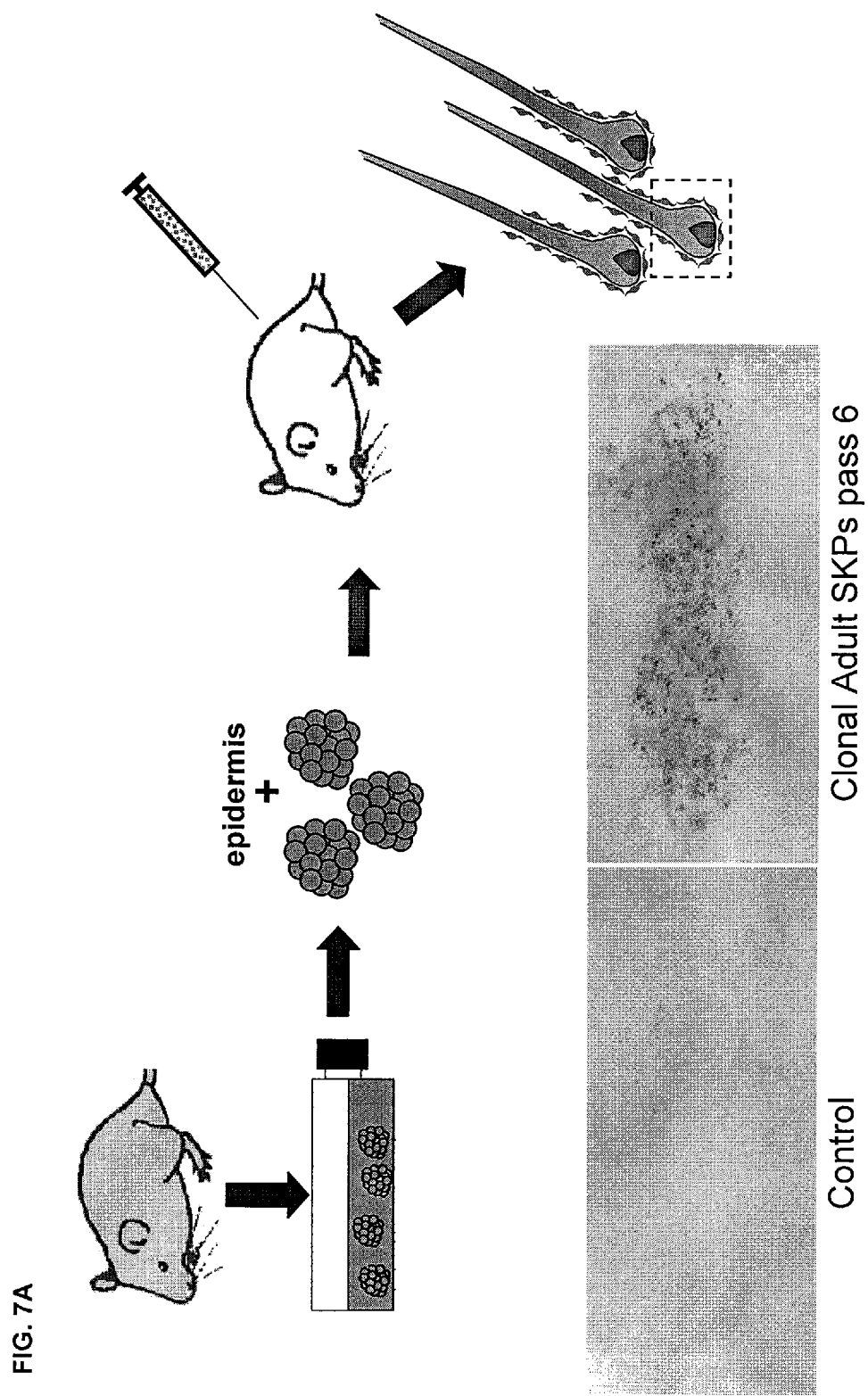
FIG. 7A is a schematic diagram showing the "patch assay" of hair follicle formation. In order to determine if SKPs could actively induce/participate in de novo hair follicle formation, SKPs (generated from E17 or adult yellowgreen fluorescent protein-expressing backskin) were cultured for 14 days. Newborn backskin from C57/B16 mice was dissociated to single cells and then combined with dissociated SKPs at a ratio of 1:2 and suspended in Hanks Balanced Salt Solution. Adult Nu/Nu (hairless) mice were given three injections of cells (15 μl in each injection) along the length of the back. Three weeks later, patches of black hairs could be seen growing underneath the skin.

We also determined that SKPs retain hair follicle-inductive properties by using YFP-labeled SKPs co-transplanted with newborn mouse epidermal keratinocytes into the back skin of adult nude mice using the "patch assay" (FIG. 7A), described for freshly isolated dermal papillae cells (Zheng et al., (2005) J. Invest. Dermatol. 124:867-876). Dorsal backskin keratinocytes were isolated from newborn C57BL/6 mice by floating skin on 0.25% trypsin overnight at 4° C. and then carefully peeling off the overlying epidermis. Epidermal sheets were then minced and incubated in trypsin-EDTA for 30 minutes at 37 degrees and then gently triturated in 10% FBS to stop the reaction. Similar methods for isolating epidermal keratinocytes have been previously described (Lichti et al., (1993) J. Invest. Dermatol. 101:124S-129S). GFP-tagged SKPs were then suspended in HBSS with various concentrations of keratinocytes (typically 2:1, meaning that approximately $10^6$ SKPs combined with $5\times10^5$ keratinocytes) in 20-30 μl of HBSS. Alternatively, intact SKP spheres were also transplanted with fresh keratinocytes. Importantly, grafting of intact SKP spheres, rather than dissociated SKP cells, yielded greater efficiency of de novo follicle formation. In addition, these experiments confirm two important points. First, the dermal papillae or dermal sheath, as these two structures may actually be one and the same, is an endogenous niche for SKPs. Second, SKPs are capable of inducing formation of new hair follicles. (FIGS. 8A-8D). As few as 50 SKPs spheres could be transplanted with $5\times10^5$ keratinocytes resulting in typically 25-35 new hair follicles. Cell suspensions were injected into the dermis/hypodermis of dorsal backskin of athymic nude mice (Charles River Laboratories) using a 27-gauge Hamilton syringe. Two weeks later, hair follicles could be observed in a protruding from the skin as well as coursing throughout the graft beneath the skin. Control transplants consisted of fresh or cultured dermal cells combined with keratinocytes, or keratinocytes alone. Similar results were observed using SKP cells from adult rodents (FIGS. 9A-9G).

Figure 7B:
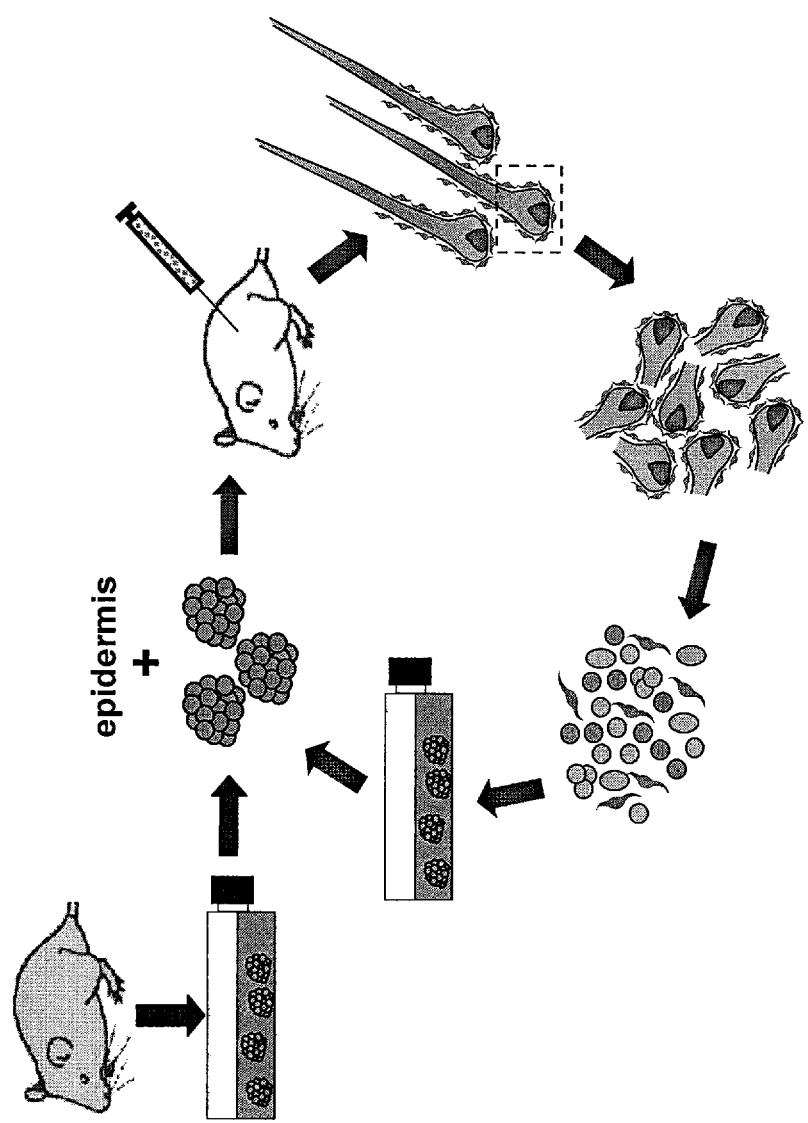
FIG. 7B is a schematic diagram showing that reisolated SKPs from transplanted hair follicles are capable of serial induction and reconstitution of new hair follicles.
Figure 10B:
Figure 10A:
Figure 11F:
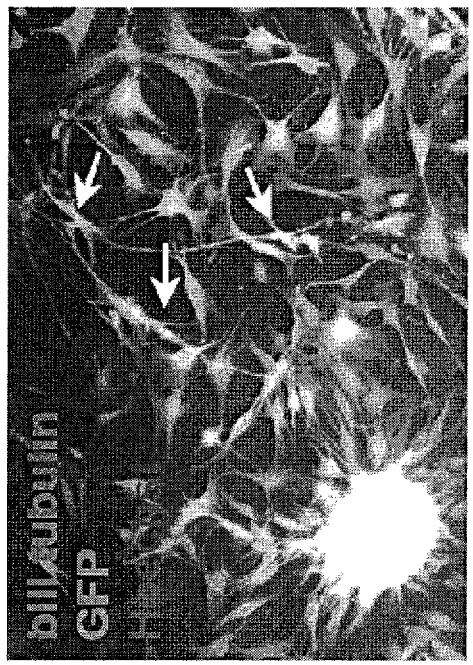
Figure 11E:
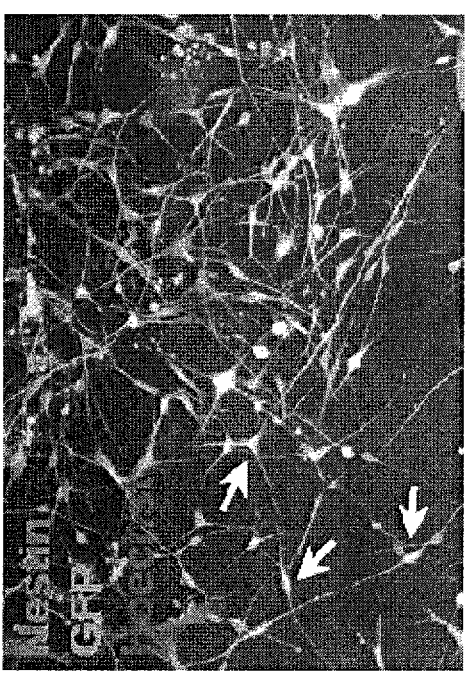

We were also able to reconstitute follicular dermal papillae serially (FIG. 7B). As described above, de novo hair follicles were generated by combining neonatal or adult SKPs (passaged between 1-5 times) with either dissociated newborn skin cells, or epidermal keratinocytes. Two weeks later, grafts of SKP-derived hair follicles were excised, minced and digested in collagenase (Type XI) at 37° C. for 1 hour. Alternatively, single graft-derived hair follicles containing SKP-derived dermal papillae (GFP-tagged) were isolated and the follicle bulbs were dissected, minced and digested with collagenase as above. Tissues were dissociated to single cells by gentle trituration and then grown at 5,000 to 20,000 cells/ml in proliferation media consisting of DMEM:F12 (3:1; Invitrogen) supplemented with 2% B27 (Invitrogen) and containing basic fibroblast growth factor (40 ng/ml) and epidermal growth factor (40 ng/ml) as described above. After 10 to 14 days, floating GFP-labeled spherical colonies were observed. $2 \times 10^5$ to $1 \times 10^6$ GFP-labeled follicle-derived spheres were then recombined with newborn keratinocytes or whole skin in 30 µl of HBSS and injected into the dermis where they formed new hair follicles comprised of GFP positive dermal sheath and dermal papillae. Three successive isolations and expansion of dermal stem cells (SKPs) with subsequent reconstitution of hair follicles were done (FIGS. 10A-10D). These experiments were done twice using two different adult (8 weeks old) backskin samples.

Figures 12A, 12B:
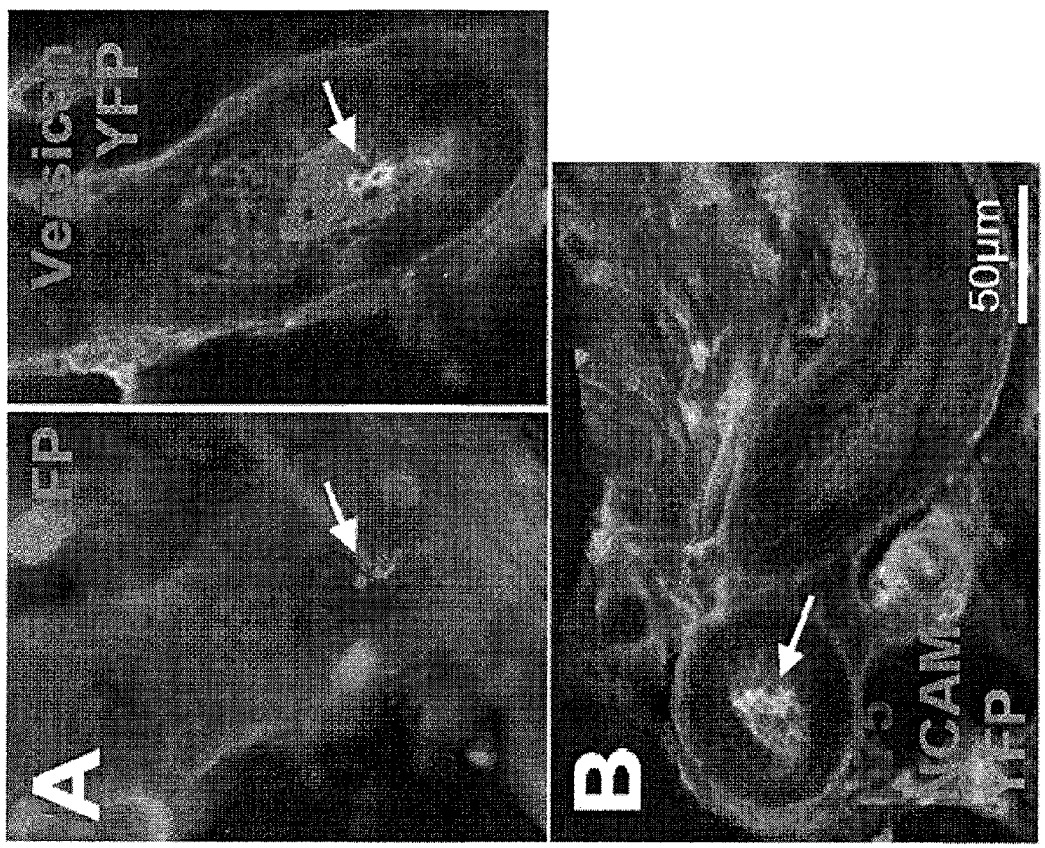
FIGS. 12A-12C depict transplanted adult SKPs forming new hair follicles express markers specific to the dermal papillae. Engrafted SKPs within the follicular dermal papillae express versican (FIG. 12A), neural cell adhesion molecule (NCAM) and p75 neurotrophin receptor (FIG. 12B), and cells within the dermal sheath immunostain with alpha-smooth muscle actin (red) (FIG. 12C).
Figure 12C:
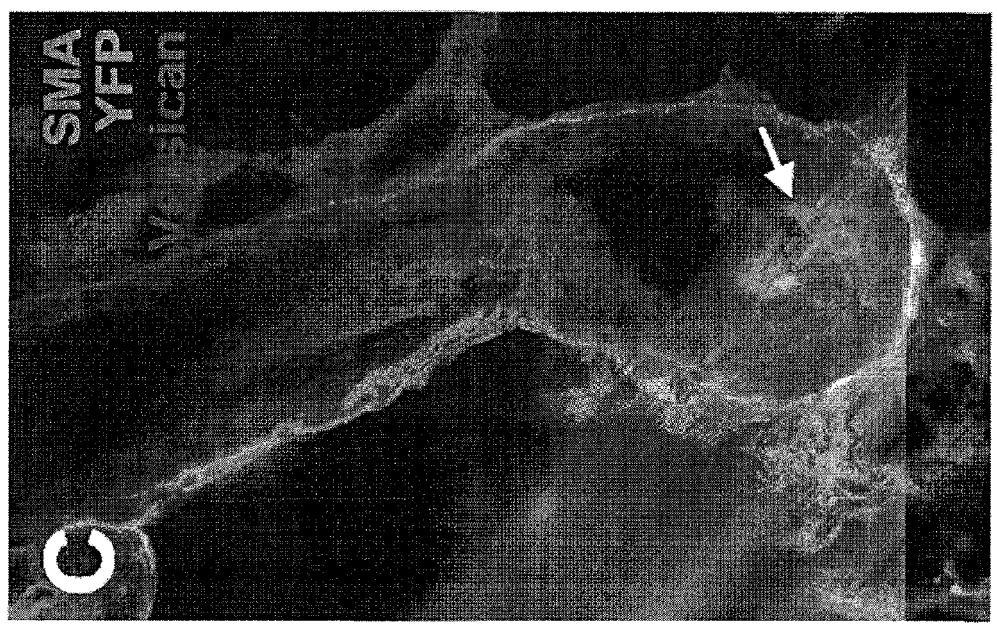

Consistent with these results, transplanted SKPs retain their capacity for self-renewal and multipotency (FIGS. 11A-11F) and express appropriate dermal papilla markets within newly formed hair follicles (FIG. 12A-12C). To determine multipotentiality, SKPs were differentiated in vitro under defined conditions to promote generation of neural, and mesodermal cell types. Schwann cell medium consisted of DMEM-F12 3:1 with 1% N2 supplement, 10 ng/ml neuregulin-1β (heregulin-β1; R&D Systems) and 4 µM forskolin, referred to as Schwann cell differentiation medium. Neuronal medium contained DMEM-F12 3:1 with 1% N2 supplement, 1% B27 supplement, 10% fetal bovine serum (FBS), 50 ng/ml NGF and 50 ng/ml of BDNF. Medium was changed every 3-4 days.

Generation of hair follicles is useful in disorders including conditions characterized by loss or lack of hair, including for example, alopecia, male pattern baldness, female pattern baldness, accidental injury, damage to hair follicles, surgical trauma, burn wound, radiation or chemotherapy treatment site, incisional wound, donor site wound from skin transplant, and ulceration of the skin. In some embodiments, hair growth is induced in an area or areas where hair was previously present but has been lost. Alternatively or in addition to the conditions noted above, the induced hair growth may be for cosmetic purposes.

Compositions of SKPs and Keratinocytes

Based on the discovery that transplanting a combination of SKPs and keratinocytes can induce de novo hair follicle formation in mammals, the present invention provides compositions including a combination of SKPs and keratinocytes. Such compositions may include cells isolated from any source and may include any amounts, any ratio, or any purity of SKPs and keratinocytes. Such compositions may include at least 10, 100, 1,000, 10,000, or 100,000, 500,000, or 1,000,000 cells. The ratio of SKPs to keratinocytes in the composition may be at least 1:1,000, 1:100, 1:50, 1:20, 1:10, 1:5, 1:4, 1:3, 1:2, 1:1, 2:1, 3:1, 4:1, 5:1, 10:1, 20:1, 50:1, 100:1, or 1,000:1. The cells may be enriched such that the combination of SKPs and keratinocytes make up at least 10%, 20%, 30%, 40%, 50%, 60%, 70%, 80%, 90%, 95%, 99%, or even 100% of the total cells in a composition of the invention (e.g., free from macrophages or lymphocytes).

Compositions of the invention may further include a pharmaceutically acceptable carrier (e.g., suitable for epidermal, intradermal, subdermal, or subcutaneous administration) and may further contain non-toxic pharmaceutically acceptable adjuvants. The formulation and preparation of such compositions are well known to those skilled in the art of pharmaceutical formulation.

Compositions for parenteral (e.g., epidermal, intradermal, subdermal, and subcutaneous) use may be provided in unit dosage forms (e.g., in single-dose ampoules), or in vials containing several doses and in which a suitable preservative may be added (see below). The composition may be in form of a solution, a suspension, an emulsion, an infusion device, or a delivery device for implantation. Apart from the cells, the composition may include suitable parenterally acceptable carriers and/or excipients. The cells may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing agents.

As indicated above, the pharmaceutical compositions according to the invention may be in a form suitable for sterile injection. To prepare such a composition, the cells are suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, dextrose solution, and isotonic sodium chloride solution. The aqueous formulation may also contain one or more preservatives (e.g., methyl, ethyl or n-propyl p-hydroxybenzoate).

Kits Containing SKPs

The invention further provide kits containing SKPs cells. Exemplary kits include SKPs cells, keratinocytes, and instructions for use (e.g., instructions for introduction into the skin of a mammal). The SKP cells may be in a composition with keratinocytes. In other embodiments, the kit includes two compositions, one composition including SKPs and one composition including keratinocytes. The kits may further include any of the reagents described herein (e.g., cell culture apparatus, dermal sheets containing either SKPs or SKPs and keratinocytes).

Wound Healing

Figure 13C:
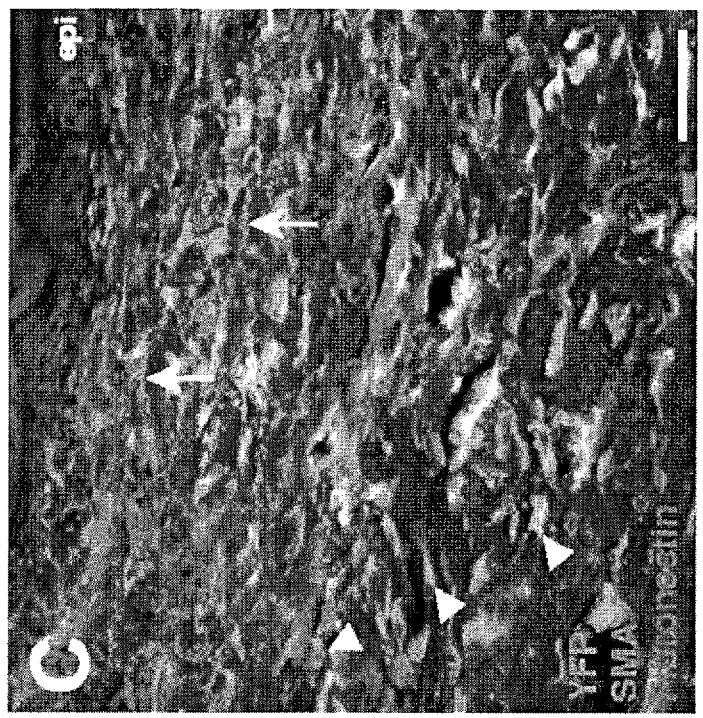
FIGS. 13A-13C show that SKPs migrate into and contribute to wound healing. Adult NODSCID mice received a 3 mm full thickness skin wound. Immediately following, YFP labeled SKPs were transplanted (intra-dermal) into the surrounding regions of intact skin. Three weeks following, SKPs can be observed filling the wound cavity (FIGS. 13A and 13B), comprising what would be the scar, suggesting that SKPs respond to migratory cues and actively contribute to wound healing.
Figure 13A:
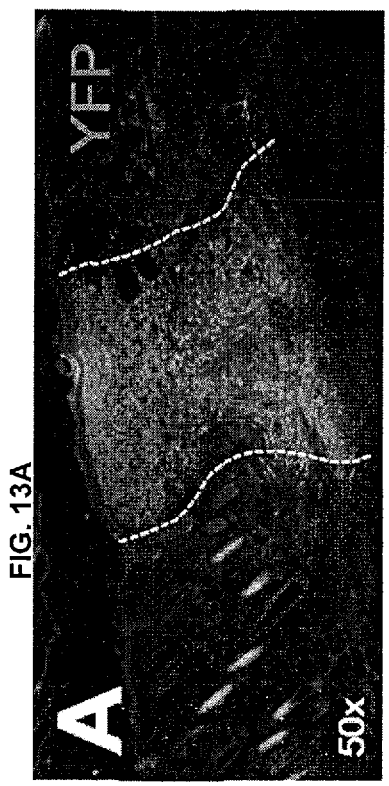
Figure 13B:
Figure 26:
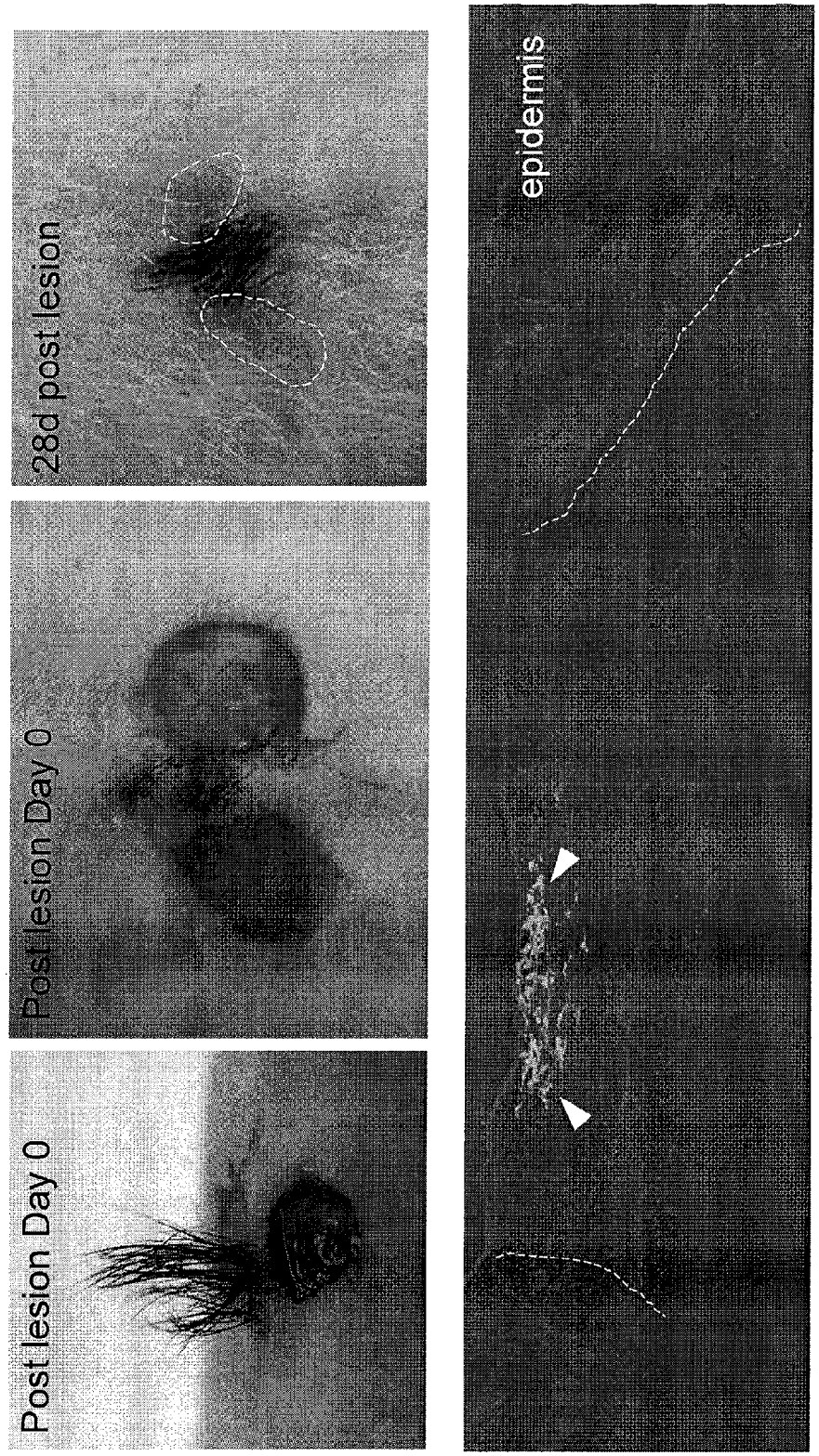
FIG. 26 is a set of images showing that the are involved in dermal wound healing. SKPs within the DP/DS of transplanted hair follicles are observed to migrate to wound sites and contribute to wound healing.

Transplanted SKPs migrate from areas surround a wound into the wound itself, and integrate into structures associated with the hair follicle (see WO 2005/071063). Here, we show that SKPs cells both migrate into the wound and contribute to wound healing, both upon transplantation (FIGS. 13A-13C) and from adjacent hair follicles (FIG. 26).

Dermal Sheets

Figure 14B:
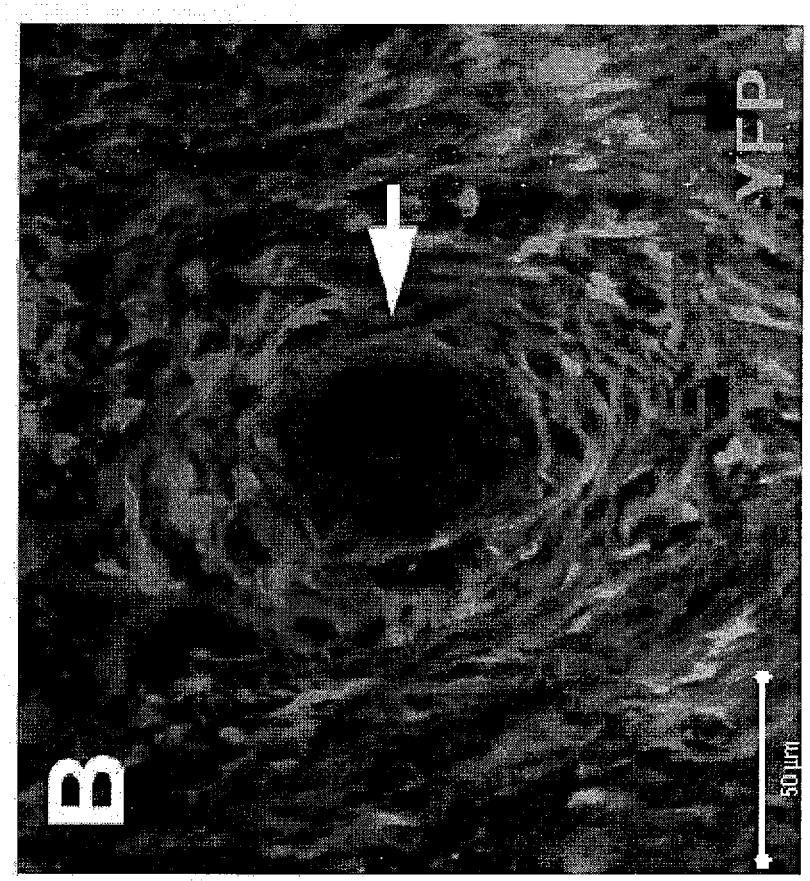
FIGS. 14A and 14B show that transplanted SKPs support formation of epidermal appendages after 1 week. Depicted is a dorsal view of a dermal sheet comprised of SKPs which have been combined with epidermal keratinocytes. SKPs surround structures immunostaining for p63 (FIG. 14A) and e-cadherin (FIG. 14B), which are specific to epidermal cell types.
Figure 14A:
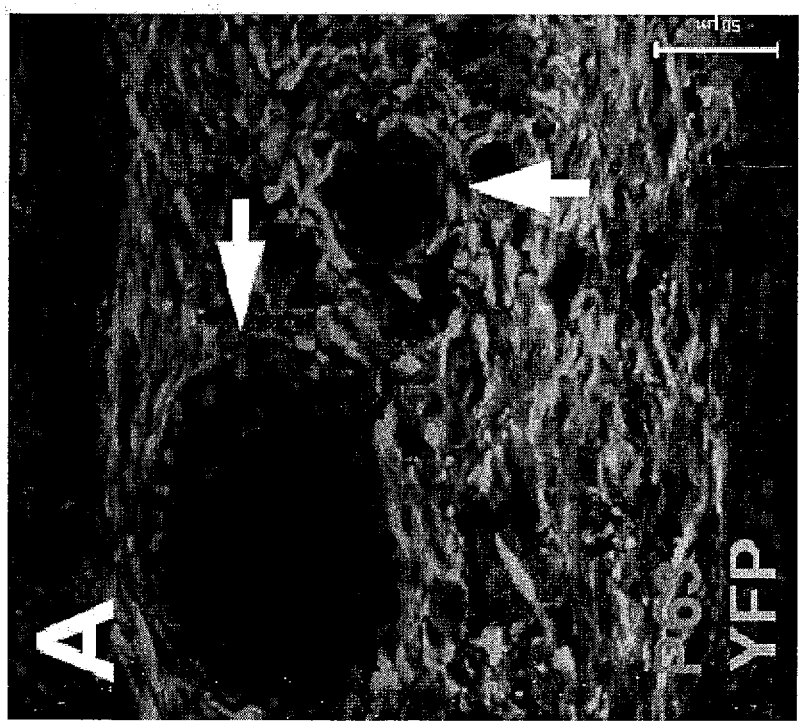

Using SKPs, we have generated dermal sheets in vitro. The invention thus features methods of making dermal sheets from SKPs, sheets produced by these methods, and methods of treating skin injuries using the dermal sheets. We have also shown that sheets of dermis produced by SKP cells are capable of supporting growth of epidermal cells (FIGS. 14A and 14B). Such sheets can be useful in all applications in which skin grafts are used, for example, in the treatment of burns, mechanical injury, and ulcers (e.g., resulting from diabetes), or as part of a surgical procedure requiring skin replacement. The dermal sheets may additionally be combined with matrix or scaffolding elements (e.g., collagen, alginate, and polymers) to provide structure to the dermal sheet, as detailed below. The dermal sheet may contain cells solely differentiated from SKPs. In other embodiments, the sheets contain two or more layers of cells (e.g., a layer of dermal cells and a layer of epidermal cells).

Generation of Dermal Sheets

Figure 15:
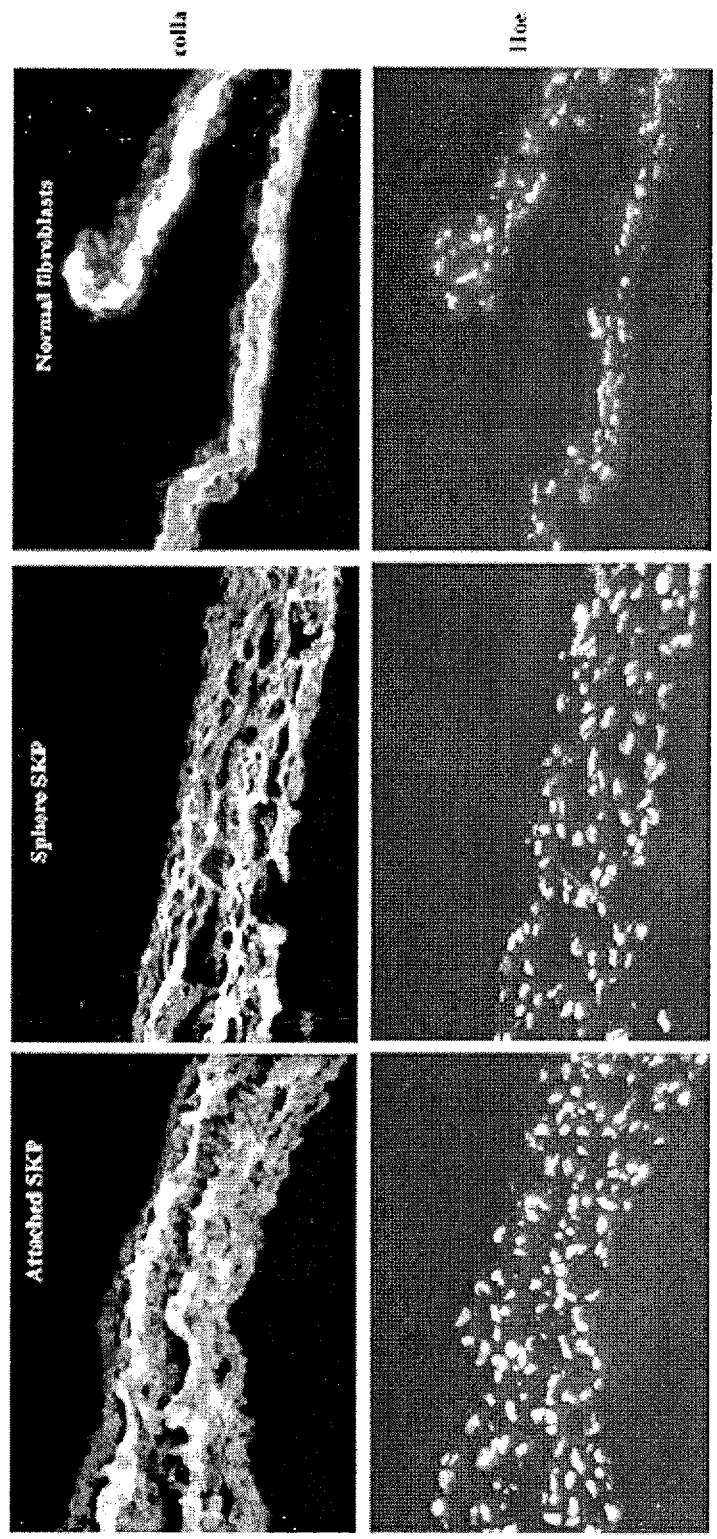
FIG. 15 shows that human SKPs generate dermal sheets in vitro. Human SKPs (grown adherent or as spheres) are capable of generating dermal sheets. Sheets generated by SKPs are significantly thicker than normal human fibroblasts.

In one example, SKPs from human or rodent were generated as described above. SKP spheres (human or rat) were dissociated to single cells and grown adherently in 10 cm plastic tissue culture dishes coated with poly-D-lysine and laminin. Culture medium consisting of DMEM supplemented with 10% FBS and ascorbic acid was used for 4 weeks. SKP-derived dermal sheets were compared to dermal sheets derived from normal skin fibroblasts, and found to be significantly thicker (FIG. 15).

Epidermal sheets were generated using similar techniques. Keratinocytes were isolated by floating skin on 0.25% trypsin overnight at 4° C. and then carefully peeling off the overlying epidermis. Epidermal sheets were then minced and incubated in trypsin-EDTA for 30 minutes at 37° C. and then gently triturated in 10% FBS to stop the reaction. Similar methods have previously been described by Lichti et al. ((1993) J. Invest. Dermatol. 101:124S-129S). Isolated keratinocytes were cultured in DMEM containing low calcium and 5% serum. Epidermal sheets were then overlayed onto dermal sheets and dermal thickness was assessed two weeks later.

The dermal sheets can further be applied to or generated on a scaffold or matrix structure to provide support or to generate a particular shape. Any scaffolding or matrix materials known in the art may be used in the present invention. Exemplary materials for such a matrix include chitosan, alginate, and collagen (see, e.g., U.S. Pat. No. 6,699,287). Foams useful as matrices are described, for example, in U.S. Patent Application Publication No. 2003/0105525. Alginate-based matrices are described, for example, in U.S. Pat. No. 6,642,363. Such materials may be bioabsorbable or biodegradable, such as cotton, polyglycolic acid, cellulose, gelatin, and dextran. Nonbioabsorble or materials include polyamide, polyester, polystyrene, polypropylene, polyacrylate, polyvinyl, polycarbonate, polytetrafluorethylene, and nitrocellulose compounds. See, e.g., U.S. Pat. No. 5,512,475.

The dermal sheets of the invention may include additional cell types as well. For example, stromal cells (e.g., fibroblasts, endothelial cells, macrophage, monocytes, leukocytes, and adipocytes) may be added to the dermal sheets or co-cultured with the SKPs.

Treatment Using Dermal Sheets

The dermal sheets of the invention may be used in any application where skin grafts are typically used, including wounds resulting from burns, mechanical damage to the skin (e.g., damage resulting from a bone fracture), infection, ulcers (e.g., resulting from diabetes) as well as post-surgically or for cosmetic reasons. The sheet can be applied to the site requiring the sheet (e.g., the site of injury or infection) using any attachment method including stitches, sutures, and adhesives (e.g., fibrin glue) known in the art.

Further Characterization of SKP Cells

We have performed additional studies defining the biological role of SKPs in vivo, and provide evidence that they represent an adult dermal stem cell. In particular, they can reconstitute the adult dermis, contribute to dermal wound-healing, and home to a hair follicle niche, and instruct epidermal cells to make hair follicles. In addition, hair follicle-derived SKPs will self-renew, maintain their multipotency, and can serially reconstitute hair follicles.

Figures 16A, 16B, 16C:
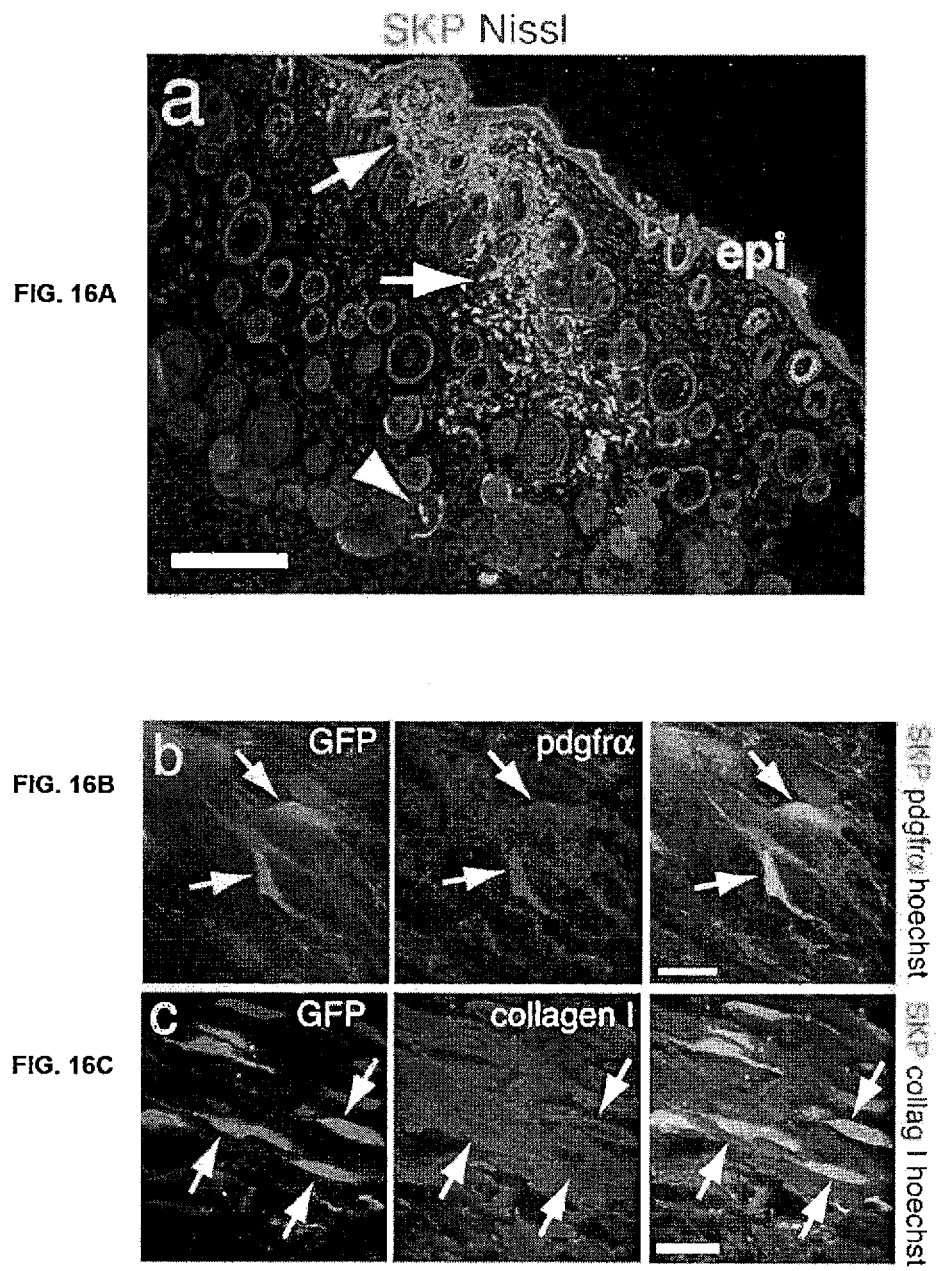

To determine whether SKPs represented dermal stem cells, SKPs were generated from back skin of neonatal YFP-expressing mice, passaged once, and transplanted into back skin of adult NOD/SCID mice. Two to three weeks later, YFP-positive SKPs were observed throughout the dermis, with a morphology and location similar to interfollicular dermal fibroblasts (FIG. 16A). Many SKPs were also present in the dermal papilla (DP) and dermal sheath (DS) of hair follicles (FIGS. 16A and 16D). Immunocytochemistry revealed the phenotype of these transplanted cells. Within interfollicular dermis, most YFP-positive cells expressed the dermal fibroblast markers collagen type I, fibronectin, vimentin, and PDGFRα and some expressed α-smooth muscle actin (α-sma), characteristic of dermal myofibroblasts (FIGS. 16B, 16C, 20A, and 20B). By contrast, YFP-positive cells within the DP expressed DP markers such as versican (FIG. 16E), while those in the DS were α-sma-positive, as were resident DS cells (FIG. 16F) Moreover, a small subpopulation of YFP-positive DS, but not DP, cells expressed the proliferation marker Ki67 (FIG. 16G). YFP-positive cells were never observed within epidermis or epidermal components of hair follicles, and did not express markers for melanocytes such as Pax3 or tyrosinase (FIGS. 16E and 20C). Thus, SKPs transplanted into adult dermis differentiate into dermal cell types, with some homing back to a hair follicle niche.

Figure 16L:
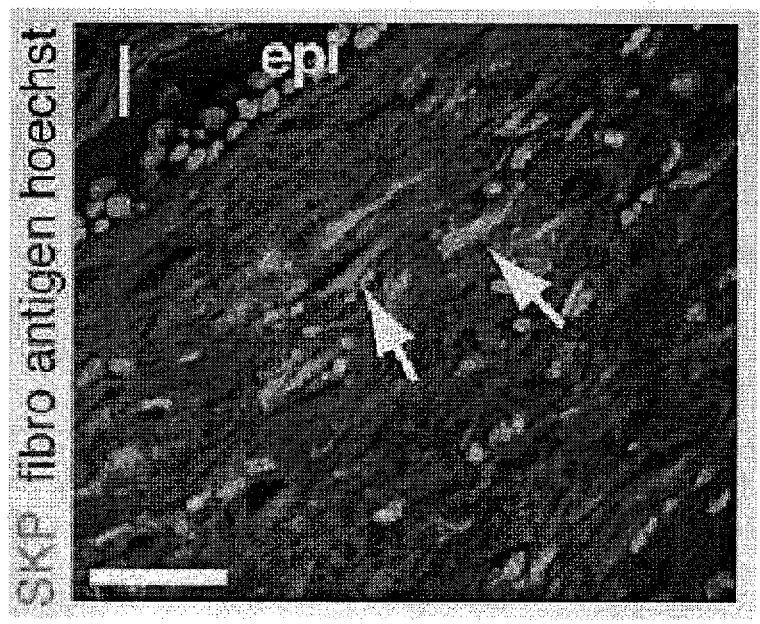
Figure 16M:
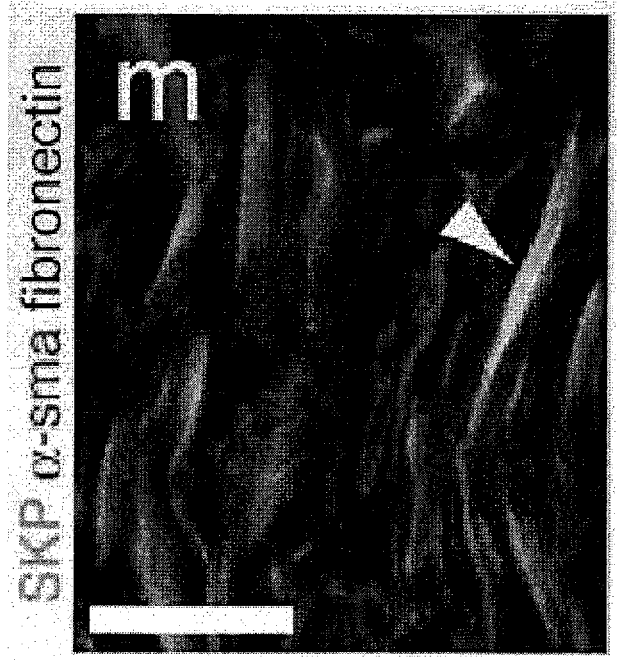
Figure 17A:
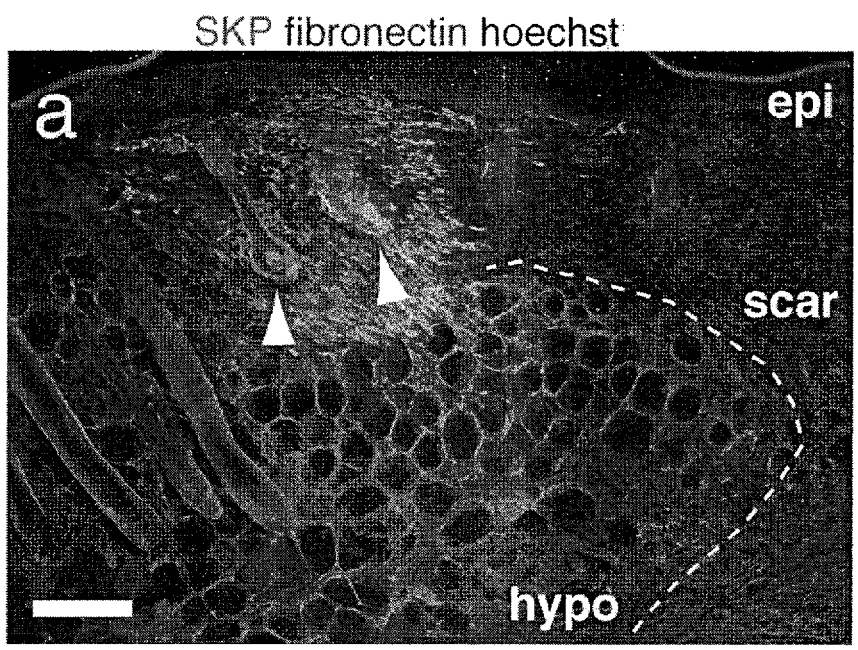
FIGS. 17A-17K are a set of images and graphs showing that SKPs can reconstitute their niche and instruct epidermal cells to generate hair follicles.
Figure 17B:
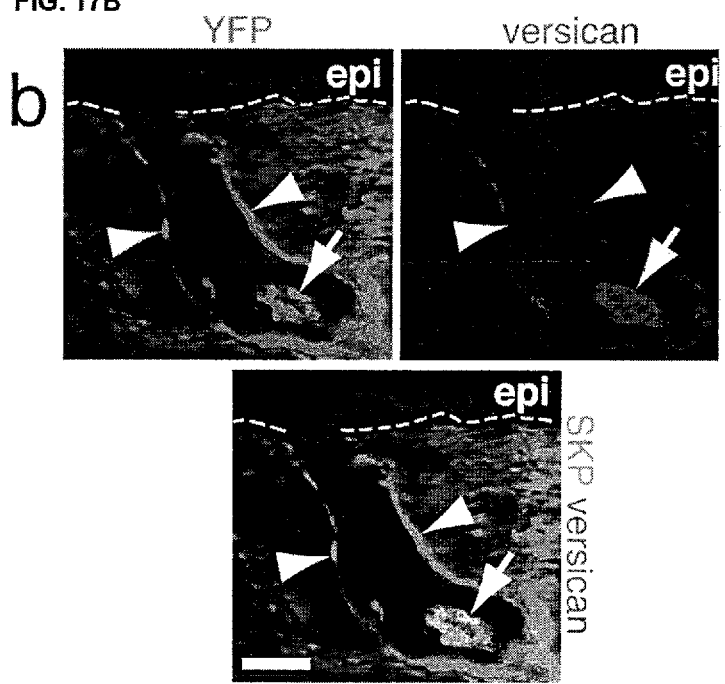
Figure 17C:
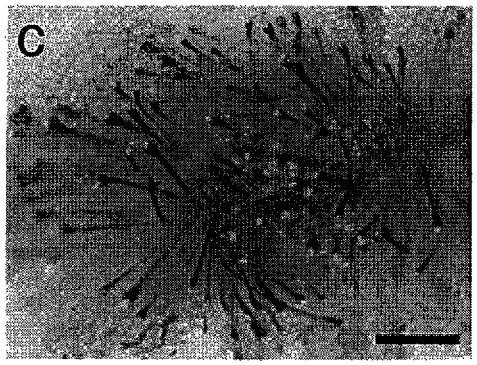
Figure 17D:
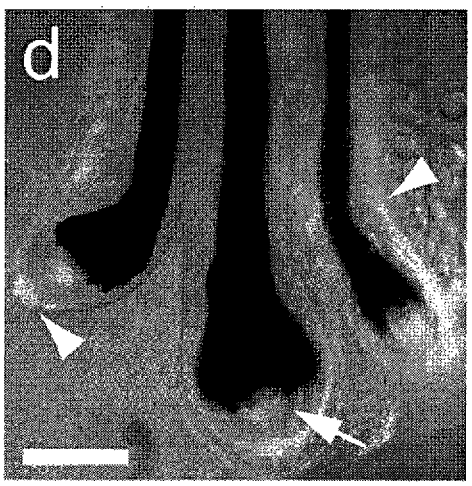
Figure 17E:
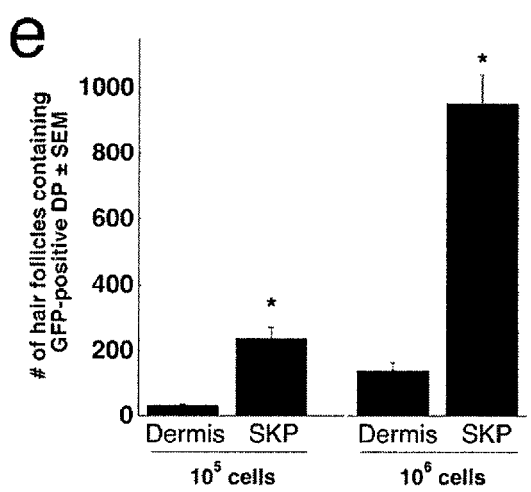

Three lines of evidence indicated that recruitment of SKPs to a follicle niche was an active process. First, two other adult stem cells, bone marrow mesenchymal stem cells (MSCs) and forebrain neural stem cells (NSCs), did not associate with hair follicles when transplanted in the same way (FIGS. 20D-20F). Second, recruitment of SKPs into the follicle niche increased 3-fold when follicles were induced to enter the anagen growth phase by hair depilation prior to transplant. Two to three weeks post-transplant, SKPs were recruited to the DS and many had entered the DP (FIGS. 16H and 16I), with each DP containing approximately 6-fold more transplanted cells (FIG. 16J). The third line of evidence came from experiments where SKPs were transplanted adjacent to or within punch wounds on back skin of NOD/SCID mice. Two weeks post-transplant, YFP-positive cells reconstituted a large part of the scar, where most expressed fibroblast-specific antigen, collagen type 1, and fibronectin, and some expressed α-sma (FIGS. 16K-16M; FIGS. 21A-D). By three weeks, YFP-positive, versican-positive cells were also present within the DP of hair follicles with an immature appearance typical of newly-forming follicles (FIGS. 17A and 17B). Thus, SKPs may contribute the inductive mesenchymal cells necessary for new follicle formation in wounded skin.

Thus, SKPs are actively recruited into a follicle niche. SKPs re-entering this niche may further retain the ability to induce hair follicle formation. To test this directly, we used the "patch assay" of hair follicle formation (Zheng et al. (2005) J Invest Dermatol 124:867-76); SKPs were generated from either YFP-expressing mice or GFP-expressing rats, were mixed with neonatal epidermal cells from C57/B16 mice, and were transplanted beneath the dermis of adult nude mice. Epidermal cells generated no or very few hair follicles when transplanted alone or with MSCs or NSCs (FIGS. 22A-22E). By contrast, epidermal cells mixed with neonatal or adult SKPs generated hair follicles where the entire DS and DP were comprised of genetically-tagged cells (FIGS. 17C, 17D, 22H, and 22I). By direct comparison, dissociated rat SKPs were 5-fold more efficient at inducing hair follicle formation than were neonatal rat dermal cells (FIGS. 17E and 22F-22J). As a consequence, SKPs reconstituted the dermal components of hair follicles even when mixed with total neonatal skin cells (FIGS. 22K and 22L).

Figure 17F:
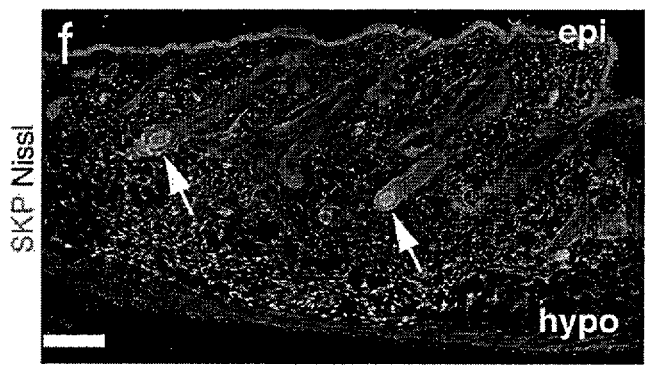
Figure 17G:
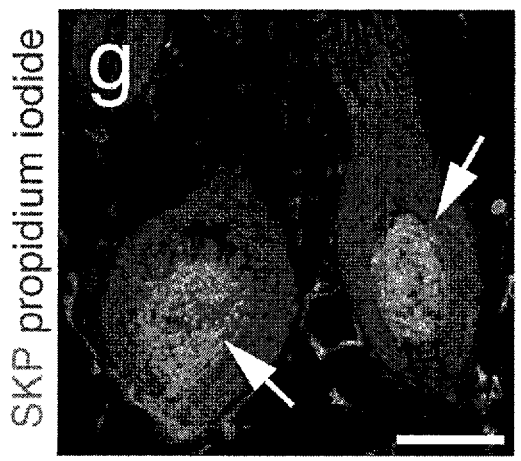
Figure 17H:
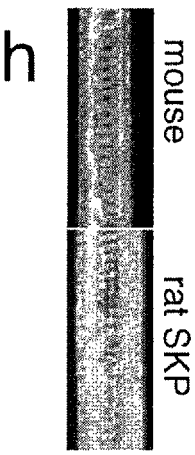
Figure 17I:
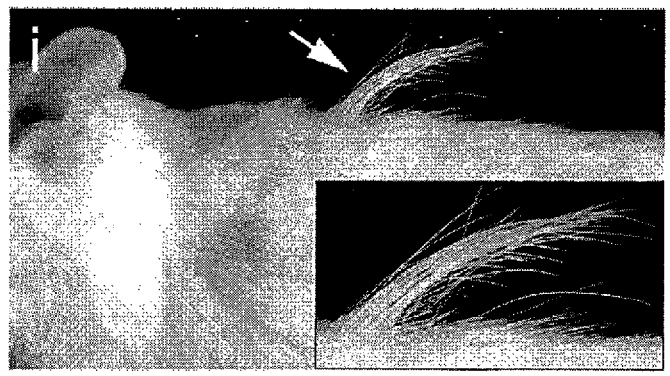
Figure 17J:
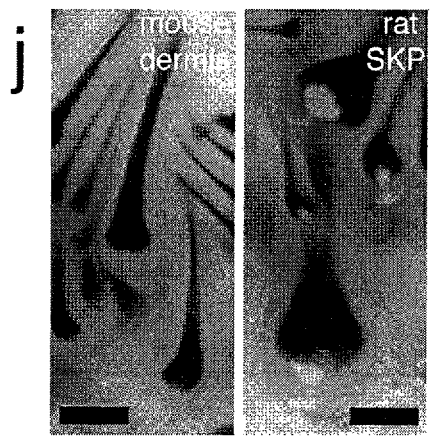
Figure 17K:
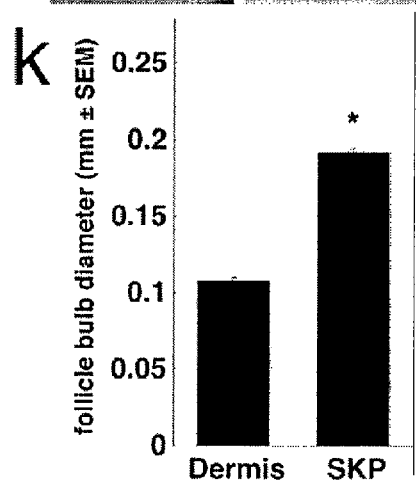

SKPs can thus instruct neonatal epidermal cells to generate hair follicles. To determine if they could do so in vivo, GFP-positive SKPs from adult rats were transplanted into adult NOD/SCID mouse back skin. These transplanted rat SKPs appeared to have a competitive advantage, as 8 weeks post-transplant, they comprised the majority of dermal cells in the transplanted region (FIG. 17F). Moreover, the DP and DS of many correctly-oriented hair follicles were entirely comprised of GFP-positive cells (FIGS. 17F and 17G). Remarkably, relative to the endogenous murine hairs, hairs induced by the rat SKPs were longer (10.41 mm±0.23 versus 7.96 mm±0.11; $p<0.0001$) and had increased follicle bulb diameter (107.236 µm±4.99 versus 82.27 µm±2.51; $p<0.01$) and hair fiber width (49.26 µm±0.871 versus 44.6 µm±0.83; $p<0.001$) (FIGS. 17G-17I). Although many follicles containing SKP-derived cells were in anagen (FIG. 17G), some cycled in synchrony with endogenous follicles and had progressed to catagen/telogen phase (FIG. 22M), indicating that follicle-associated SKPs respond to local signals governing the hair cycle. To ask whether rat SKPs intrinsically induced these larger follicles, we performed patch assays, mixing mouse epidermal cells with dissociated rat SKPs. Quantification indicated that rat SKPs instructed mouse epidermal cells to generate larger, more rat-like hair follicles than did murine dermal cells (FIGS. 17J and 17K).

Figure 18E:
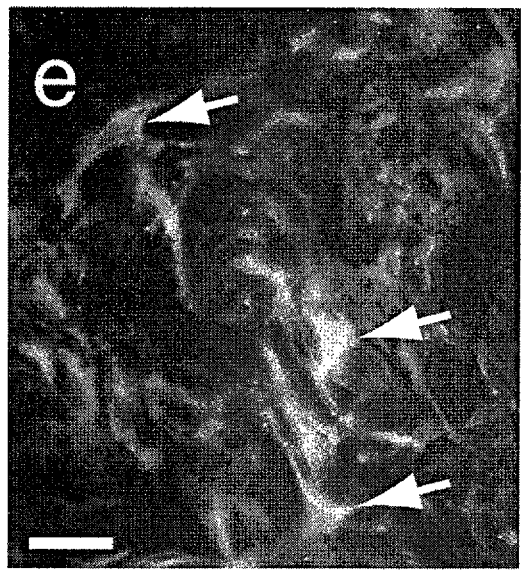
Figure 18F:
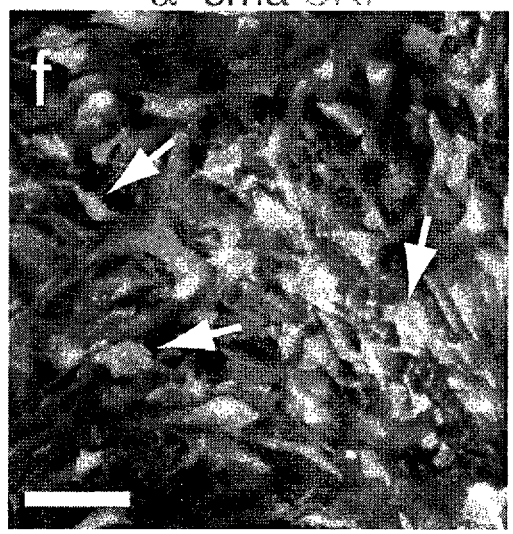
Figure 23B:
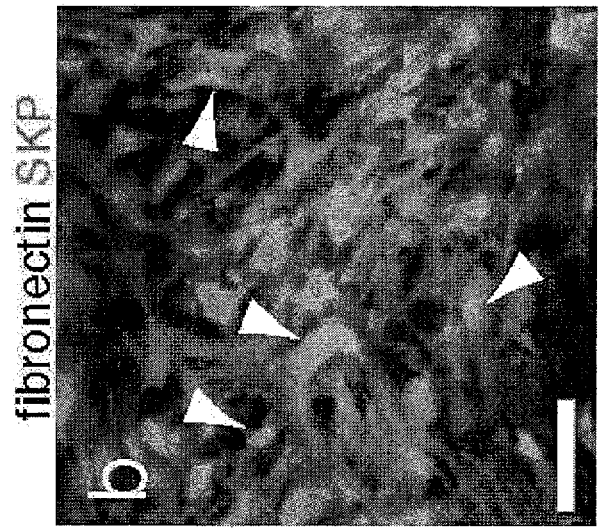
FIGS. 23A and 23B are photomicrographs showing that clonal SKPs can both induce hair follicle formation and contribute dermal fibroblasts to the interfollicular dermis.
Figure 23A:
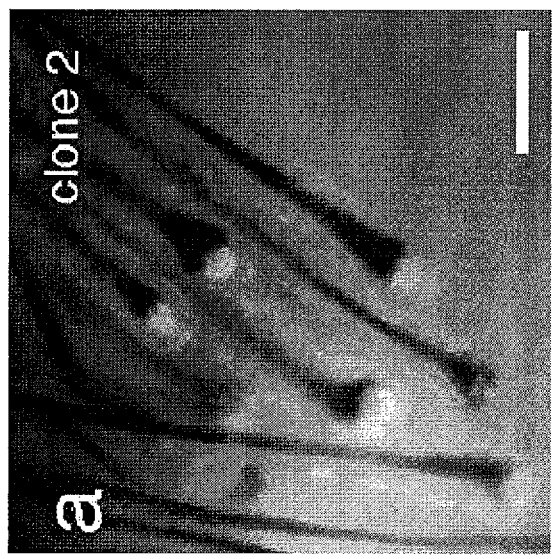
Figure 24:
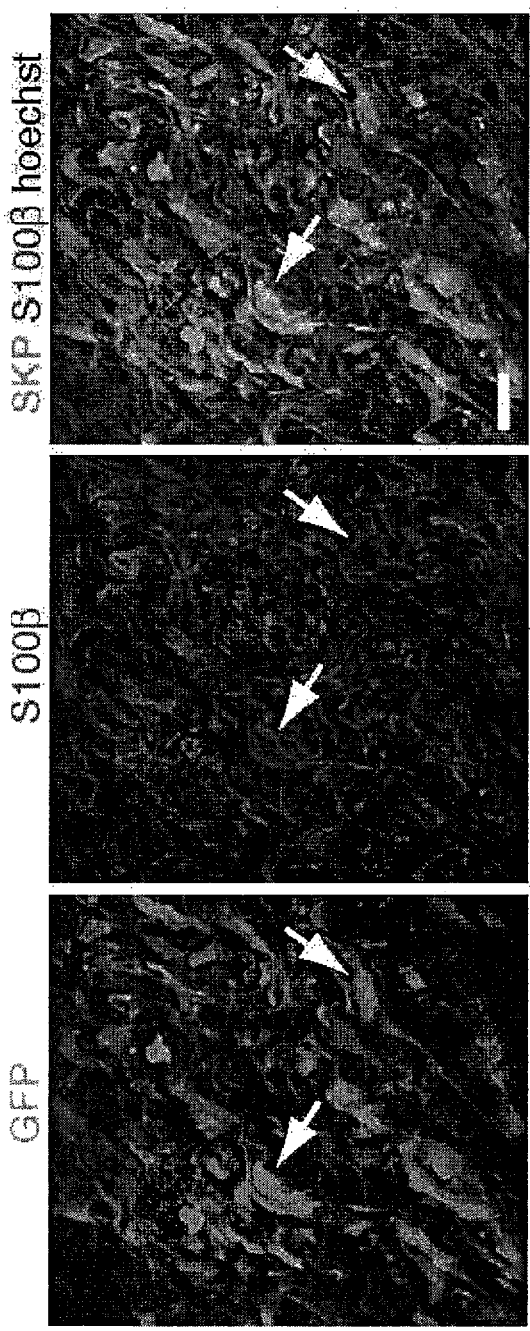
FIG. 24 shows that follicle-derived SKPs reconstitute the interfollicular dermis. High magnification images of the same field showing transplanted cells (left) immunostained for the dermal fibroblast marker S100β (center). Right panel is the merge, and arrows indicate double-labeled cells. Scale bar is 25 µm.
Figure 25:
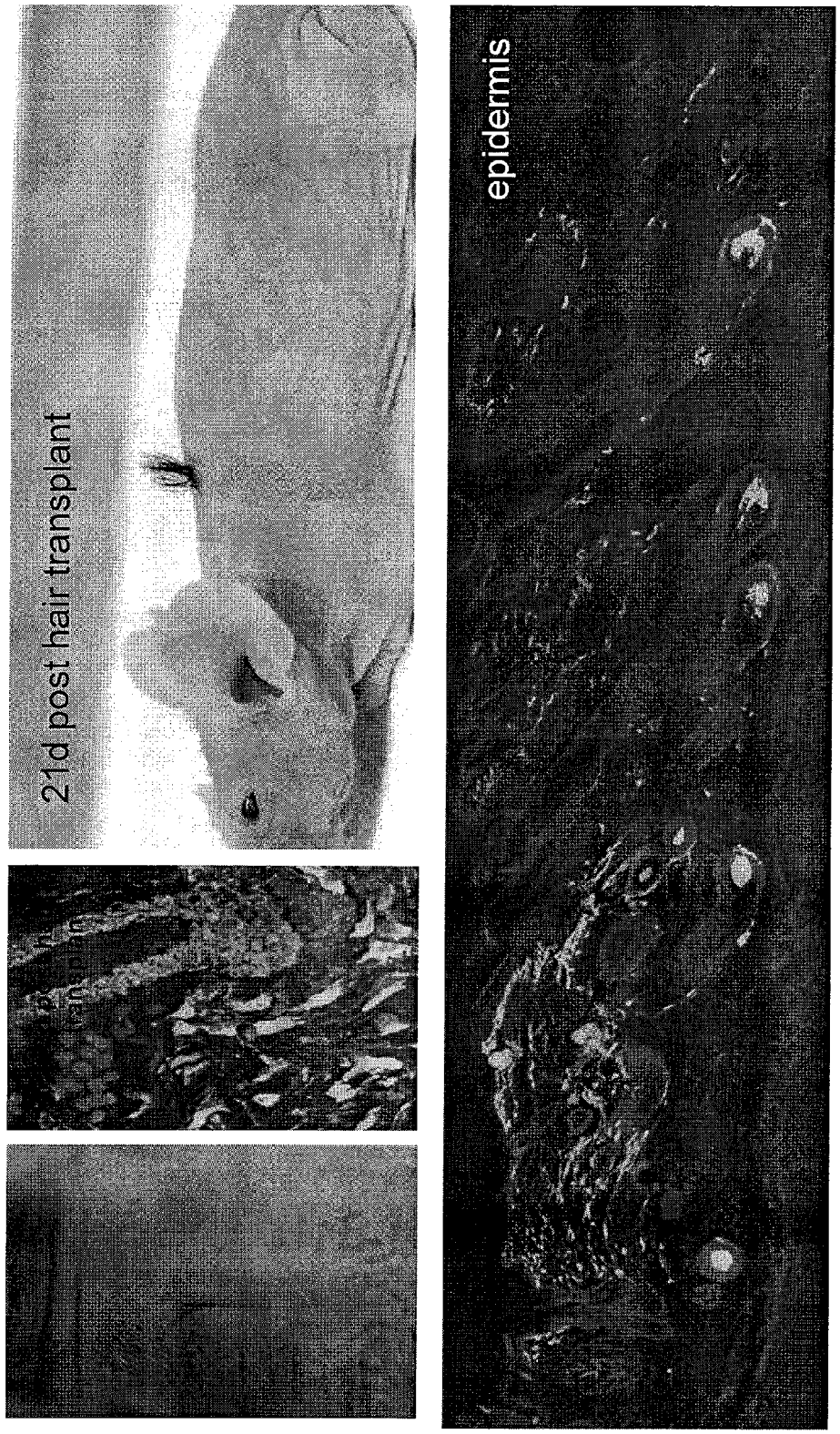
FIG. 25 is a set of images showing that, although cells are retained within the DP and DS of grafted hair follicles, the dermal papillae/dermal sheath is a reservoir of dermal stem cells that continuously contribute cells to the dermis.

Thus, SKPs have the capacity to both generate dermal cells and to induce hair follicle morphogenesis. To determine if individual SKP cells were multipotent with regard to these two activities, we analyzed clones of adult rat SKPs. Of seven clonally-derived lines that were passaged a minimum of six times (approximately 8-12 weeks in culture), five induced de novo follicle formation in the patch assay (FIGS. 18A, 18B, and 23A). Indeed, when 50 clonal spheres were mixed with $5 \times 10^5$ total neonatal skin cells, 30±2 hair follicles had DP entirely comprised of GFP-positive SKPs. This activity was persistent; one clone induced follicle formation after 11 months in culture, albeit relatively inefficiently (FIG. 18C). Transplantation of two clones into adult NOD/SCID mouse skin demonstrated that they both reconstituted the DP and DS of hair follicles in vivo (FIG. 18D), and generated fibronectin- and vimentin-positive interfollicular dermal fibroblasts and SMA-positive myofibroblasts (FIGS. 18D-18F and 23B). Thus, single SKP clones were multipotent with regard to both dermal activities in vivo.

Figure 18G:
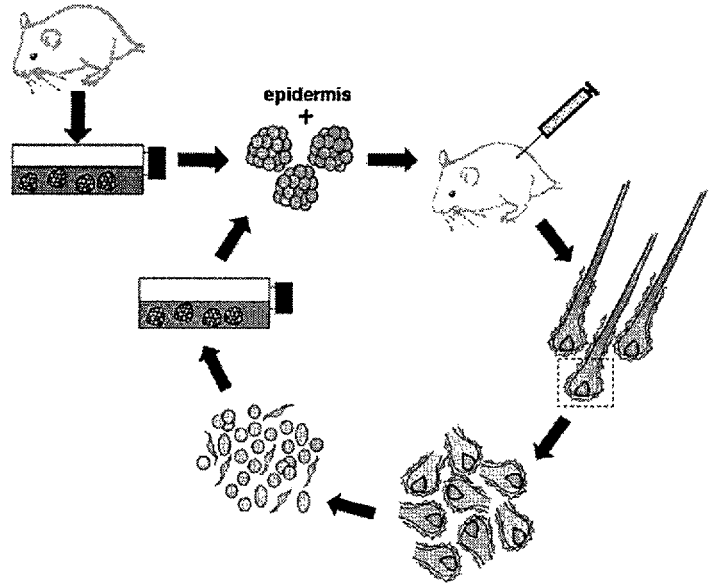
Figure 18H:
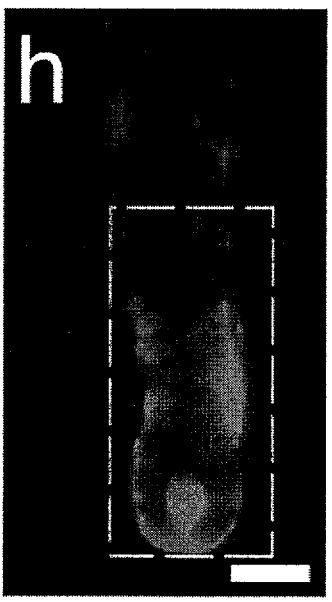

These data are consistent with the idea that SKPs represent an endogenous dermal stem cell. Two cardinal properties of stem cells are self-renewal and multipotentiality, and one of the most striking assays of in vivo stem cell functionality is the ability of isolated hematopoietic stem cells (HSCs) to serially repopulate the blood system. We therefore asked whether genetically-tagged SKPs that had reconstituted their hair follicle niche could be reisolated, expanded, and subsequently reconstitute secondary, de novo hair follicles. To do this, the patch assay was used to generate hair follicles where the entire DP and DS were comprised of genetically-tagged cells (FIGS. 18G and 18H). Cells were dissociated from these follicles and cultured in SKPs proliferation medium. Ten to fourteen days later, genetically-tagged spheres were observed that could be passaged (FIG. 18I). When these secondary spheres (after one passage) were mixed with epidermal cells in the patch assay, they induced de novo hair follicle formation (FIG. 18J). Using this approach, we could serially repopulate hair follicles with SKPs up to three times. However, the SKPs generated from tertiary follicle reconstitutions lost their inductive ability (FIG. 18K), similar to what is seen with serial HSC blood reconstitution.

Figure 19A:
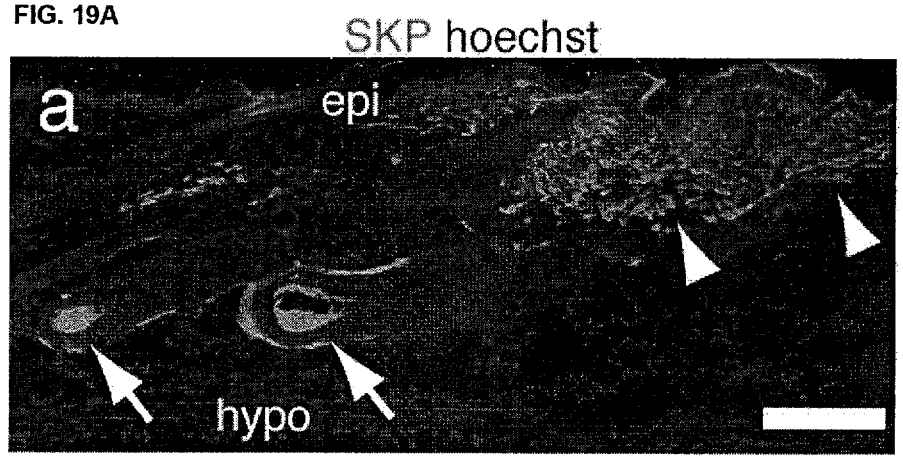
Figure 19B:
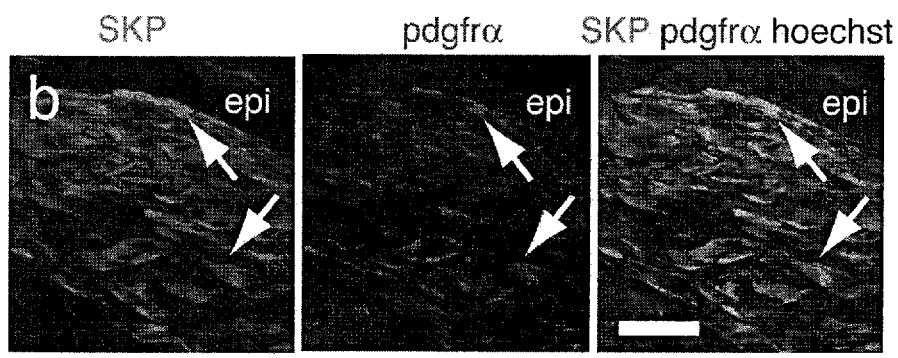
Figure 19C:
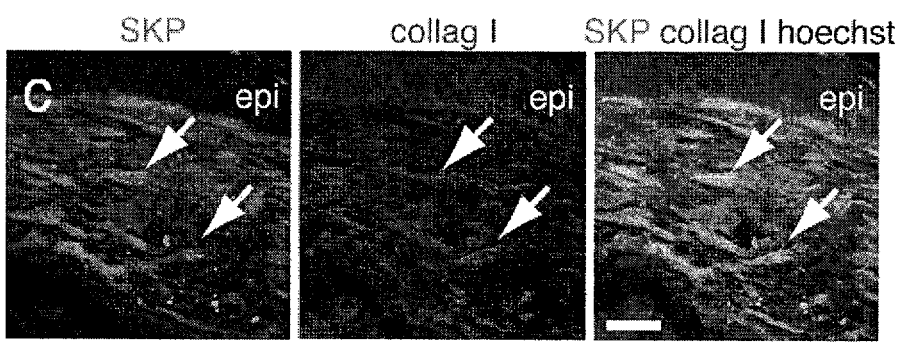
Figure 19H:
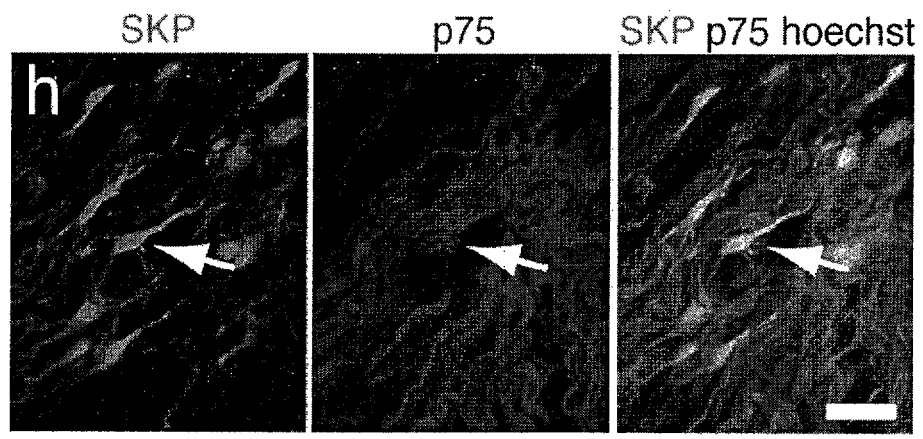
Figure 19I:
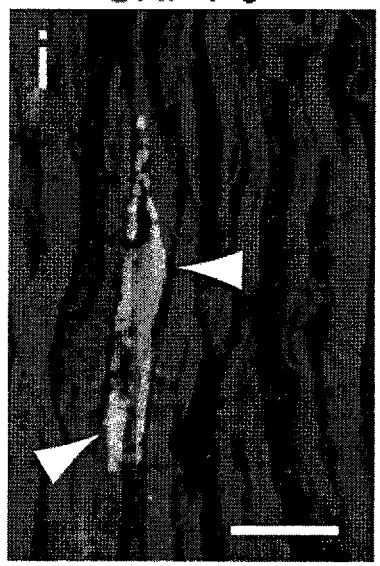
Figure 19J:
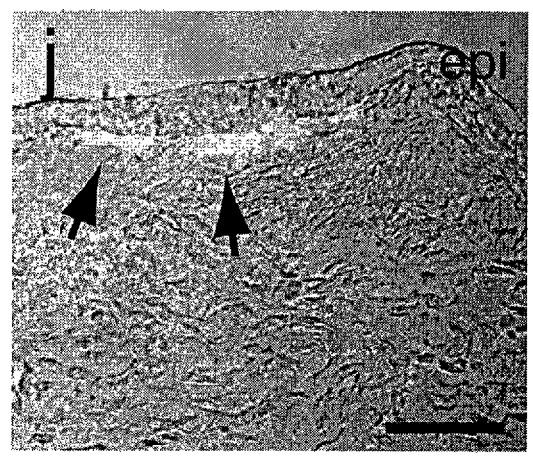
Figure 19K:
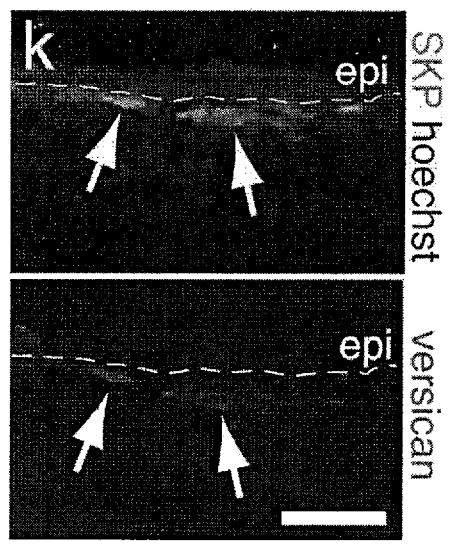
Figure 19L:
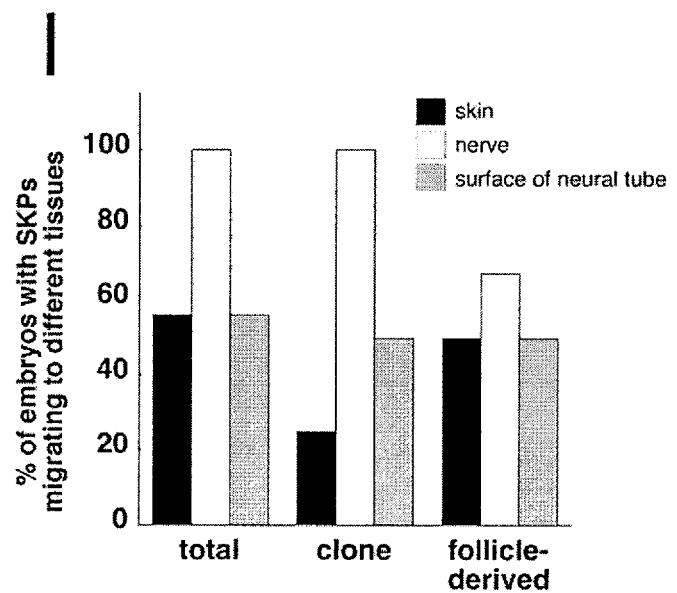
Figure 21B:
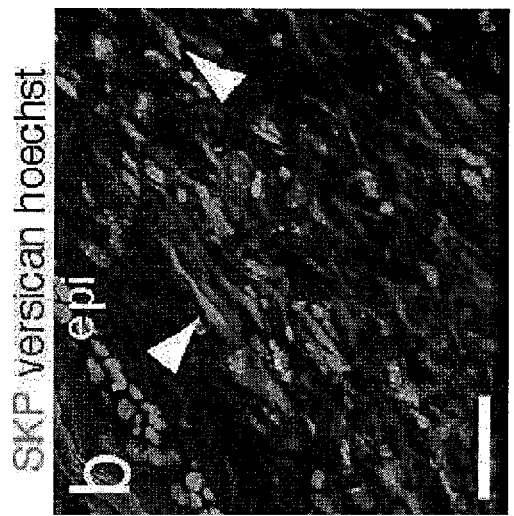
FIGS. 21A-21D are a photomicrographs showing that SKPs participate in dermal wound healing.
Figure 21A:
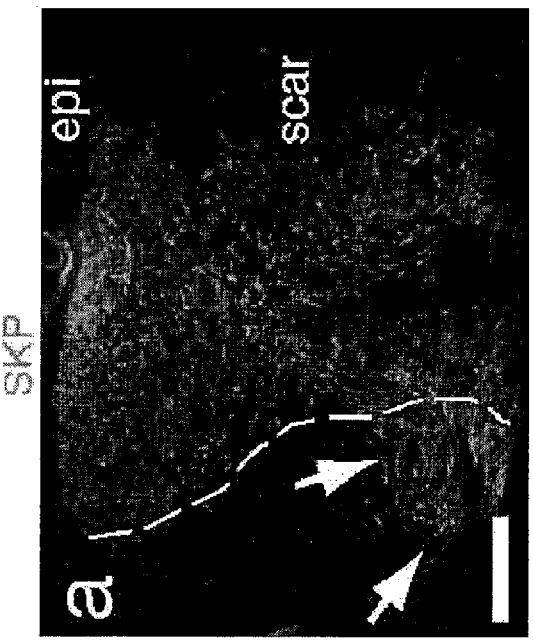
Figure 21C:
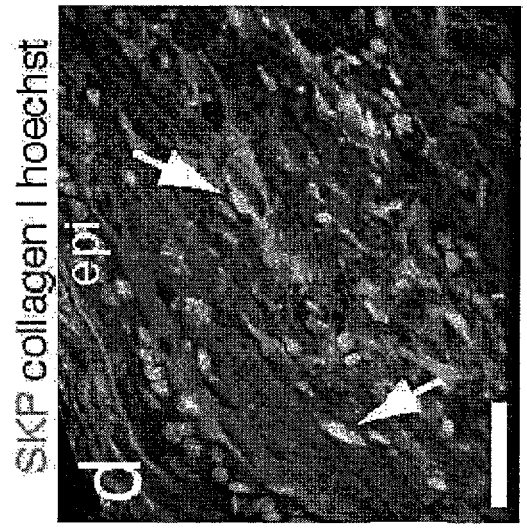
Figure 21D:
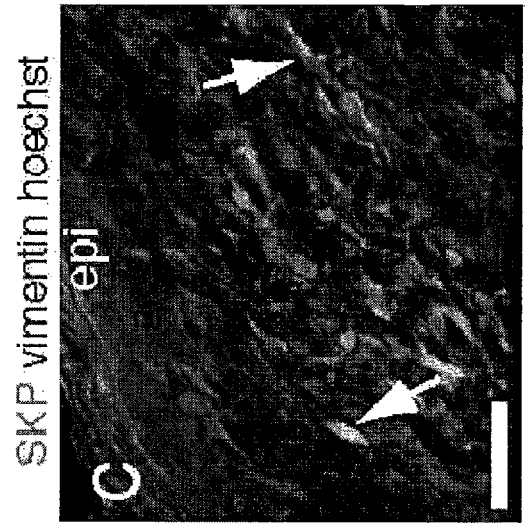

Four lines of evidence indicate that SKPs generated from these reconstituted hair follicles maintain their multipotency. First, when follicle-derived SKPs were transplanted into adult NOD/SCID mouse skin, they generated interfollicular dermal fibroblasts, and homed back and integrated into the DS and DP of follicles, where they expressed appropriate markers (FIGS. 19A-19C and 24). Second, when differentiated under conditions defined for neonatal SKPs, follicle-derived SKPs generated adipocytes, nestin- and βIII-tubulin-positive cells with the morphology of neural precursors and neurons, and SMA-positive myofibroblasts/smooth muscle cells (FIGS. 19D-19G). They also generated cells with characteristics of osteocytes and chondrocytes. Third, when transplanted into the injured sciatic nerve of NOD/SCID mice, a subpopulation of follicle-derived SKPs progeny aligned with axons, and expressed P0 and p75NTR (FIGS. 19H and 19I), markers of Schwann cells. Finally, when follicle-derived SKPs were transplanted into the embryonic chick neural crest migratory stream, the majority migrated out of the neural tube and into neural crest targets such as the spinal nerve and DRGs, in a manner analogous to that seen with total SKPs (Fernandes et al. (2004) Nature Cell Biol 6:1082-1093) (FIG. 19L). Intriguingly, a subpopulation of both total and follicle-derived SKPs migrated to the presumptive dermis, and at late timepoints, some of these expressed the DP marker versican (FIGS. 19J-19L). Thus, follicle-derived SKPs reconstitute the dermis, induce hair follicles, self-renew, maintain their multipotency, and home to a dermal niche within the embryonic chick.

Figure 28:
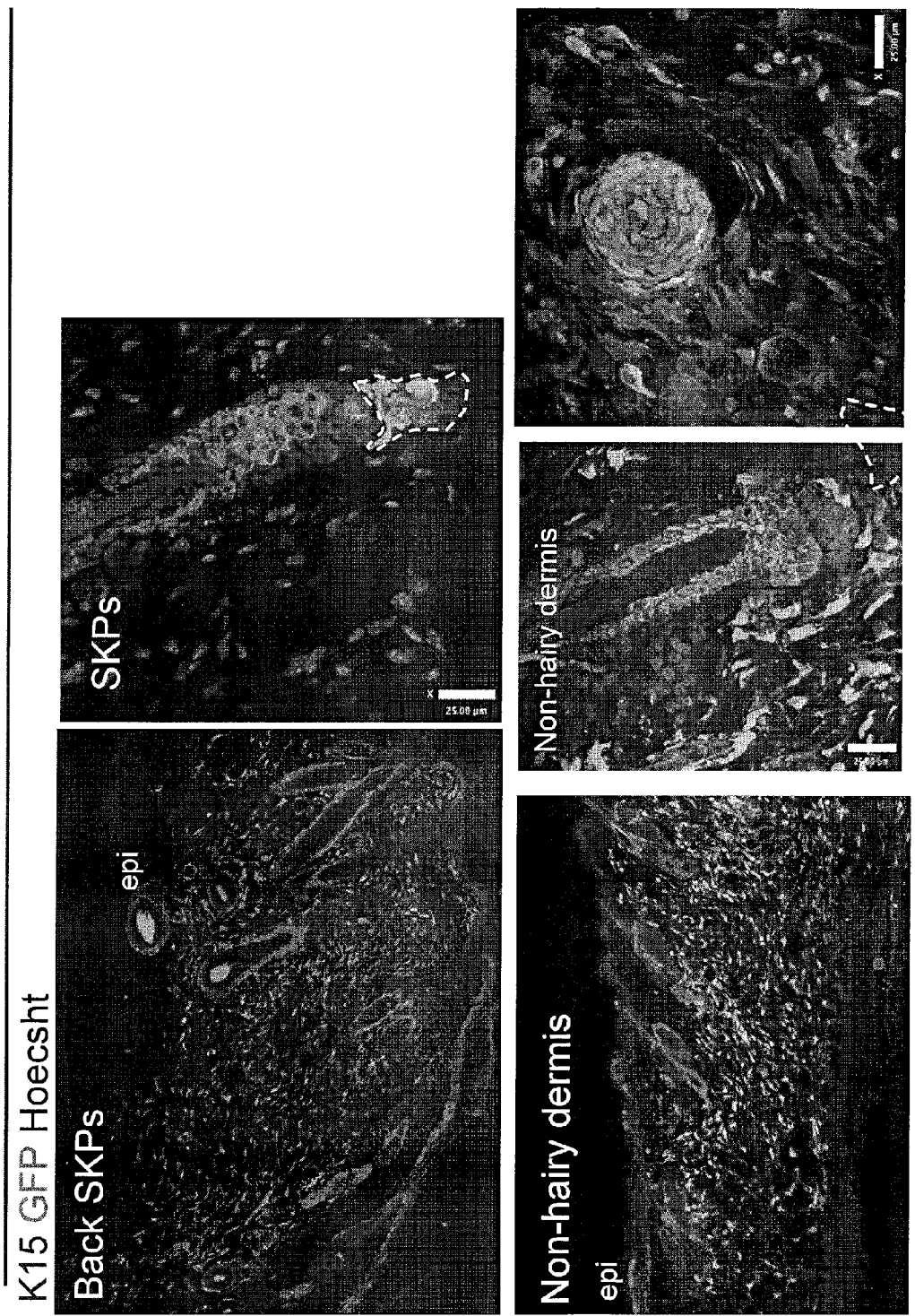
FIG. 28 shows that SKPs from Sox2GFP mice, but not dermal fibroblasts from non-hairy skin, home to hair follicles. Staining with keratin 15, GFP, and hoecsht shows that GFP expressing SKPs are found in hair follicles, (top panels), whereas fibroblasts from non-hairy dermis do not incorporate into follicles (bottom panels).

We have also shown that SKPs, but not dermal fibroblast cells from non-hairy skin home to hair follicles (FIG. 28).

Figure 27:
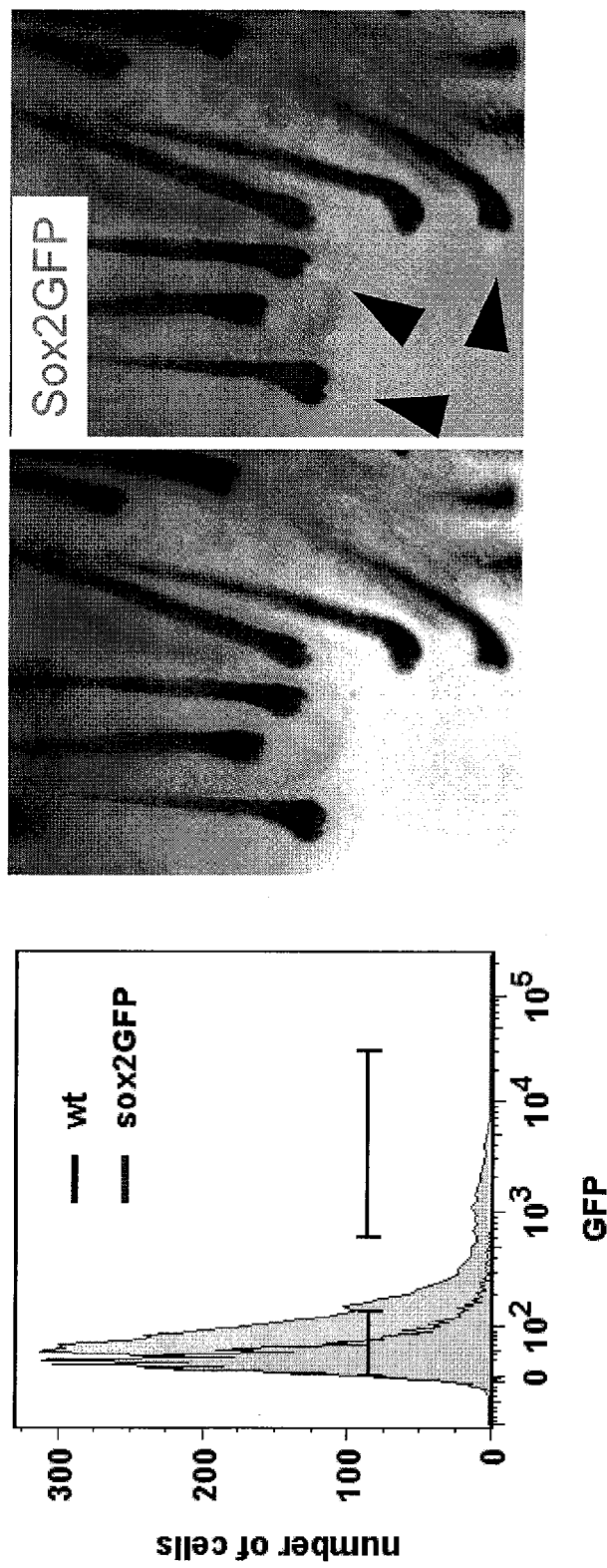
FIG. 27 shows that Sox2 GFP$^+$ cells are found in the skin, and are localized to the hair follicle.
Figure 29A:
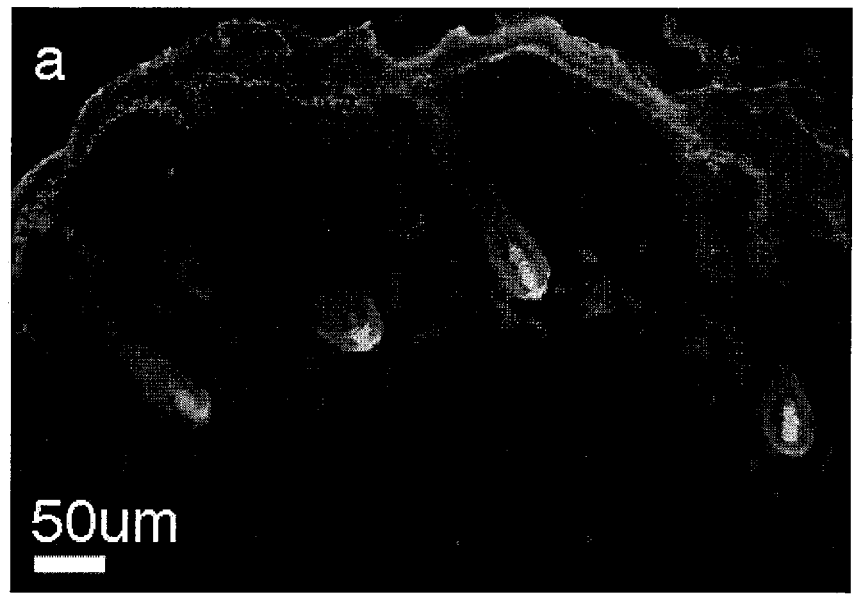
FIGS. 29A-29H are a set of photomicrographs and graphs showing that Sox2$^+$ cells are found in the DP and DS of anagen hair follicles and Sox2$^+$ cells from skin can form spherical colonies, can induce hair follicle formation, and can generate nestin-positive neural precursors.
Figure 29B:
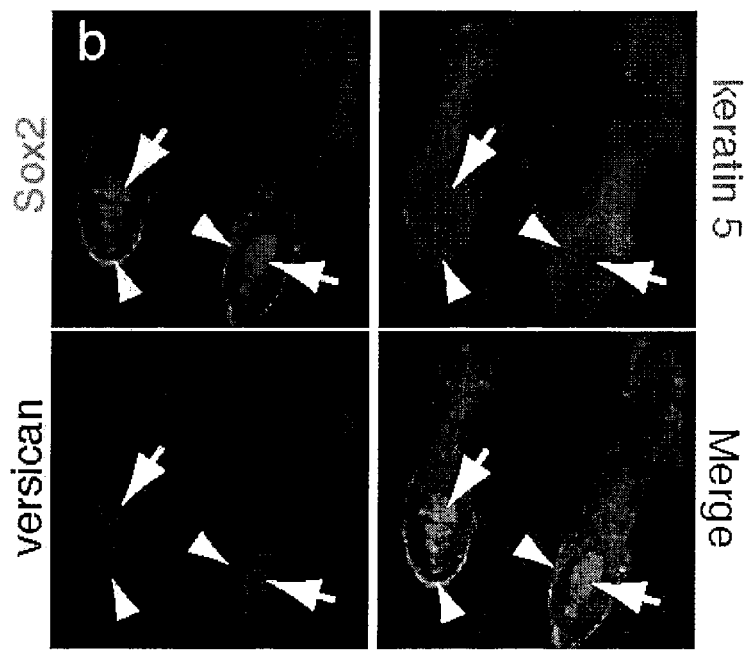
Figure 29C:
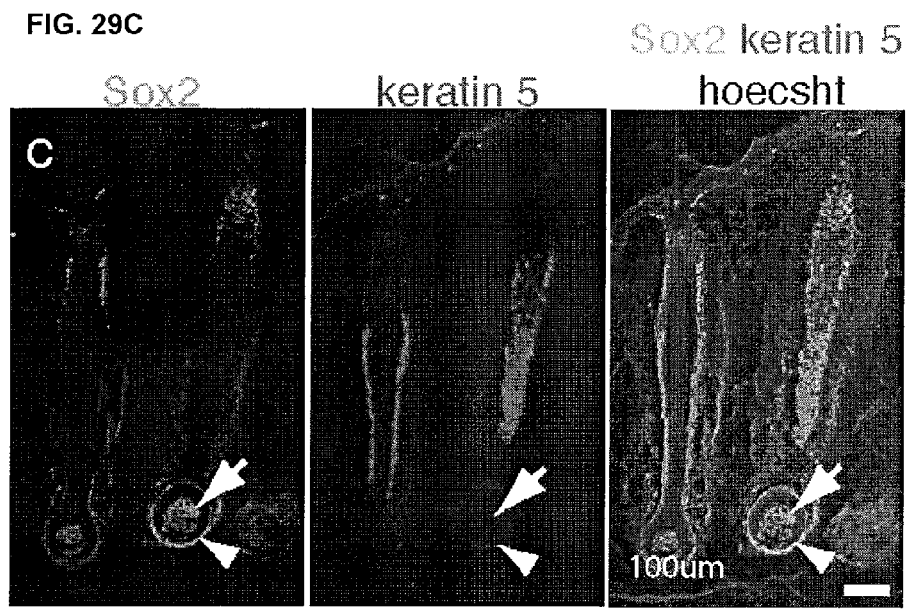
Figure 29D:
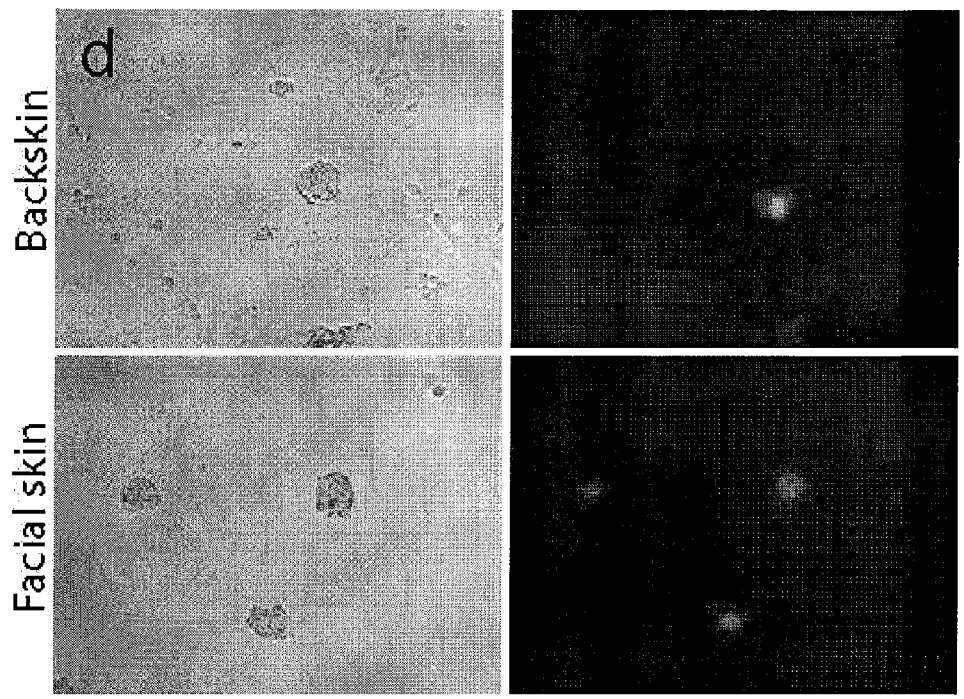
Figure 29E:
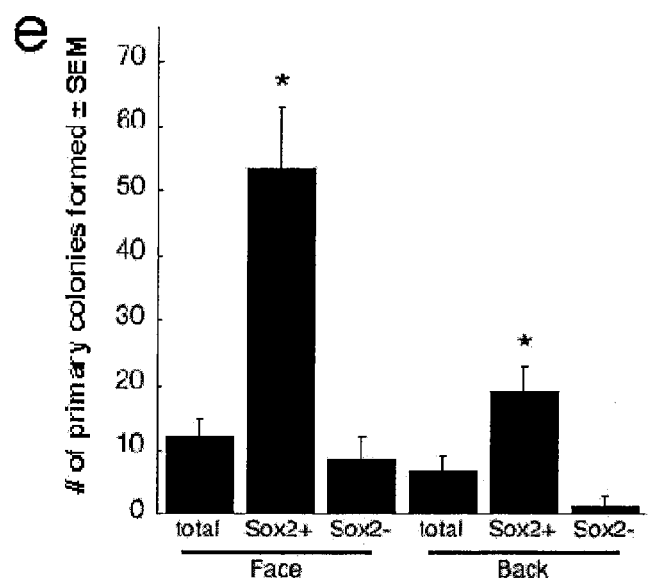
Figure 29F:
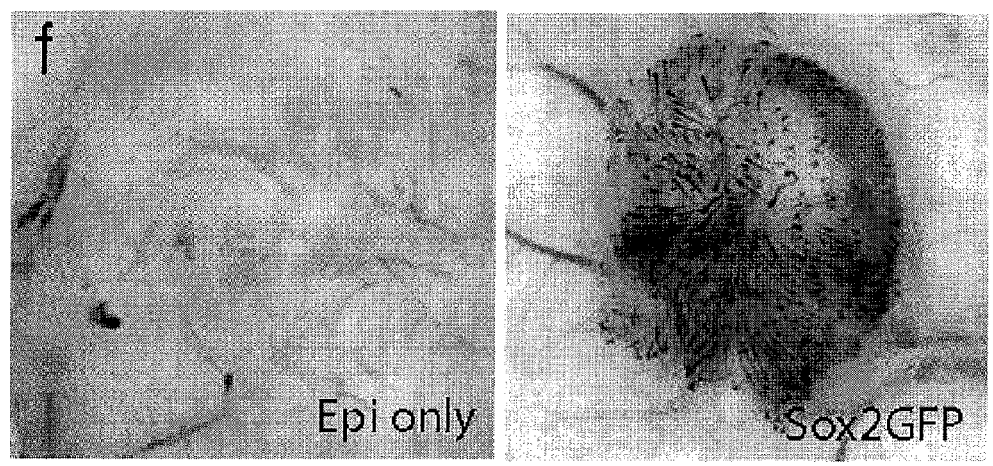
Figure 29G:
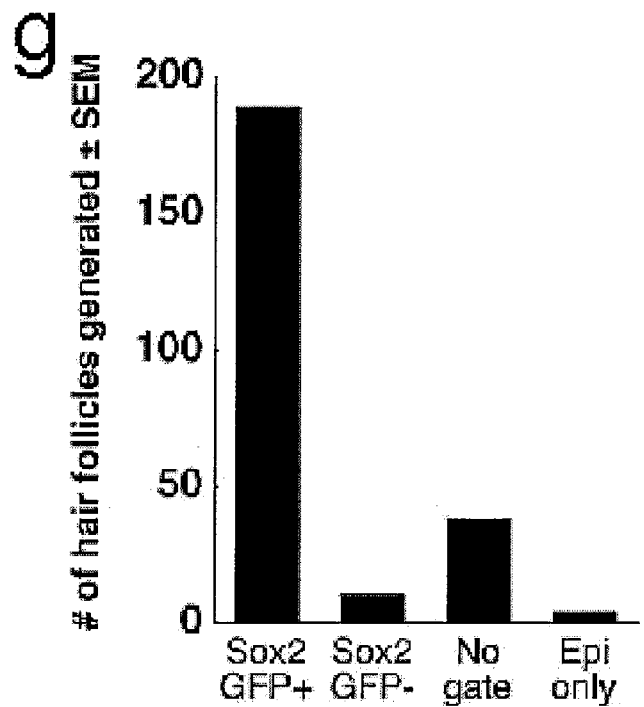
Figure 29H:
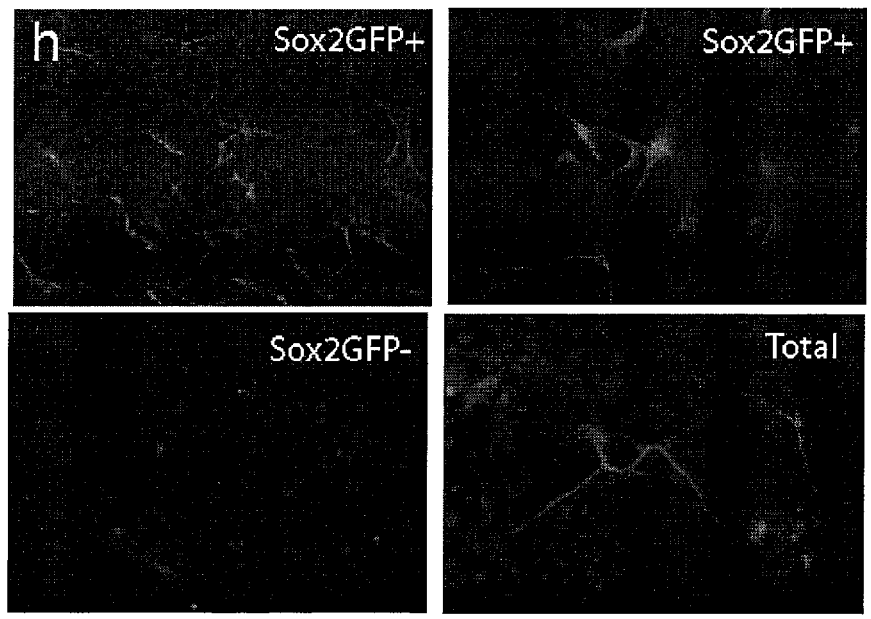

We have further shown that Sox2, a marker of SKPs both in vivo and in isolated cells, is expressed exclusively within the dermal papillae and dermal sheath cells of anagen hair follicles taken from mice expressing GFP under the control of the Sox2 promoter (Sox2GFP mice) (FIG. 27). In particular, this is observed in P2 backskin (FIGS. 29A and 29B) and in whisker pad skin (FIG. 29C). Skin cells dissociated from neonatal Sox2GFP mice form spherical colonies form when the cells are grown in proliferation medium. Many of the colonies are Sox2GFP$^+$ (FIG. 29D). When such cells are fractionated based on GFP expression, facial skin cells show a 5-fold enrichment, and backskin cells show a 2-fold enrichment, for sphere formation relative to total cells (FIG. 29E). Sox2GFP$^+$ cells are also enriched 10-fold for hair follicle formation related to ungated cells or the Sox2GFP$^-$ fraction (FIGS. 29F and 29G). Sox2GFP$^+$ cells are also multipotent, and capable of generating nestin-positive neural precursors, which are not observed in the Sox2GFP$^-$ fraction (FIG. 29H).

These experiments provide evidence for a dermal stem cell that resides within hair follicles, and that can both contribute dermal cells to the intact or injured dermis and induce de novo hair follicle morphogenesis. We propose that these two activities are essential for ongoing dermal maintenance and for the normal cycle of adult follicle morphogenesis. Moreover, we provide evidence that these cells can be actively recruited to their hair follicle niche, and that they are maintained within this niche as undifferentiated multipotent precursors that are capable of self-renewal. The identification of SKPs as an adult dermal stem cell provides a biological rationale for the presence of a multipotent precursor in adult dermis, and suggests an autologous source of precursors for a variety of therapeutic purposes.

Methods

The following methods were used in the experiments described above. Tagged SKPs were generated from dorsal backskin of developing (embryonic day 17 or postnatal day 1-3) YFP-expressing transgenic mice (Hadjantonakis et al. (1998) Mech Dev 76:79-90) or neonatal (P0-P3) and adult (5-10 week old) GFP-expressing transgenic Sprague Dawley rats (SLC, Japan). Cells were cultured at densities of 20,000 cells/ml or less, as previously published (Fernandes et al. (2004) Nature Cell Biol 6:1082-1093; Toma et al. (2001) Nature Cell Biol 3:778-523). Spheres were passaged at 7-14 days and replated at densities of 20,000 cells/ml or less. Secondary spheres (or greater, as indicated in text) were used for all transplant experiments. SKPs were differentiated and clones generated as described (Fernandes et al. (2004) Nature Cell Biol 6:1082-1093; Toma et al. (2001) Nature Cell Biol 3:778-523; Fernandes et al. (2006) Exp Neurol 201:32-48)

For skin transplantation experiments, $2\times10^5$ to $10^6$ dissociated YFP-tagged murine (n=8) or GFP-tagged rat (n=12) SKPs were transplanted into the dorsal backskin dermis of 42-48 day old (telogen) NOD/SCID mice. Immediately prior, backskin was either shaved or depilated and animals were examined 2 to 4 weeks later. Alternatively, SKPs were transplanted adjacent to or into a 3 mm wide full-thickness punch wound.

For hair follicle induction, SKPs (n=6 adult, n=4 neonatal) were analyzed in patch assays as published (Zheng et al. (2005) J Invest Dermatol 124:867-76). Backskin epithelial aggregates were isolated from newborn C57BL/6 mice as described (Weinberg et al. (1993) J Invest Dermatol 100:229-36), and approximately 10,000 epidermal aggregates (or approximately $5\times10^5$ single cells) were mixed with varying concentrations of SKPs. Controls were newborn (n=2) or adult rat dermal cells (n=3), bone marrow-derived MSCs (n=3) or neonatal forebrain neurospheres (n=3).

For serial reconstitution of hair follicles, genetically-tagged SKP-derived hair follicles were isolated from patch assays, and digested in collagenase (Type XI) at 37° C. for 30 minutes. In some experiments, follicles were digested in 0.25% trypsin-EDTA for 20 minutes. Digested tissue was triturated to single cells, and cultured at 2,000 to 10,000 cells/nil in SKPs proliferation medium. After 10 to 14 days, the genetically-tagged spheres were dissociated and $2\times10^5$ to $1\times10^6$ cells were used in patch assays. Reconstitution experiments were performed four times, twice with neonatal (P1-P3) and twice with adult (8 weeks old) SKPs from four different skin samples.

Additional methods are described below.

Tissue Culture.

For skin and hair reconstitution assays, dorsal back skin was removed from embryonic (E17/18) YFP-expressing transgenic mice (Hadjantonakis et al. (1998) Mech Dev 76:79-90) (Jackson Laboratory) or postnatal (P0-P3) or adult (5-10 week old) GFP-expressing transgenic Sprague Dawley rats (SLC, Japan) and cultured according to procedures previously described ((Fernandes et al. (2004) Nature Cell Biol 6:1082-1093; Toma et al. (2001) Nature Cell Biol 3:778-523). Briefly, skin was digested in collagenase type XI (1 mg/ml; Sigma), dissociated to single cells, filtered and grown at densities between 1,000 to 20,000 cells/ml. SKPs proliferation medium consisted of DMEM:F12 (3:1; Invitrogen) supplemented with 2% B27 (Invitrogen) and 40 ng/ml each of FGF2 and EGF (BD Biosciences). Primary SKPs spheres generated after 7-21 days of culture were passaged by collagenase digestion and resuspended as single cells at densities ranging from 1,000 to 20,000 cells/ml. Secondary (or greater) passage spheres were used for transplant experiments.

To generate clonal SKP colonies, secondary spheres were dissociated to single cells and grown at a density of 1,000 cells/ml, a density where little or no mixing of spheres occurs. Individual single clonal spheres were isolated, dissociated to single cells and replated in proliferation medium. Clonal cultures were fed every three days and expanded for a minimum of 5 weeks. MSCs were isolated from bone marrow of adult GFP-expressing rats (generously provided by Dr. Fabio Rossi, U.B.C.). MSC's were plated on uncoated culture dishes at a density of 50,000 cells/ml and grown in Mesencult human MSC medium containing 10% fetal bovine serum (FBS; both from Stem Cell Technologies). YFP-labeled neurospheres were generated from P1 forebrain lateral ventricles as described (Reynolds et al. (1992) Science 255:1707-10; Reynolds et al. (1992) J Neurosci 12, 4565-74; Morshead et al. (1994) Neuron 13:1071-82).

Skin Transplantation.

Passaged SKPs were injected into dorsal backskin of six-week old adult NOD/SCID mice (Charles River laboratories) that was depilated (n=11) or shaved (n=10) immediately prior to transplantation. Alternatively, a 3 mm wide biopsy punch was used to make a full thickness wound in the dorsal backskin, and GFP-labelled SKPs (approximately $5\times10^5$ to $10^6$ cells) were injected intradermally into intact tissue adjacent to the wound. Control transplants were performed with MSCs (n=4) or NSCs (n=4). Skin was analyzed 2 to 8 weeks later. To assess recruitment to the follicle niche, equal numbers of genetically-tagged SKPs were injected intradermally following shaving (telogen) or depilation. The number of follicles containing GFP-positive cells within the DS and DP were counted. To assess hair growth in these experiments, transplanted regions were identified and individual follicles were plucked. 30-50 hairs were analyzed from each transplant and compared to hairs from adjacent non-transplanted regions. Length and width were measured using a Leica stereoscope at 0.7× or 12× magnifications, respectively. For width measurements, awl-type hairs were used for hair width comparison.

Cell Sorting.

Skin from neonatal (P0-P3; n=3) and adult (n=2) Sox2EGFP mice were enzymatically digested and dissociated to a single cells suspension as described above. Viable cells were identified with propidium iodide and then $GFP^+$, $GFP^-$ and ungated populations were collected and fractionated cells were subsequently grown in proliferation medium at a density of 10,000 cells/ml. In addition, 300,000 cells from each population were infected with GFP retrovirus (kind gift of Drs. Akitsu Hotta and James Ellis, Hospital for Sick Children, Toronto, ON) in the presence of 4 µg/ml polybrene. Sorted cells were immediately incubated in virus-containing medium for 18 hours, washed extensively in fresh medium and then injected into the backskin of adult NOD SCID mice, adjacent to a full thickness skin wound.

Nerve and in ovo chicken embryo transplantation. Genetically-tagged clonal SKPs or follicle-derived SKPs were transplanted into the crushed sciatic nerve of adult NOD/SCID mice distal to the injury, as described (McKenzie et al. (2006) J Neurosci 26:6651-60). In ovo transplants were performed as described (Toma et al. (2001) Nature Cell Biol 3:778-523). Fertile white leghorn chicken eggs were incubated at 37° C. until Hamilton/Hamburger stage 18. The lumbar region was identified and a single GFP-labeled SKP sphere was injected into the dorsal-most region of the neural-crest migratory stream of the developing embryo. Eggs were subsequently sealed and incubated for a further 1 to 9 days (Stage 30 to 35).

Hair Follicle Induction Assay.

For hair follicle patch assays, genetically-tagged SKPs, neonatal or adult dermis, NSCs or MSCs were mixed with newborn epidermal aggregates, the latter isolated as described (Weinberg et al. (1993) J Invest Dermatol 100:229-36), and injected into the back skin of adult athymic nude mice (nu/nu; Charles River) as described (Zheng et al. (2005) J Invest Dermatol 124:867-76). Epidermal aggregates were grafted alone as an additional control in each experiment (n=9) and did not generate hair follicle formation. $10^6$ precursor cells were combined with $5\times10^5$ to $2\times10^6$ epidermal cells and suspended in 30 μl of DMEM medium. Using a 27 gauge Hamilton syringe, the cell suspension was injected intradermally into the dorsal backskin forming a 'bleb'. After 10-12 days, hair follicles were observed within the graft beneath the skin. For all patch assays, SKPs, MSCs, and NSCs were passaged at least once and no more than 5 times. Inductive ability was quantified by counting the total number of hair follicles generated within each graft and the percentage of those containing only GFP-positive cells within the DP. To assess follicle bulb size, grafts containing murine dermis-derived hair follicles or rat SKP-derived follicles were dissected and individual bulb diameters (50 follicles/graft; n=2 grafts for each cell type) measured using Velocity acquisition software and a Leica MZ16F stereomicroscope.

Serial Reconstitution of Follicular Dermal Papillae.

Subcutaneous grafts containing de novo SKP-derived hair follicles were excised, minced, and digested in collagenase (Type XI) at 37° C. for 1 hour. Alternatively, in three experiments, graft-derived hair follicles with GFP-positive DP (n=40 hairs/experiment) were individually dissected from the graft, minced and digested with 0.25% trypsin-EDTA as above. Similar results were obtained with both approaches. Tissues were dissociated to single cells by gentle trituration and grown at 5,000 to 20,000 cells/ml in proliferation medium. After 14 days, floating genetically-tagged spheres were isolated and $2\times10^5$ to $1\times10^6$ cells were combined with newborn epidermal cells in 30 μl of DMEM medium and injected into the dermis. Three successive isolations and expansion of genetically-tagged follicle-derived cells with subsequent follicle reconstitution were performed. Reconstitution experiments were repeated four times with different backskin SKP samples, two adult (8 week old) and two neonatal (P1). Similar results were obtained with all samples.

In Vitro Differentiation.

SKPs were differentiated in vitro under previously-defined conditions for neurons, Schwann cells, and SMA-positive cells (McKenzie et al. (2006) J Neurosci 26:6651-60; Biernaskieet al. (2006) Nat Protocols 1:2803-2812). Adipocytes were differentiated in DMEM-F12 containing 1% penicillin streptomycin, 10% FBS, dexamethasone (1 μM, Sigma), isobutylmethylxanthine (1 mM, Sigma), and insulin (20 μg/mL, Gibco/Invitrogen). Medium was changed every 3 days.

Immunocytochemistry and Histology.

Primary and secondary antibodies are described below. Immunocytochemistry was performed as described (Fernandes et al. (2004) Nature Cell Biol 6:1082-1093; McKenzie et al. (2006) J Neurosci 26:6651-60; Fernandes et al. (2006) Exp Neurol 201:32-48), and immunofluorescence was visualized using a Zeiss Axioplan microscope fitted with deconvolution software (Northern Eclipse, Empix, Mississauga, Canada). Co-localization was confirmed by adjacent 0.2 μm to 1 μm optical slices using a Hamamatsu spinning disk confocal microscope fitted to a Zeiss Axioplan 200 inverted microscope. Cell nuclei and tissue morphology were visualized using Hoechst 33258 (Sigma), red fluorescent Nissl stain (Invitrogen), and propidium iodide (Sigma).

Antibodies.

Primary antibodies used were those raised against versican (1:250; a gift from R. LeBaron), PDGFRα (1:500, Santa Cruz), tyrosinase (1:500, Santa Cruz), mouse fibroblast antigen pan reticular (1:500, Serotec), α-smooth muscle actin (1:500, Sigma), fibronectin (1:500, Sigma), S100β (1:500, Sigma), Pax3 (1:400, Developmental Studies Hybridoma Bank), MBP (1:100, Serotec), Ki67 (1:200, BD Biosciences Pharmingen), nestin (1:500, BD Biosciences Pharmingen), $P_0$ (1:1000, Ayes Labs), p75NTR (1:500, Promega), βIII-tubulin (1:500, Covance), e-cadherin (1:500, Santa Cruz), cd73 (BD Biosciences), collagen type I (1:400), vimentin (1:500), chicken green fluorescent protein (1:1000, all from Chemicon/Millipore) were used as previously described (Fernandes et al. (2004) Nature Cell Biol 6:1082-1093; McKenzie et al. (2006) J Neurosci 26:6651-60). Secondary antibodies used were Alexa488-conjugated goat anti-mouse, -rabbit, or -chicken, Alexa555 goat anti-mouse, -rabbit or -chicken and Alexa647 goat anti-rabbit, -mouse or -rat (1:1000; all from Invitrogen).

Fate Mapping of Hair Follicle Dermal Papilla and Dermal Sheath Cells.

Hair follicles were generated in the patch assay by combining adult GFP-tagged SKPs combined with neonatal epidermal aggregates. After 12 days, grafts were dissected and fully formed hair follicles containing GFP-positive DP and DS were carefully dissected and whole follicles were transplanted into the backskin of immunocompromised NOD SCID mice. Skin incisions were allowed to heal for 3-4 weeks (at which time mature tufts of hair had emerged through the skin), and then harvested for histological assessment. Alternatively, full thickness wounds were made adjacent to the grafted hair follicles in order to determine whether the GFP-tagged DP or DS cells would migrate to the wound. Skin was allowed to heal and harvested after 3-4 weeks after wounding (See FIGS. 24-26).

Statistics.

All data are represented as mean±SEM. Data were analyzed using two-tailed t-tests or one-way ANOVA where appropriate. A p-value of 0.05 was considered significant. All experiments were done at least in triplicate, unless otherwise noted.

Other Embodiments

All patents, publications, and patent applications, including U.S. Provisional Patent Application Nos. 60/933,302, filed Jun. 6, 2007, and 60/934,419, filed Jun. 13, 2007, cited in this specification are hereby incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for inducing hair follicle formation in a mammal comprising introducing a composition comprising skin derived precursors (SKPs) and keratinocytes into the skin of said mammal, wherein at least 30% of the cells in said composition are SKPs and keratinocytes, and the ratio of said SKPs to said keratinocytes is between 1:20 and 20:1, thereby inducing hair follicle formation, wherein said SKPs express nestin and fibronectin, are capable of generating floating spherical colonies when grown in the presence of fibroblast growth factor (FGF2) and epidermal growth factor (EGF), and are multipotent stem cells.

2. The method of claim 1 further comprising isolating SKPs from the hair follicles produced by introducing said composition; and introducing said isolated SKPs and keratinocytes into the skin of said mammal.

3. A method for inducing hair follicle formation in a mammal comprising the steps of:
 (a) providing a first cellular composition wherein at least 20% of said cells are SKPs, wherein said SKPs express nestin and fibronectin, are capable of generating floating spherical colonies when grown in the presence of FGF2 and EGF, and are multipotent stem cells;
 (b) providing a second cellular composition wherein at least 20% of said cells are keratinocytes; and
 (c) combining said first and second compositions, and
 (d) transplanting said combined compositions into the skin of said mammal thereby inducing hair follicle formation.

4. The method of claim 3 further comprising the steps of:
 (e) isolating SKPs from the hair follicles produced by step (c); and
 (f) combining said SKPs of step (e) and keratinocytes, and
 (g) transplanting said combined SKPs and keratinocytes of step (f) into the skin of said mammal.

5. The method of claim 1, wherein said mammal is a human.

6. The method of claim 1, wherein said method is performed in conjunction with treating a skin wound.

7. The method of claim 1, wherein said mammal is suffering from alopecia, male pattern baldness, or female pattern baldness.

8. A method for inducing hair follicle formation in a mammal comprising the steps of:
 (a) isolating a cellular composition from said mammal containing SKPs, wherein said SKPs express nestin and fibronectin, are capable of generating floating spherical colonies when grown in the presence of FGF2 and EGF, and are multipotent stem cells;
 (b) providing keratinocytes;
 (c) culturing said cellular composition to produce a composition that contains at least 20% SKPs; and
 (d) combining said composition containing at least 20% SKPs and said keratinocytes, and
 (e) transplanting said combined SKPs and keratinocytes into said mammal, thereby inducing hair follicle formation.

9. The method of claim 8, wherein said mammal is a human.

10. The method of claim 8, wherein said method is performed in conjunction with treating a skin wound.

11. The method of claim 8, wherein said mammal is suffering from alopecia, male pattern baldness, or female pattern baldness.

12. A composition comprising SKPs and keratinocytes, wherein said SKPs and said keratinocytes comprise at least 30% of the cells of said composition and the ratio of SKPs to keratinocytes is between 20:1 and 1:20, wherein said SKPs express nestin and fibronectin, are capable of generating floating spherical colonies when grown in the presence of FGF2 and EGF, and are multipotent stem cells.

* * * * *